US010203333B2

(12) United States Patent
Zhou et al.

(10) Patent No.: US 10,203,333 B2
(45) Date of Patent: Feb. 12, 2019

(54) ELECTRONICALLY NEUTRAL METAL COMPLEXES AS BIOLOGICAL LABELS

(71) Applicant: Rubipy Scientific, Inc., Ottawa (CA)

(72) Inventors: Ming Zhou, Ottawa (CA); Linpo Yu, Nottingham (GB)

(73) Assignee: Rubipy Scientific, Inc., Greely, Ontario (CA)

( * ) Notice: Subject to any disclaimer, the term of this patent is extended or adjusted under 35 U.S.C. 154(b) by 39 days.

(21) Appl. No.: 14/899,825

(22) PCT Filed: Jun. 18, 2014

(86) PCT No.: PCT/IB2014/001115
§ 371 (c)(1),
(2) Date: Dec. 18, 2015

(87) PCT Pub. No.: WO2014/203067
PCT Pub. Date: Dec. 24, 2014

(65) Prior Publication Data
US 2016/0146826 A1    May 26, 2016

Related U.S. Application Data

(60) Provisional application No. 61/956,810, filed on Jun. 18, 2013.

(51) Int. Cl.
*G01N 33/00* (2006.01)
*G01N 33/58* (2006.01)
(Continued)

(52) U.S. Cl.
CPC ....... *G01N 33/582* (2013.01); *C07F 15/0053* (2013.01); *C09K 11/07* (2013.01);
(Continued)

(58) Field of Classification Search
CPC .................................................. G01N 33/582
(Continued)

(56) References Cited

U.S. PATENT DOCUMENTS

| 2003/0027357 | A1* | 2/2003 | Sigal ................... C07D 213/30 436/518 |
| 2005/0253135 | A1 | 11/2005 | Stossel et al. |
| 2008/0145526 | A1* | 6/2008 | Mao .................... C07F 15/0053 427/157 |

FOREIGN PATENT DOCUMENTS

| CA | 2451962 | 1/2003 |
| WO | 0146209 | 6/2001 |

OTHER PUBLICATIONS

Daniel A. Freedman, Jon K. Evju, Marie K. Pomije, and Kent R. Mann "Convenient Synthesis of Tris-Heteroleptic Ruthenium(II) Polypyridyl Complexes" Inorg. Chem. 2001, 40, 5711-5715 (Year: 2001).*
Seann P. Mulcahy, Shan Li, Ricarda Korn, Xiulan Xie, and Eric Meggers "Solid-Phase Synthesis of Tris-heteroleptic Ruthenium(II) Complexes and Application to Acetylcholinesterase Inhibition" Inorg. Chem. 2008, 47, 5030-5032 (Year: 2008).*
International Search Report dated Oct. 9, 2014; International Application No. PCT/IB2014/001115; International Filing Date: Jun. 18, 2014; 4 pages.

(Continued)

*Primary Examiner* — Christine T Mui
*Assistant Examiner* — Emily R. Berkeley
(74) *Attorney, Agent, or Firm* — Francine F. Li; Eckert Seamans Cherin & Mellott, LLC

(57) ABSTRACT

The invention relates to electronically neutral metal complexes as luminescent labels. The positive charge of the metal ion in the complex is neutralized by the negatively charged groups that are covalently linked to the nitrogen-containing diimine ligands, such as 2,2-bipyridine, 1,10-phenanthroline and their derivatives. The electronic neutrality reduces the impact of the metal complexes on the biological and/or biochemical activities of the labeled biomolecules, while the intensity of luminescent emission under electrochemical excitation is enhanced. These luminescent metal complex labels are useful in bioanalytic (Continued)

methodology development, with luminescence as the signal modality, such as electrochemiluminescence.

13 Claims, 15 Drawing Sheets

(51) Int. Cl.
   *C09K 11/07* (2006.01)
   *C07F 15/00* (2006.01)
(52) U.S. Cl.
   CPC ............... *C09K 2211/1011* (2013.01); *C09K 2211/1029* (2013.01); *C09K 2211/1044* (2013.01); *C09K 2211/185* (2013.01)
(58) Field of Classification Search
   USPC ........................................................ 436/172
   See application file for complete search history.

(56) References Cited

OTHER PUBLICATIONS

Della Ciana, L. et al.: "Neutral and Dianionic Ru (II) Bathophenanthrolinedisulfonate Complexes: A Route to Enhance Electrochemiluminescence Performance in Aqueous Media;" Journal of Physical Chemistry C., vol. 114, 2010, pp. 3653-3658.
Compound with CAS344437-00-9; entry date Jul. 3, 2001; "Ruthenium, (1,10-phenanthrolin-5-amine-kN1, kN10)(1,10-phenanthroline-kN1, kN10)[[4,4'-(1,10-phenanthroline-4,7-diyl-kN1, kN10)bis[benzenesulfonato]](2-)]-(9CI)"; 1 page.
Written Opinion dated Oct. 23, 2014; International Application No. PCT/IB2014/001115; International Filing Date: Jun. 18, 2014; 6 pages.

* cited by examiner

A  Label with a positively
   charged ECL luminophore
   e.g., US 6140138, 6316607

B  Label with a positively charged
   ECL luminophores and a charge carrier
   e.g., US 5958783

C  Label with a negatively
   charged ECL luminophore
   e.g., US 6808939

D  Label with a neutral ECL luminophore
   this invention

ELECTRONICALLY NEUTRAL METAL COMPLEXES AS BIOLOGICAL LABELS

CROSS REFERENCE TO RELATED APPLICATIONS

This application is a U.S. National Stage Application under 35 U.S.C. § 371 of PCT Application No. PCT/IB2014/001115, filed Jun. 18, 2014, which in turn claims the benefit of U.S. Provisional Application No. 61/956,810, filed Jun. 18, 2013.

FIELD OF THE INVENTION

This invention relates to bioconjugatable luminescent metal complexes and their use as new labeling molecules for chemical, biochemical, biological analyses, such as immunoassay and DNA probing. More specifically, this invention relates to electronically neutral electrochemiluminescent labels and their use in electrochemiluminescence immunoassay.

BACKGROUND OF THE INVENTION

Bioanalytical methods based on bio-affinity (i.e., the selective binding of two biologically active species, such as antibody/antigen) rely largely on biolabels, labeling techniques and detection of the signals generated from the labels. Biolabels are chemical or biochemical substances that yield, by themselves or through physical/chemical interaction with other reagents, detectable signals that could be correlated to the quantity of the analytes of interest. Biolabels include, but are not limited to, molecules containing radioactive atom(s) (radioactivity), luminescent compounds (emitting light under photoexcitation or by chemical reactions), electroactive compounds (generating electronic signal through redox reactions), magnetic particles (magnetic signal), enzymes (generating detectable species or optical signal via the reaction with substrates). A biolabel includes one or more signal generating unit(s) and one or more reactive group(s). The latter readily form covalent bond(s) with biomolecules to be labeled. Labeling is to link one or multiple labels to a biologically active species to form a complex, which maintain the specific bio-affinity towards the analyte.

Through a cascade of electrochemical redox reactions and follow-up chemical reactions with co-reactants (such as tripropylamine disclosed in U.S. Pat. Nos. 6,451,225 and 6,702,986), electrochemiluminescence (ECL) has became a well-established bioanalytical methodology, in which a metal coordination complex, such as ruthenium (II) polydiimine complex, is used as the signal generating unit in the ECL label molecule. U.S. Pat. Nos. (5,221,605, 5,238,808, 5,310,687, 5,714,089, 5,731,147, 6,140,138, 6,316,607) and a number of research articles disclose ECL labels and their application in immunoassay and DNA probing (e.g., G. F. Blackburn et al., *Clin. Chem.* 1991, 37/9, 1534-1539; J. H. Kenten et al., *Clin. Chem.* 1991, 37/9, 1626-1632.).

Improvement of ECL labels has been a long-lasting endeavor. On one hand, there were tremendous attempts to re-design the ruthenium(II) complexes by functionalizing one or more ligand(s) coordinating to the ruthenium(II) ion. On the other hand, efforts in expanding the ECL luminophores from ruthenium(II) complexes to other metal complexes have been extensively made and some are disclosed in patents. For example, U.S. Pat. Nos. 5,858,676 and 6,468,741 disclose the ECL of rare-earth metal complexes and rhenium complexes, respectively. Patent applications WO2012107420, US2013/0323719, US2013/0323857, WO2014019707, WO2014019708 and WO2014019711 disclose new iridium-based complexes as ECL labels.

With respect to the improvement of ruthenium(II) based ECL luminophores, U.S. Pat. No. 5,981,286 discloses ruthenium (II) complexes with hydrophilic bidentate ligands. WO99/15694 discloses a molecular design in which the metal complex luminophore was covalently linked to the co-reactant (i.e., tripropylamine or its analogs). However, because the co-reactant is consumed (rather than recycled) in the process of electrochemiluminescence, its concentration should be much higher than that of the luminophore in a practical electrolyte formulation for bioassays. This approach does not contribute to enhancing ECL intensity. In order to enhance the sensitivity in ECL assays, U.S. Pat. No. 5,679,519 discloses a multi-labeled probe complex comprising a biotinylated bovine serum albumin platform molecule attached by a plurality of electrochemiluminescent labels. It has also been proposed to construct a dendritic scaffold bearing multiple ECL luminophores (US patent application 2005/0059834) and thus achieving multilabeling biomolecules at a single site (see also M. Zhou et al., *Anal. Chem.* 2003, 75, 6708-6717).

Furthermore, the choice of bidentate ligands has gone beyond the basic 2,2'-bipyridine and 1,10-phenaroline types. U.S. Pat. No. 7,750,157 B2 (EP1759204 A1) discloses a ruthenium(II) label design, in which the bioconjugatable arm is linked to a bidentate ligand that is neither 2,2'-bipyridine nor 1,10-phenaroline.

A common feature of these ruthenium (II) ECL luminophores (without a bioconjugatable group) and ECL labels (with a bioconjugatable group) disclosed in patents or reported in research articles, is that they are composed of a positively charged metal complex luminophore (see FIG. 1A) and a non-luminescent counter anion, such as chloride $Cl^-$ or hexafluorophosphate $PF_6^-$, etc. The biological activity or the selective binding capability of the species labeled with such lumiophores could be lowered due to the introduction of the positively charged metal complexes. The lowered biological activity enhances non-specific binding in the affinity-based bioassays, and consequently, reduces the sensitivity and the reproducibility of the bioassays. In view of the disadvantage of labels with a positively charged ECL luminophore, U.S. Pat. No. 5,958,783 (CN 1134154, EP 0720614B1) disclosed a type of ECL labels (see FIG. 1B) featuring a charged linker between the positively charged luminophore and the reactive) functional group (i.e., the bioconjugatable group). According to the disclosure, such labels help to improve the performance of ECL immunoassays due to lowered non-specific binding to proteins. But the signal generating unit (the ECL luminophore) in such labels remains a positively charged metal complex, which needs counter ion(s) to neutralize the positive charge.

Towards the same objective of lowering the adverse non-specific binding, U.S. Pat. No. 6,808,939B2 (CN 1612861A) discloses bidentate ligands (i.e., bipyridine and phenanthroline) bearing charged (in particular, negatively charged) functional groups and ruthenium(II) complex labels (see FIG. 1C) consisting of these charged ligands. These bis-heteroleptic labels, having the structure ML'L"$_2$, are negatively charged and have dissociable counter cations in their molecular structure. The results show a significant reduction in non-specific ECL signal when certain negatively charged luminophores were labeled to antibodies. However, while reducing non-specific signal significantly, no improvement of specific signal level was demonstrated.

These ECL luminophores and labels comprising these luminophores are either (predominantly) positively charged or negatively charged with counter ion(s). They are all ionic compounds and can separate or split into cation(s) and anion(s) in electrolyte solutions. Furthermore, these metal complexes that have been synthesized are either bis-heteroleptic or homoleptic metal complexes, i.e., at least two bidentate ligands of the complexes are the same.

L. Della Ciana et al. (*J. Phys. Chem. C* 2010, 114, 3653-3658) describes a bis-heteroleptic zwitterionic ruthnium(II) luminophore with two identical 2,2'-bipyridine ligands and a bathophenanthroline disulfonate ligand that shows aqueous ECL intensity higher than that of the reference tris(2,2'-bipyridine) ruthenium(II) complex. However, like many other reportedly highly intense ECL luminophores that do not possess a bioconjugatable group, its use in the ECL immunoassay is not feasible, nor is the synthetic approach to introducing a reactive bioconjugatable group to that metal complex established.

The ECL intensity of ruthenium(II) complexes in a specific electrolyte system involving a co-reactant and solvent varies radically with their ligand structures and the combination mode of the ligands. Because of the complexity of the ECL generating process (W. Miao et al, *JACS*, 2002, 124, 14478-14485), it is also generally accepted that there is no correlation between the ECL intensity and any single property, such as photoluminescence efficiency, redox potential, luminescence wavelength and charging state of the luminophores (M. Zhou et al, *Inorg. Chem.* 2005, 44, 8317-8325). However, labeling a biological substance with an electronically neutral luminophore does not change the charging state of the biological substance. Thus, among the labels of similar size or similar molecular weight, electronically neutral labels have the least impact on the biological activity of the labeled substance. Therefore, the present invention is concerned with the design of ligand combination modes in order for metal complexes, such as ruthenium(II) complexes, to become an electronically neutral ECL labels that do not dissociate into cation(s) and anion(s) in aqueous buffer solutions or any other solvent.

While we aim to take advantage of the minimal impact a neutral label has on the labeled substance, we have surprisingly found that not only did the neutral ECL labels reduce non-specific signal, some of the neutral ECL labels also generated more intense ECL.

The syntheses of ruthenium(II) complex labels disclosed in prior art followed predominantly an approach (see below) in which a cis-ruthenium diimine (L) dicholoride, i.e., cis-Ru(L)$_2$Cl$_2$, is first synthesized followed by the coordination of a bioconjugatable diimine ligand to the metal ion.

$$RuCl_3 \cdot xH_2O + L \rightarrow cis\text{-}Ru(L)_2Cl_2 \quad (1)$$

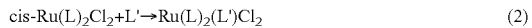

$$cis\text{-}Ru(L)_2Cl_2 + L' \rightarrow Ru(L)_2(L')Cl_2 \quad (2)$$

U.S. Pat. No. 6,808,939 B2 discloses another synthetic approach (Example 2 thereof), in which a bioconjugatable diimine ligand, i.e., 4-methyl-4'-(3-carboxypropyl)-2,2'-bipyridine, is first coordinated with ruthenium(II) chloride followed by the addition of two identical ligands to form the ECL labels.

These synthetic approaches lead to bis-heteroleptic complex labels which possess two identical non-bioconjugatable ligand and a bioconjugatable ligand. The synthesis of a tris-heteroleptic metal complex ECL label has not been described in prior art.

Unlike the labels with the positively and negatively charged ruthenium(II) luminophores in FIG. 1A-C, the exemplary neutral ECL label in FIG. 1D has three different ligands and could not be synthesized by the method used for the bis-heteroleptic complex labels. Therefore, in addition to ligand combination modes disclosed in this invention, the invention is also directed to the synthetic method by which three different diimine ligands are progressively coordinated with the metal ion to form the tris-heteroleptic ECL labels.

The invention further discloses the biological substances labeled with these neutral ECL luminophores and the use thereof in ECL immunoassay.

It is an object of the present invention to provide luminescent biolabels with electronically neutral metal complex luminophores.

It is another object of the present invention to provide different ligand combination modes that result in the electronic neutrality of metal complex luminophores.

It is a further object of the present invention to provide synthetic approach to the tris-heteroleptic labels with electronically neutral metal complex luminophores.

It is still another object of the present invention to provide substances that are labeled with electronically neutral metal complex luminophores.

It is yet another object of the present invention to provide biolabels to perform quantitative ECL assays of chemical, biochemical and biologically active substances.

SUMMARY OF THE INVENTION

The present invention relates to improvement in bioassays, more specifically, immunoassays and nucleic acid assays using electro-generated chemiluminescence or electrochemiluminescence (ECL) of metal complexes. The metal complexes described in the present invention were exemplified with ruthenium(II) complexes. However, other transition metals, such as osmium, platinum, rhenium, iridium etc., which can form metal chelates similar to ruthenium(II) polydiimine complexes, are also contemplated.

DETAILED DESCRIPTION OF THE INVENTION

Figure 1:
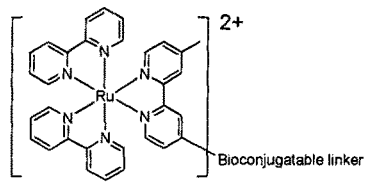
FIG. 1 illustrates the ECL labels disclosed in prior art (A-C) and in the present invention (D).
Figure 1:
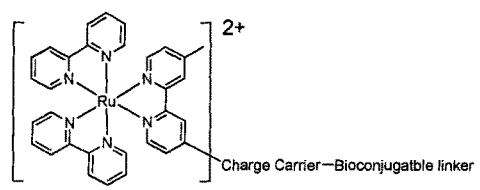
Figure 1:
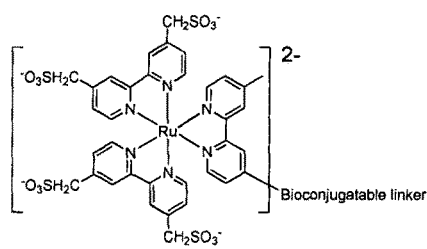
Figure 1:
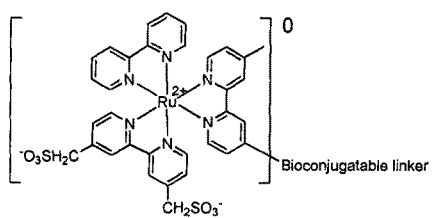

Herein, the terms "metal complex", "coordinating metal complex", "luminescent metal complex", "ECL metal complex", "ruthenium(II) complex", "ruthenium(II) metal complex", and "metal chelate" are sometimes used interchangeably. Within the scope of the invention, the metal complex or ECL metal complex include "luminophore " or "ECL luminophore" and "label" or "ECL label." The former is a metal complex without a bioconjugatable group and the latter is a metal complex with a bioconjugatable group. The bioconjugatable group is a functional or reactive group that can react—under a mild condition, e.g., in physiological buffer solution at room temperature—with other chemical, biochemical and biological species to form a highly stable covalent bond.

It is within the scope of the invention for the species termed "label", "label molecule", "ruthenium(II) label" and "ECL label" to be covalently bonded to other substances such as a biologically active analyte or an analog thereof, an affinity—based recognition partner of the analyte or an analog thereof, and further binding partners of such aforementioned recognition partner, or a reactive chemical capable of forming covalent bond with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog.

The present invention relates to ECL labels with metal complex luminophores that are electronically neutral. The phrase "neutral", "electronically neutral" or "electronic neutrality" as it may be used herein refer to the state in which the positive charge of the metal cation is balanced or neutralized by the anionic multi-atomic substitute groups that are directly or indirectly bonded to one or more aromatic ring(s) of the bidentate (or preferably diimine) ligands that are 2,2'-bipyridine, 1,10-phenanthroline and their derivatives.

Because of the cationic nature of the metal ion in a coordinating metal complex, the electronic neutrality of a label molecule disclosed in prior arts is achieved by the counterion(s). For the ECL labels with positively charged luminophores (see e.g., U.S. Pat. Nos. 5,221,605, 5,238,808, 5,310,687, 5,714,089, 5,731,147, 6,140,138, 6,316,607), the counterions are chloride, hexafluorophoaphate etc. For the ECL labels with negatively charged luminophores (as disclosed in U.S. Pat. No. 6,808,939), the counterion is, e.g., sodium ion or proton. Thus, the ECL luminophores and ECL labels disclosed in prior arts are chemically ionic compounds that dissociate into cation(s) and anion(s) when dissolved in a proper electrolyte solution, such as a phosphate buffer solution.

The ECL labels with electronically neutral luminophores disclosed in the present invention are electronically neutral zwitterions. In the structures of the metal complex luminophores disclosed in this invention, the positive charge of the metal cation is neutralized by the negative charge of the substituents on the aromatic rings of one or more bidentate (or preferably diimine) ligand(s). Thus, the ECL luminophores and ECL labels disclosed in this invention do not dissociate into cation(s) and anion(s) when dissolved in an electrolyte solution These electronically neutral metal complex labels have a general formula $$M^{n+}[L'L''L''']^{n-} \qquad (I)$$

wherein M is selected from the transitional metals, preferably, ruthenium or osmium; n is the number of the electronic charge, equal to or larger than 2; L', L", and L'" are independently) selected from nitrogen-containing heterocyclic bidentate ligands, preferably from 2,2'-bipyridines, 1,10-phenanthrolines and their substituted analogs. At least one of the ligands have at least one bioconjugatable reactive group, such as carboxyl, N-succinimidyl carboxylate (NHS ester), N-hydroxysulfosuccinimidyl carboxylate (sulfo-NHS ester), phosphoramidite, isothiocyanato, formyl, amino, hydrazino, hydroxyl, and maleimido etc.

Based on whether the three diimine ligands are the same or different, the tris-diimine metal complexes can be homoleptic, bis-heteroleptic or tris-heteroleptic. For the dicationic metal ions, such as ruthenium(II), it is impossible to construct a homoleptic tris-diimine complex that possesses an electronic neutrality as aforementioned. Therefore, the present invention is related to bis-heteroleptic and tris-heteroleptic metal complexes, preferably, the tris-heteroleptic metal complexes having the structures $$M^{n+}[L^1 L^2 L^3]^{n-} \qquad (II) \text{ and}$$

$$M^{n+}[L^1 L^4 L^5]^{n-} \qquad (III)$$

wherein M is selected from the transitional metals, preferably, ruthenium or osmium; and n is the number of the electronic charge, equal to or larger than 2.

$L^1$ is a nitrogen-containing heterocyclic bidentate ligand, selected preferably from substituted 2,2'-bipyridines and substituted 1,10-phenanthrolines, as shown below:

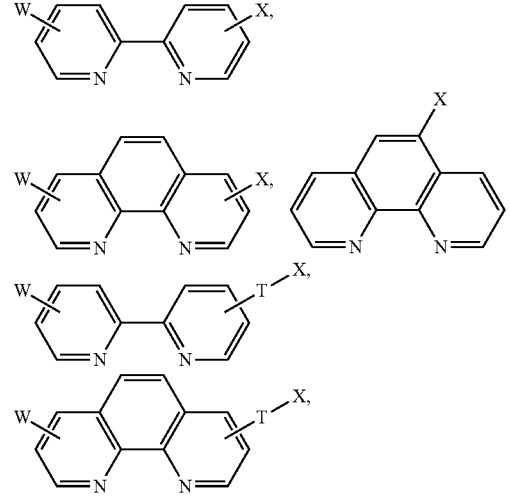

-continued

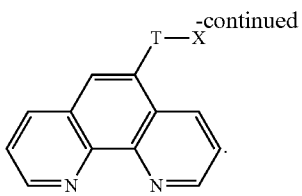

L¹ has at least one reactive group (X), such as carboxyl, N-succinimidyl carboxylate (NHS ester), N-hydroxysulfos-uccinimidyl carboxylate (sulfo-NHS ester), phosphoramidite, isothiocyanato, formyl, amino, hydrazino, hydroxyl, and maleimido, which are directly (without a linker T) or indirectly (through a linker, T) linked to one of the aromatic rings. T is a carbon-containing or a heteroatom-containing linker comprising a $C_1$-$C_{10}$ alkylene, alkenylene, $C_1$-$C_{10}$ alkyloxy, —CONH—$C_1$-$_{10}$—, —NHCO—$C_1$-$C_{10}$—, —$C_1$-$_9$CONHR$_1$—, substituted or unsubstituted 5- or 6-member aromatic ring. W is hydrogen or any uncharged substituent, preferably a $C_1$-$C_{10}$ alkyl, $C_1$-$C_{10}$ alkenyl, $C_1$-$C_{10}$ alkyloxy, —CONH—$C_1$-$_{10}$, —NHCO—$C_1$-$C_{10}$, —$C_1$-$_9$CONHR$_3$, substituted or unsubstituted 5- or 6-member aromatic ring, hydroxyl, amino, nitrile, cyano, or halogen.

L² is a nitrogen-containing heterocyclic bidentate ligand, selected preferably from substituted 2,2'-bipyridine and 1,10-phenanthroline, as shown below:

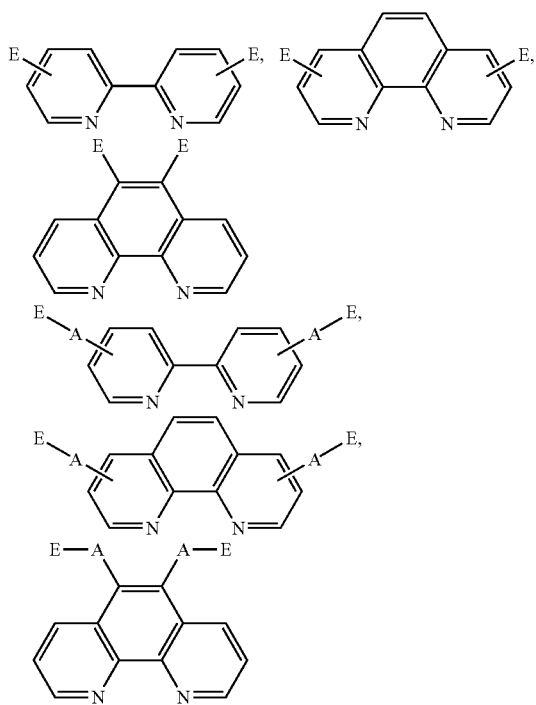

L² has electronically charged substituent(s) with a total number of negative charge equal to n (n is equal to or larger than 2, preferably 2), wherein E is an electronically charged group; and A is a carbon-containing or a heteroatom-containing linker. Preferably, E is a negatively charged group, such as —SO$_3^-$, —OSO$_3^-$, —PO$_3$H$^-$, —OPO$_3$H$^-$ etc.; and A is a carbon-containing or a heteroatom-containing linker comprising a $C_1$-$C_{10}$ alkyl, $C_1$-$C_{10}$ alkenyl, $C_1$-$C_{10}$ alkyloxy, —CONH—$C_1$-$_{10}$—, —NHCO—$C_1$-$C_{10}$—, —$C_1$-$_9$CONHR$_2$—, substituted or unsubstituted 5- or 6-member aromatic ring.

L³ is a charge neutral nitrogen-containing heterocyclic bidentate ligand, selected preferably from uncharged 2,2'-bipyridine, 1,10-phenanthroline, or with at least one substituent W' thereon. The substituent W' is preferably hydrogen or an uncharged and non-reactive under mild aqueous solutions, such as $C_1$-$C_{10}$ alkyl, $C_1$-$C_{10}$ alkenyl, $C_1$-$C_{10}$ alkyloxy, —CONH—$C_1$-$_{10}$, —NHCO—$C_1$-$C_{10}$, —$C_1$-$_9$CONHR$_3$, substituted or unsubstituted 5- or 6-member aromatic ring, hydroxyl, amino, nitrile, cyano, or halogen.

L⁴ and L⁵ are each a mono-anionic nitrogen-containing heterocyclic bidentate ligand, selected preferably from substituted 2,2'-bipyridine and 1,10-phenanthroline, as shown below:

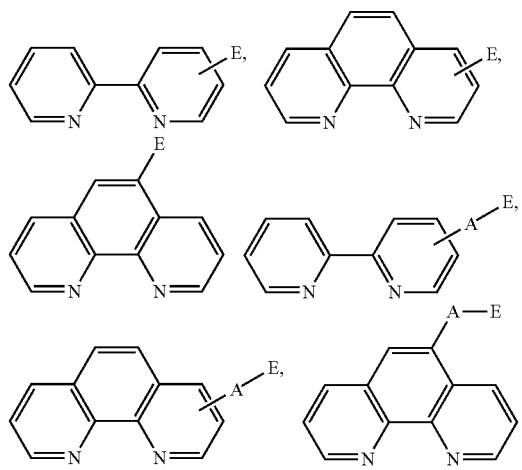

L⁴ and L⁵ each have a negatively charged substituent, wherein E is an electronically charged group and A is a carbon-containing or a heteroatom-containing linker. Preferably, E is a negatively charged group, such as —SO$_3^-$, —OSO$_3^-$, —PO$_3$H$^-$, —OPO$_3$H$^-$ etc.; and A is a carbon-containing or a heteroatom-containing linker comprising a $C_1$-$C_{10}$ alkyl, $C_1$-$C_{10}$ alkenyl, $C_1$-$C_{10}$ alkyloxy, —CONH—$C_1$-$_{10}$—, —NHCO—$C_1$-$C_{10}$—, —$C_1$-$_9$CONHR$_2$—, substituted or unsubstituted 5- or 6-member aromatic ring.

Starting from dichloro(p-cymene)ruthenium(II) dimer, i.e., [(p-cymene)RuCl$_2$]$_2$, through a successive replacement of the two p-cymene molecules by two diimine ligands, the general synthetic procedure below allows three diimine ligands (either the same or different) to coordinate with the metal ion progressively:

[(p-cymene)RuCl$_2$]$_2$, +L'→(p-cymene)(L')RuCl$_2$
(p-cymene)(L')RuCl$_2$+L"→(L")(L')RuCl$_2$
(L")(L')RuCl$_2$+L'"→(L')(L")(L'")Ru
(here, L', L" and L'" are collectively L¹, L² and L³, or are L¹, L⁴ and L⁵)

The present invention provides that the same target tris-heteroleptic complex (L')(L")(L'")Ru could be synthesized from different starting materials and through different intermediates. The particular order of ligand replacement on the ruthenium(II) core is not critical. Such versatility in the ligand replacement sequence helps to reduce the number of synthetic steps needed for preparing a large number of compounds for screening, since common intermediates can be shared for different target compounds.

For example, changing the sequence of the ligand replacement of the above three reactions, we can have the following alternative approach,

[(p-cymene)RuCl$_2$]$_2$, +L'"→(p-cymene)(L")RuCl$_2$
(p-cymene)(L'")RuCl$_2$+L'→(L')(L'")RuCl$_2$
(L'")(L')RuCl$_2$+L"→(L')(L")(L'")Ru
(here, L', L" and L'" are collectively L¹, L² and L³, or are L¹, L⁴ and L⁵)

In sum, the synthetic sequence comprises the following steps. First, forming a first intermediate (p-cymene)(L') RuCl$_2$, (p-cymene)(L")RuCl$_2$, or (p-cymene)(L''')RuCl$_2$ by reacting [(p-cymene)RuCl$_2$]$_2$ with L', L", or L'''. Second, converting the first intermediate to a second intermediate (L')(L")RuCl$_2$, (L')(L''')RuCl$_2$, or (L")(L''')RuCl$_2$ by reacting (p-cymene)(L')RuCl$_2$ with L" or L''', reacting (p-cymene)(L")RuCl$_2$ with L' or L''', or reacting (p-cymene)(L''') RuCl$_2$ with L' or L". Third, converting the second intermediate to (L')(L")(L''')Ru by reacting (L')(L")RuCl$_2$ with reacting (L')(L''')RuCl$_2$ with L", or reacting (L")(L''') RuCl$_2$ with L'. In the above synthetic sequence, L', L", and L''' may be substituted with L$^1$, L$^2$ and L$^3$, or with L$^1$, L$^4$ and L$^5$ in order that all three ligands are placed around the Ru core.

Through a number of synthetic examples, it is demonstrated that any ligand can coordinate with the ruthenium(II) at any stage of the versatile synthetic path. Some examples of L$^1$, L$^2$, L$^3$, L$^4$ and L$^5$, as defined above and below, are listed in Table 1 and were used in the embodiments of the present invention.

TABLE 1

Examples of bidentate diimine ligands used in the embodiments of the present invention.

| L$^1$ Diimine ligand with a reactive group | L$^2$ Di-anionic diimine ligand |
|---|---|

| L$^3$ Diimine ligand without charged group | L$^4$ or L$^5$ Mono-anionic diimine ligand |
|---|---|

As described above, L$^1$ is a bioconjugatably functionalized nitrogen-containing heterocyclic bidentate ligand, selected preferably from 2,2'-bipyridines, 1,10-phenanthrolines and their substituted analogs. L$^1$, either free or coordinated with a metal ion, is capable of reacting or conjugating with a biological substance under a mild condition. The functional or bioconjugatable groups are selected from carboxyl, N-succinimidyl carboxylate (NHS ester), N-hydroxysulfosuccinimidyl carboxylate (sulfo-NHS ester), phosphoramidite, isothiocyanato, formyl, amino, hydrazino, hydroxyl, and maleimido etc. In addition to those listed in Table 1 and used for the syntheses of the exemplary ECL labels in the present invention, L$^1$ can be selected from, but are not limited to, the bioconjugatable diimine ligands below:

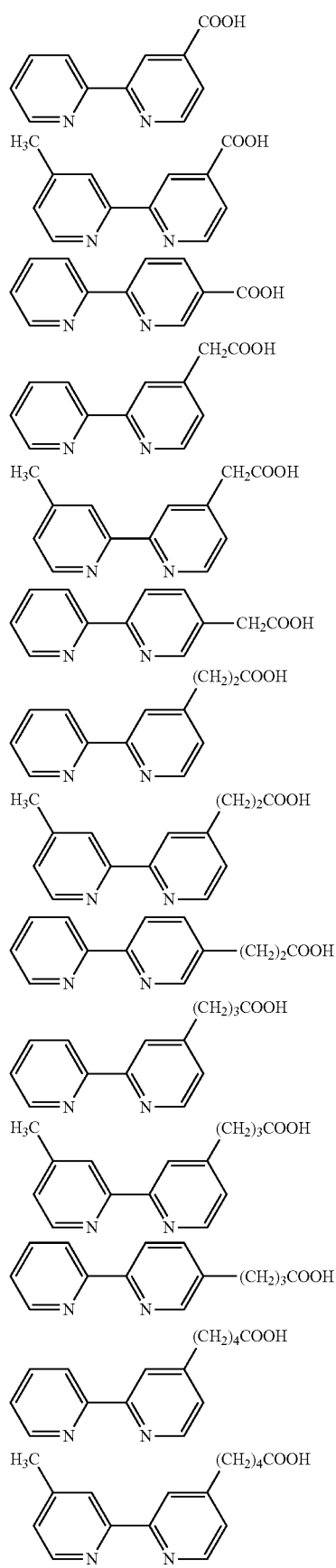
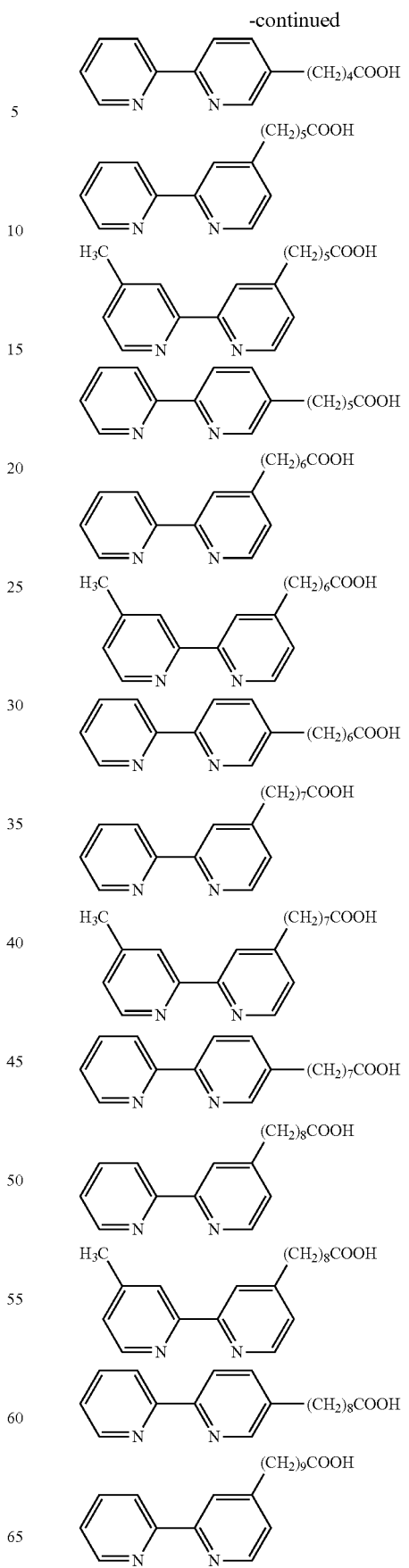

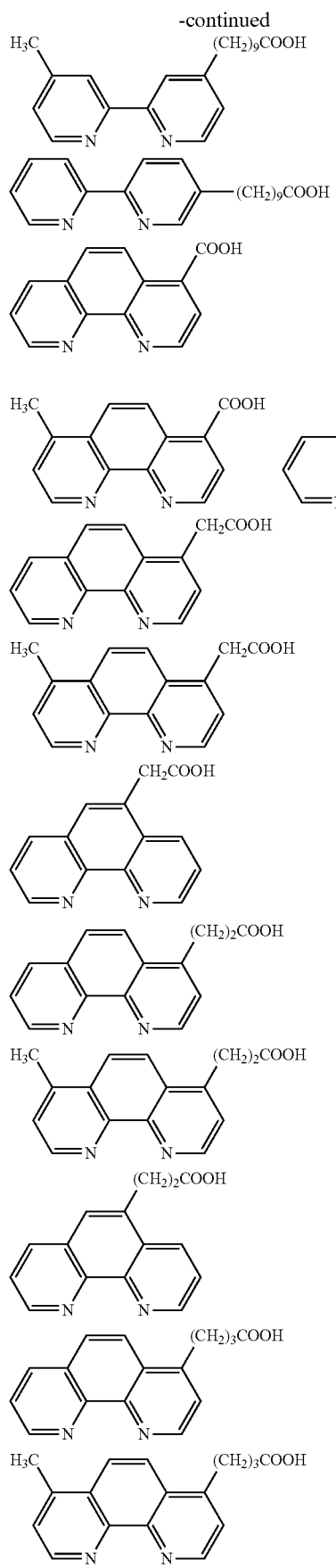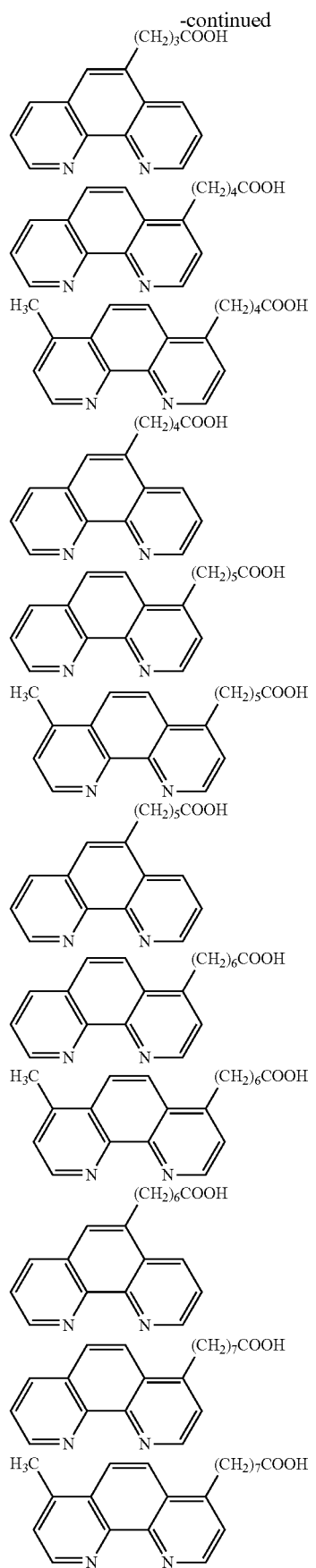

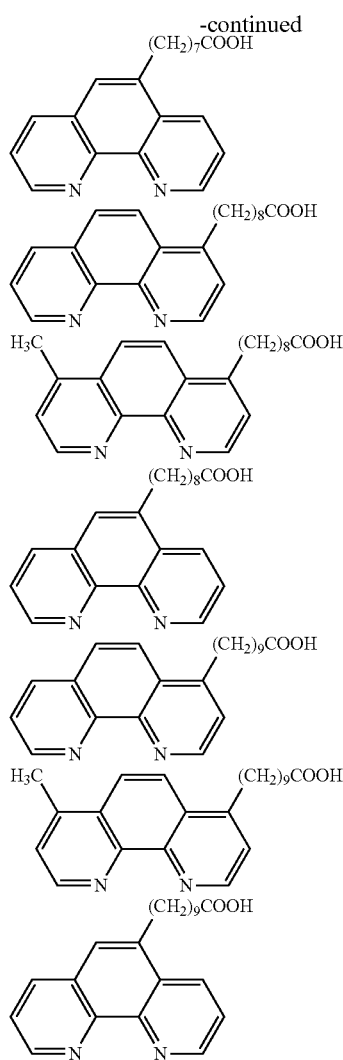

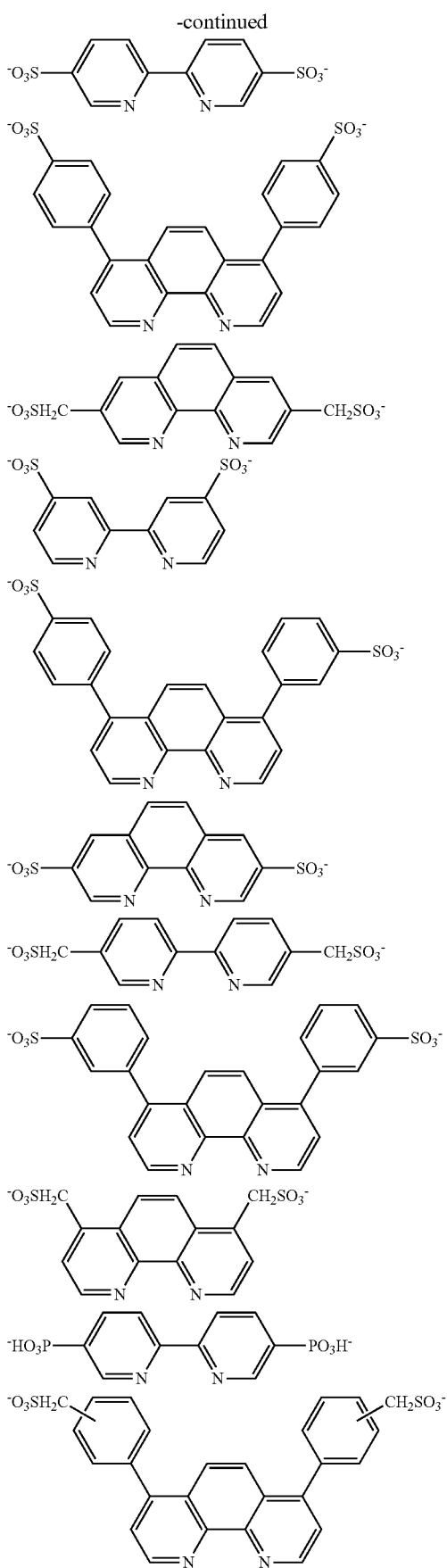

L² is preferably a di-anionic nitrogen-containing heterocyclic bidentate ligand, selected preferably from the derivatives of 2,2'-bipyridines and 1,10-phenanthrolines. The exemplary ligands L² in Table 1 are sulfonated 2,2'-bipyridine and 1,10-phenanthroline derivatives. The negatively charged group of the exemplary ligands is —$SO_3^-$. But they can be also selected from —$OSO_3^-$, —$PO_3H^-$, —$OPO_3H^-$ etc. The starting material or the intermediates during the synthesis may exist in the forms of a salt, such as a sodium salt. In addition to those listed in Table 1 and used for the syntheses of the exemplary ECL labels in the present invention, L² can be selected from, but are not limited to, the di-anionic diimine ligands below:

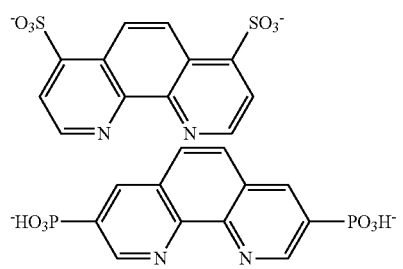

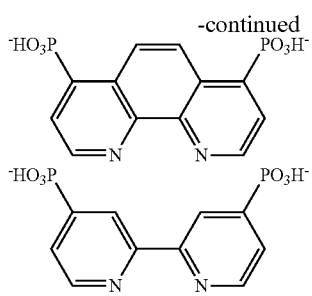

$L^3$ is a nitrogen-containing bidentate ligand without any charged group, selected preferably from 2,2'-bipyridines, 1,10-phenanthrolines and their substituted analogs. In addition to those listed in Table 1 and used for the syntheses of the exemplary ECL labels in the present invention, $L^3$ can be selected from, but are not limited to, the ligands below:

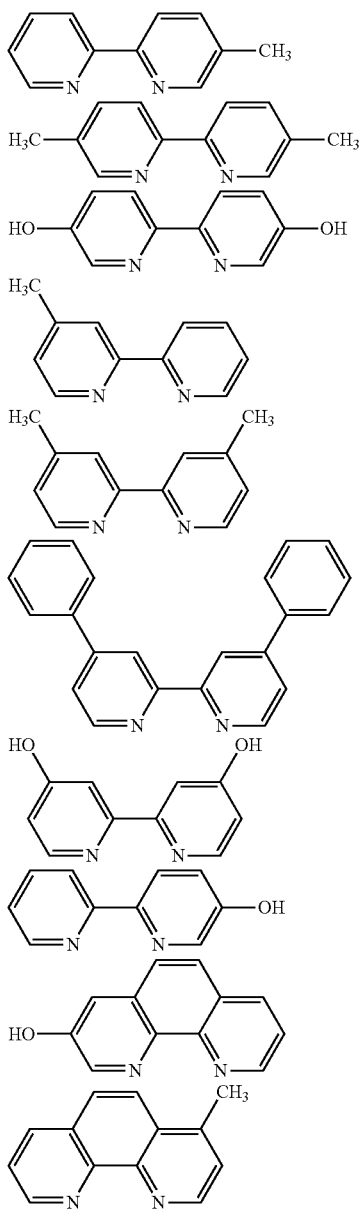

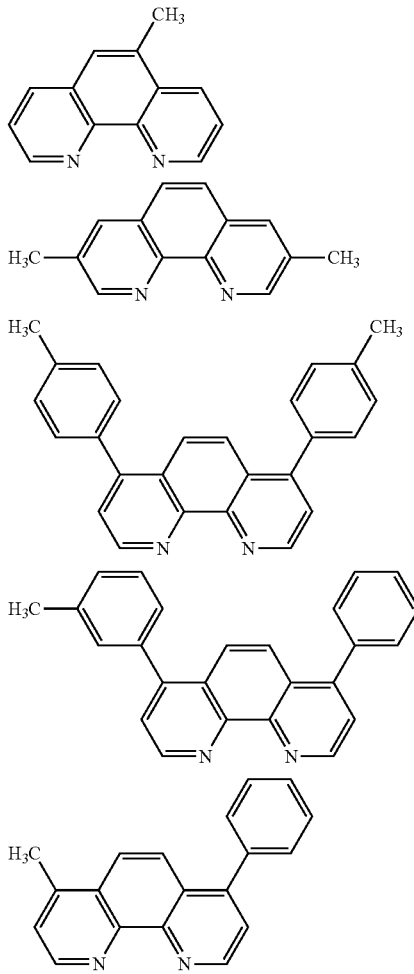

$L^4$ and $L^5$ are preferably mono-anionic nitrogen-containing heterocyclic bidentate ligands, selected preferably from the derivatives of 2,2'-bipyridines and 1,10-phenanthrolines. The exemplary ligands $L^4$ and $L^5$ in Table 1 are sulfonated 2,2'-bipyridine and 1,10-phenanthroline derivatives. The negatively charged group of the exemplary ligands is $-SO_3^-$. But they can be also selected from $-OSO_3^-$, $-PO_3H^-$, $-OPO_3H^-$ etc. The starting material or the intermediates during the synthesis may exist in the forms of a salt, such as a sodium salt. In addition to those listed in Table 1 and used for the syntheses of the exemplary ECL labels in the present invention, $L^4$ and $L^5$ can also be selected from, but are not limited to, the below illustrated mono-anionic diimine ligands:

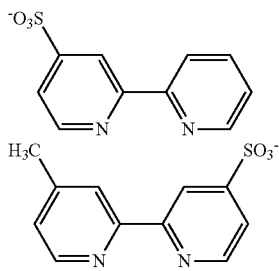

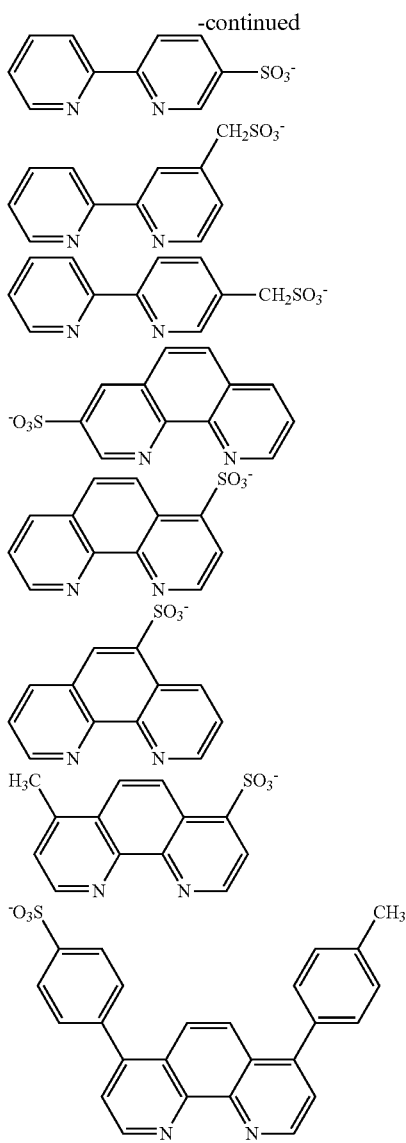

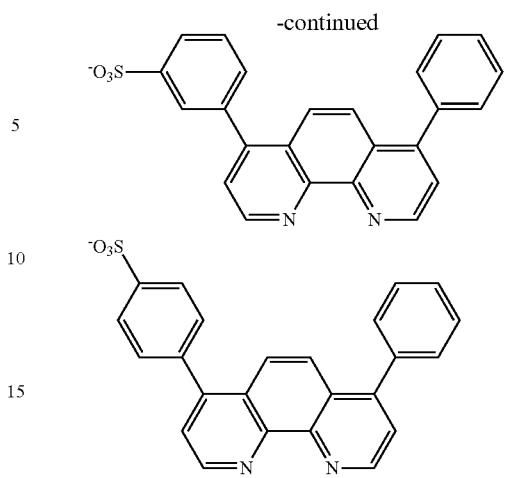

The exemplary ligands L¹ in Table 1 each have a carboxylic acid group as the bioconjugatable group. The carboxylic acid group can be easily converted into N-succinimidyl ester (NHS ester) and N-hydroxysulfosuccinimidyl ester (sulfo-NHS ester) after the polydiimine metal complex is formed. The procedures of converting carboxylic acid group into NHS ester have been detailed in publications (see e.g., M. Zhou et al, *Anal. Chem.* 2003, 75, 6708-6717) and patents (see e.g., U.S. Pat. No. 6,808,939B2). In these procedures, a coupling reagent such as N,N-dicyclohexylcarbodiimide (DCC, used in organic solvents such as methylene chloride, N,N-dimethylformamide, dimethyl sulfoxide, acetonitrile, tetrahydrofuran etc.) or 1-ethyl-3-(3-dimethylaminopropyl) carbodiimide hydrochloride (EDC, used in aqueous solutions) is generally employed.

Because of the number of ligands available as potential coordination partners at ruthenium(II) and the versatile synthetic path described above, there are many possible ligand combination modes that lead to the electronically neutral ruthenium complexes, i.e., $M^{n+}[L^1\ L^2\ L^3]^{n-}$ and $M^{n+}[L^1\ L^4\ L^5]^{n-}$. Examples of these ruthenium complexes are shown below. The syntheses of these ruthenium labels are exemplified in Examples.

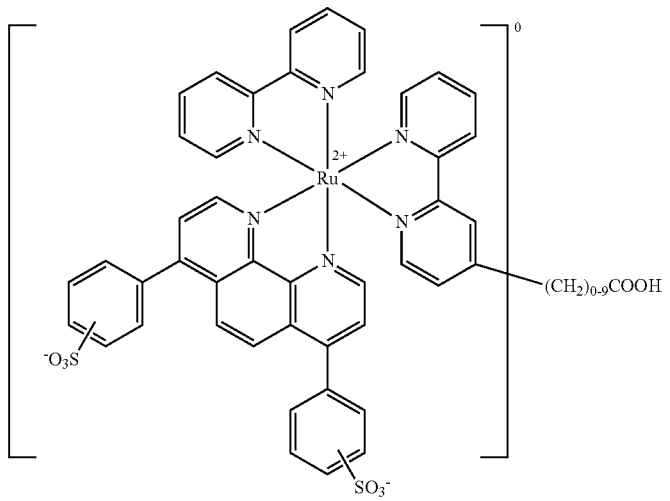

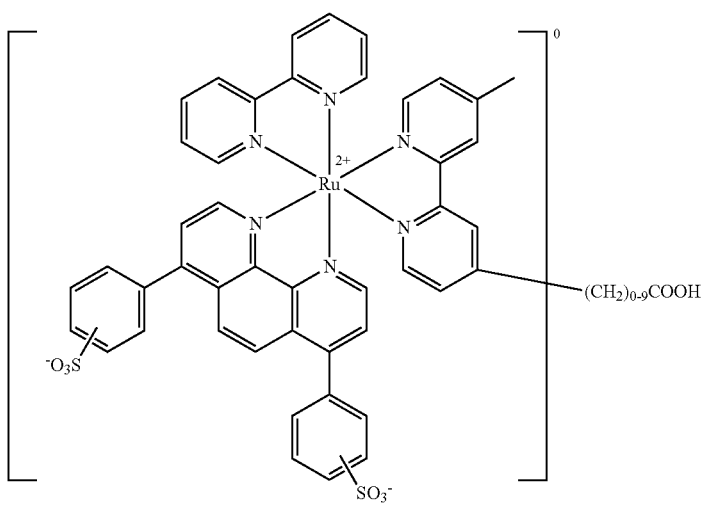
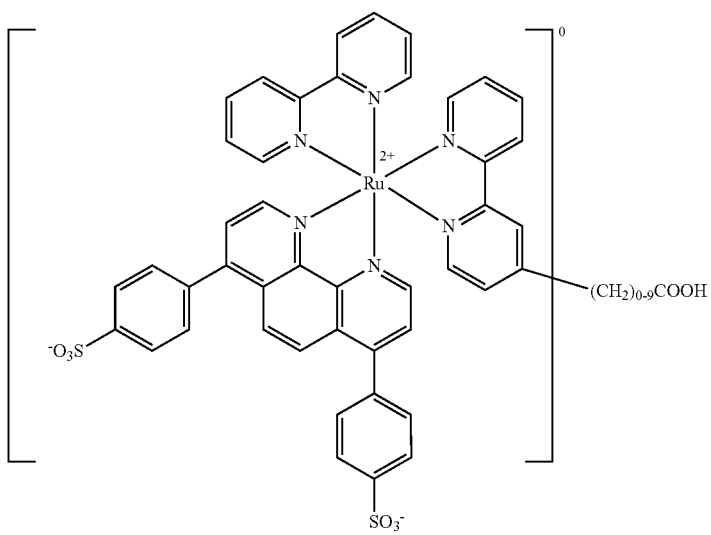
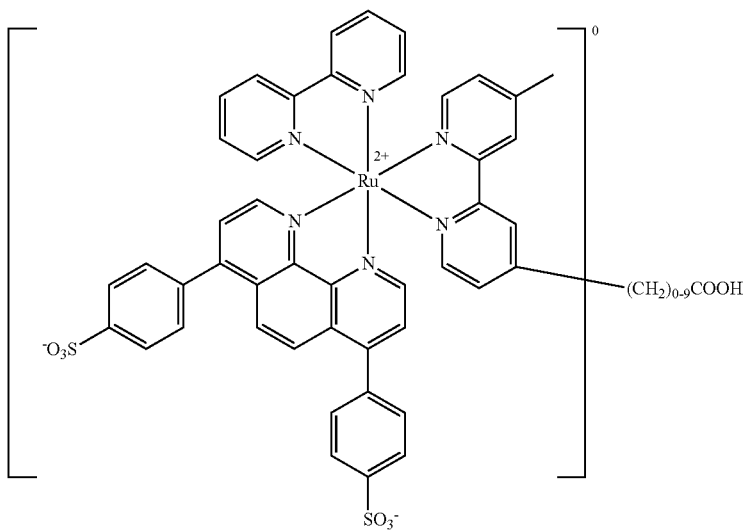

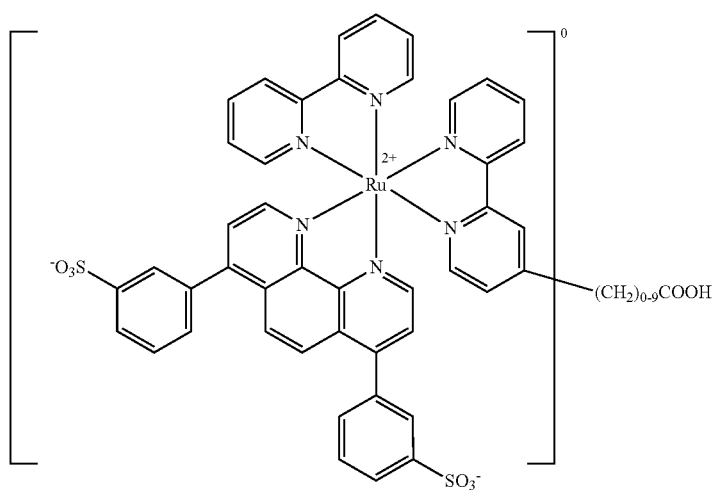
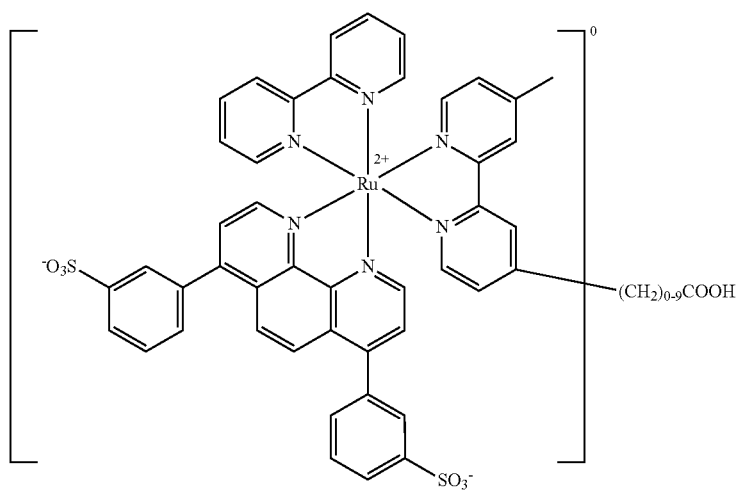
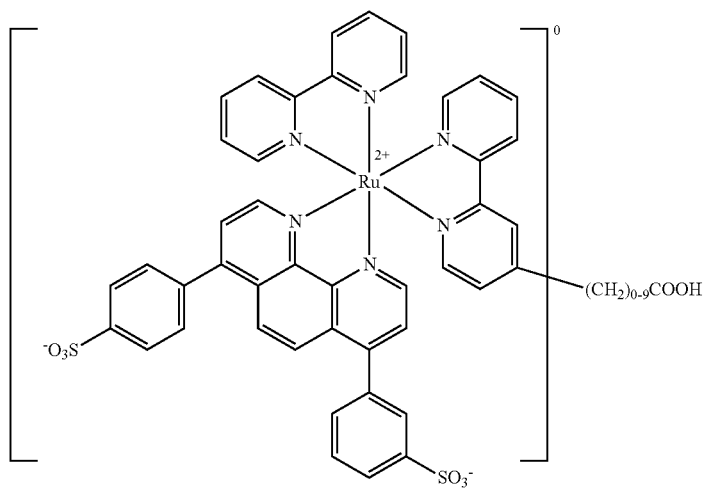

-continued
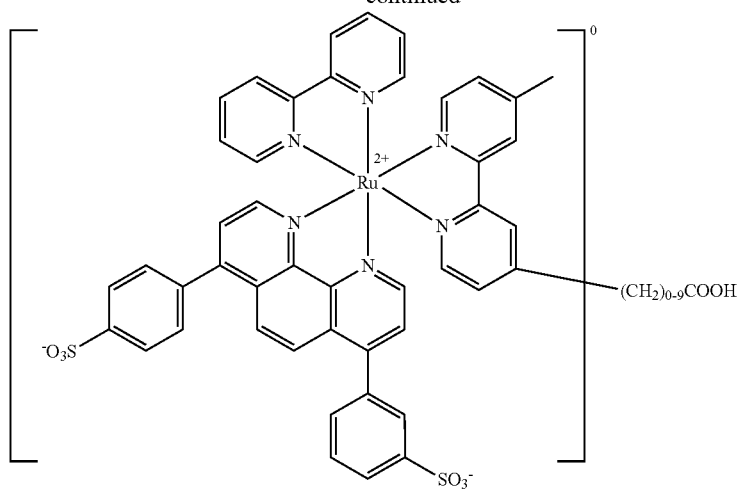
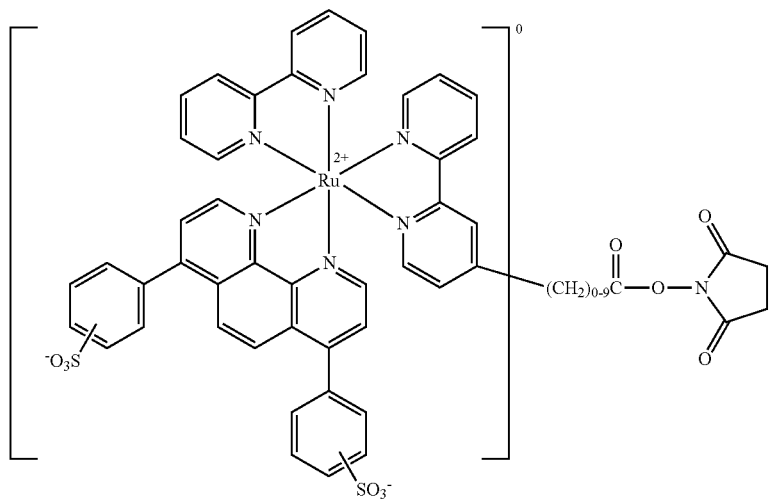
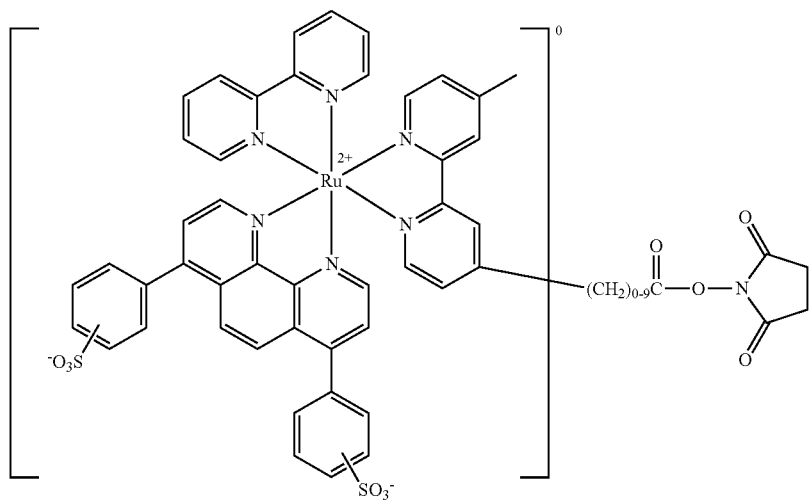

-continued
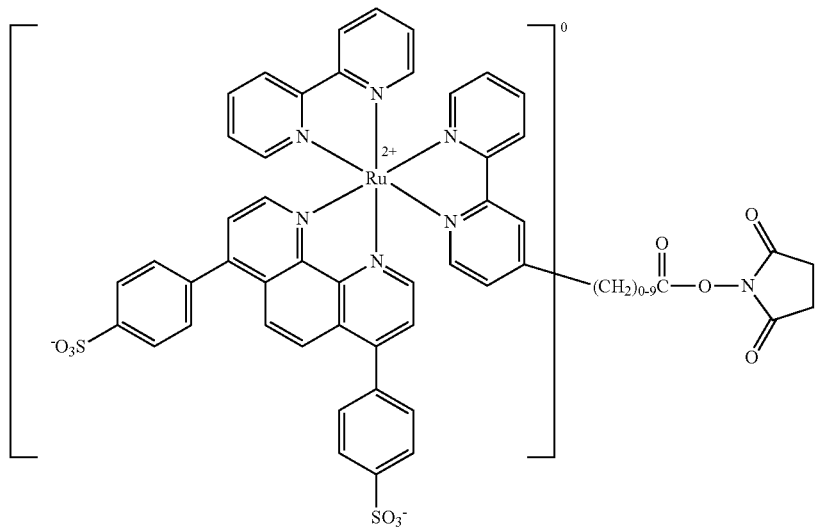
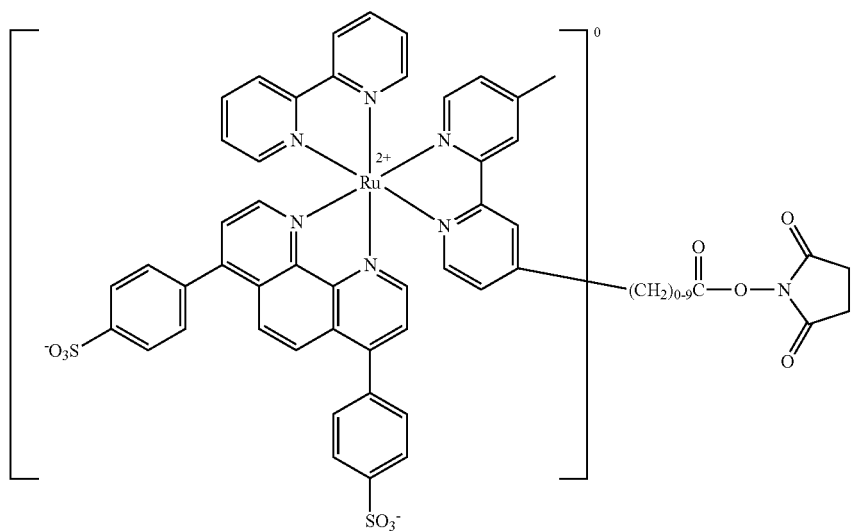
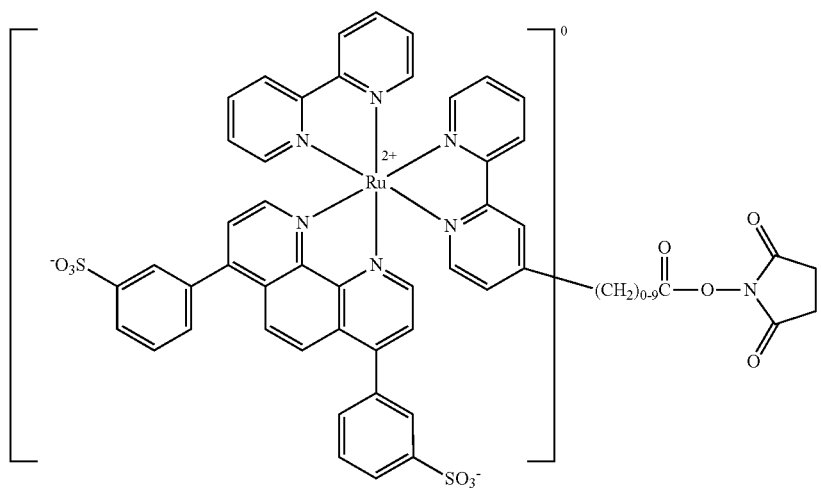

-continued
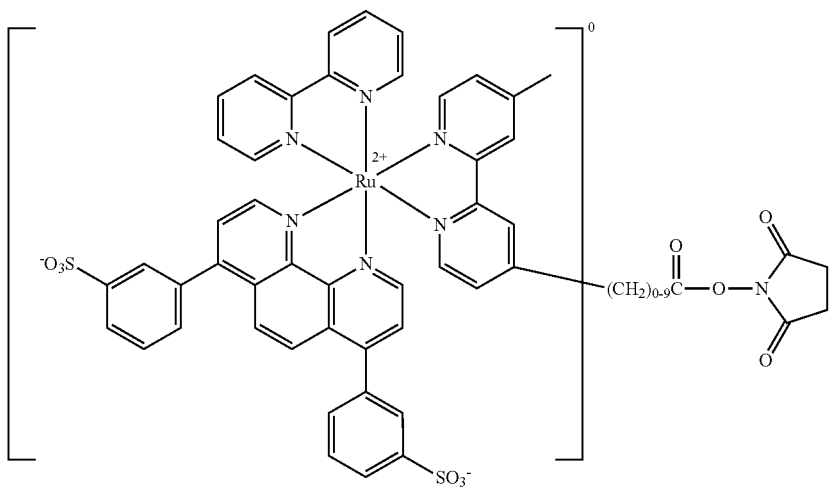
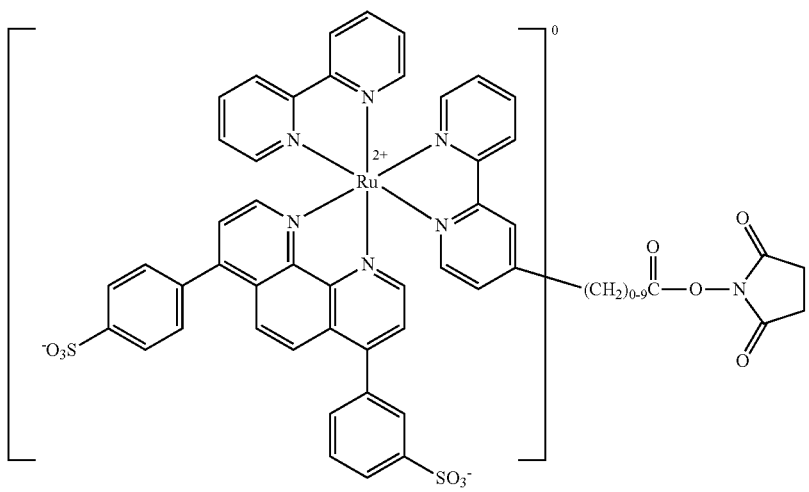
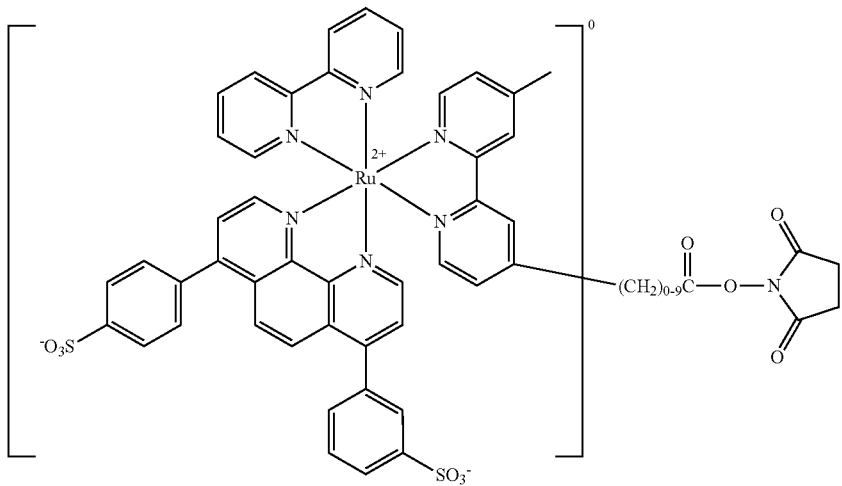

-continued
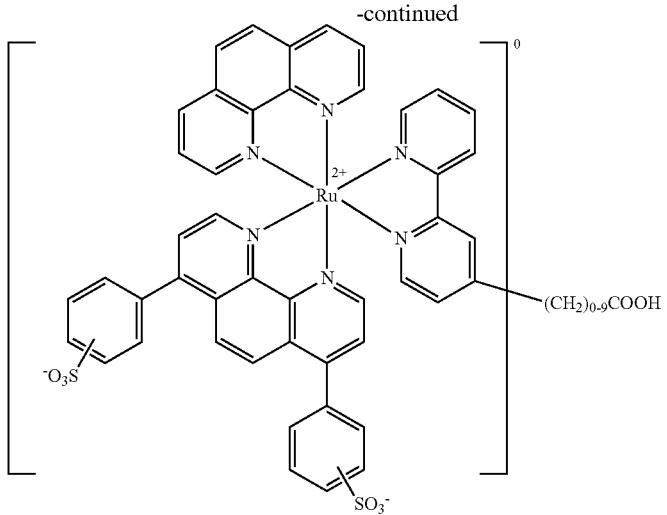
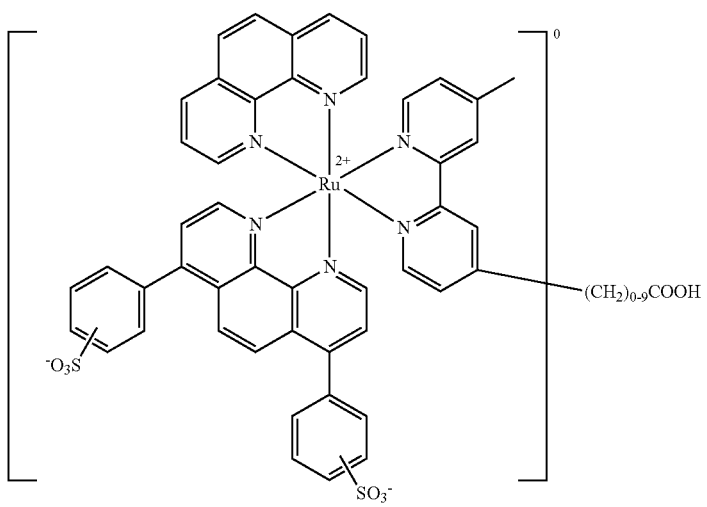
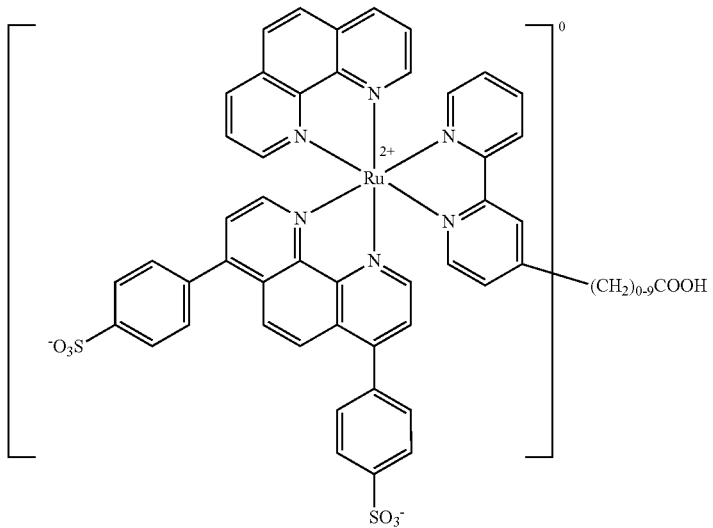

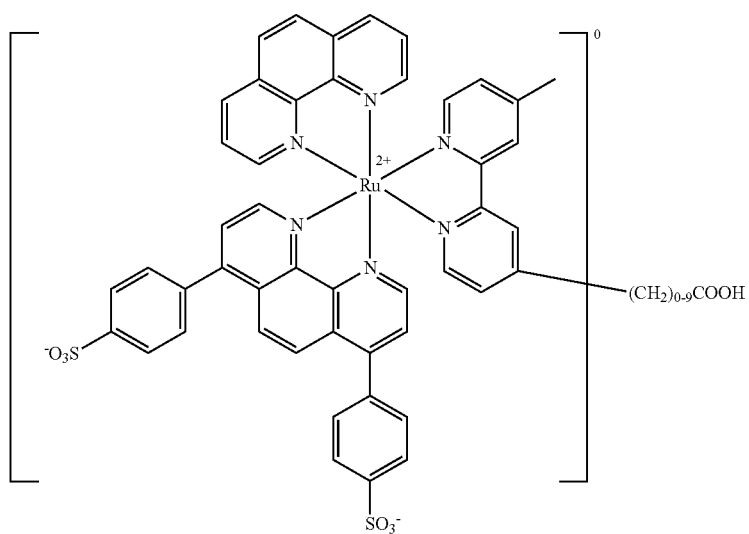
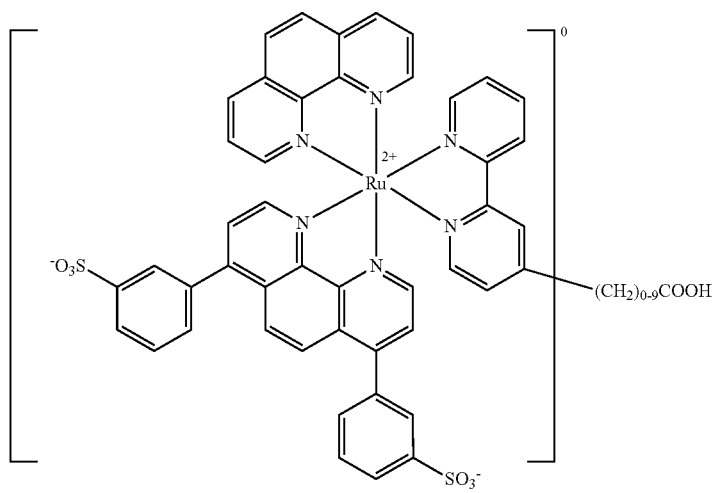
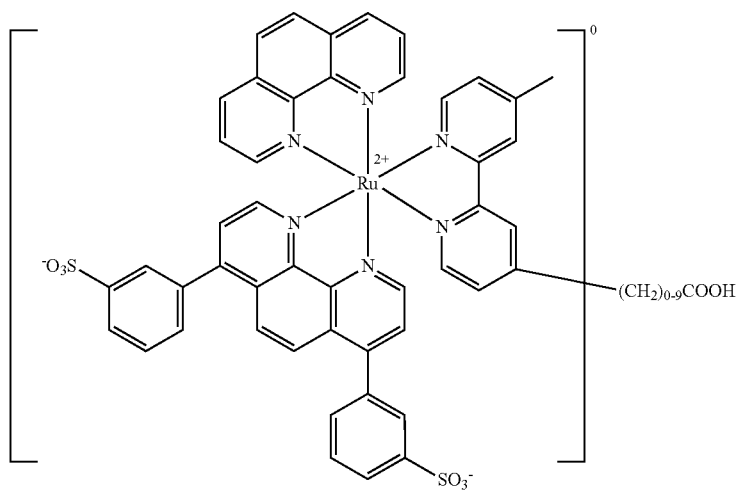

-continued
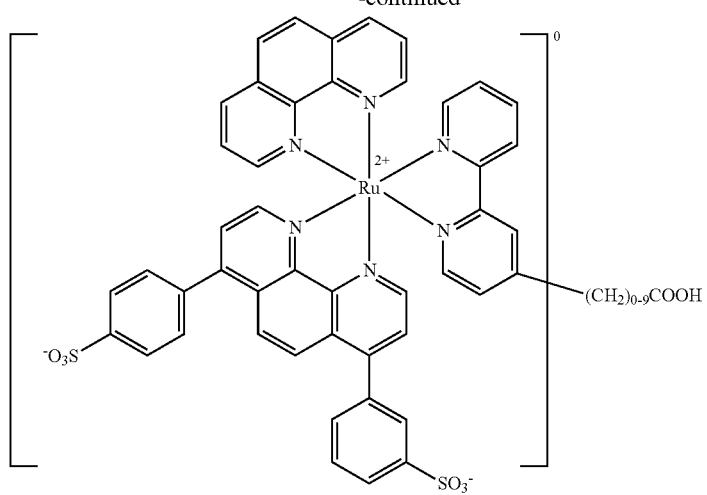
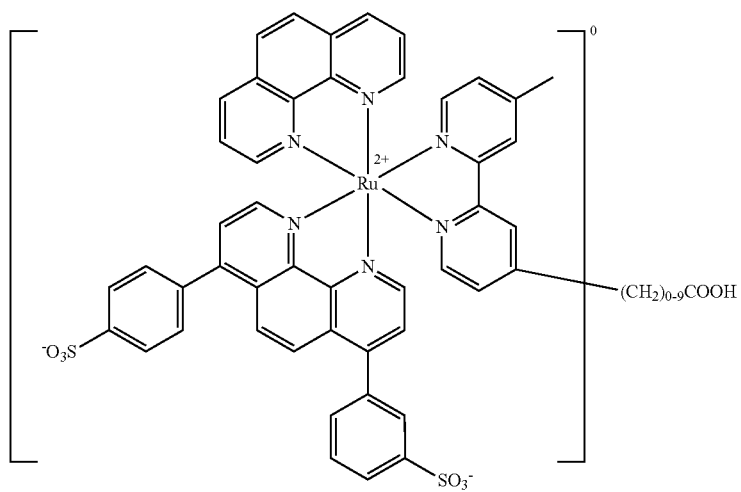
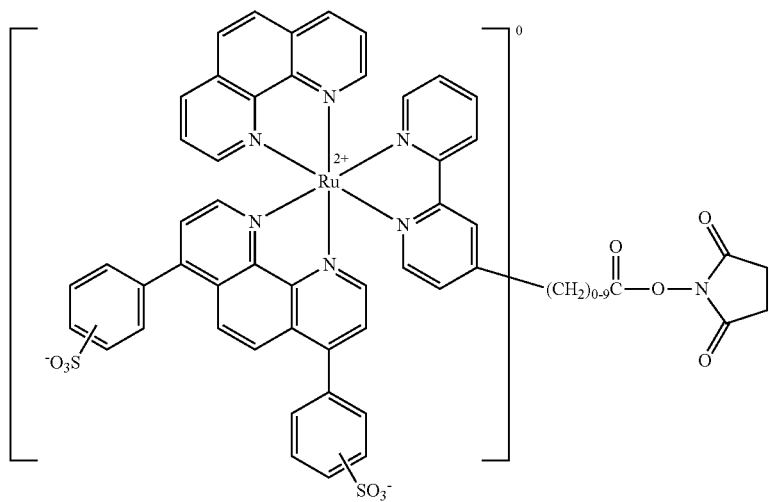

-continued
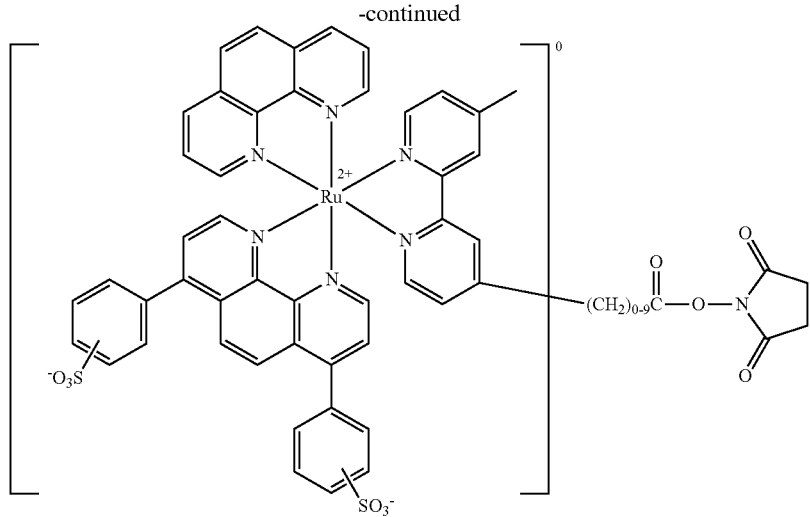
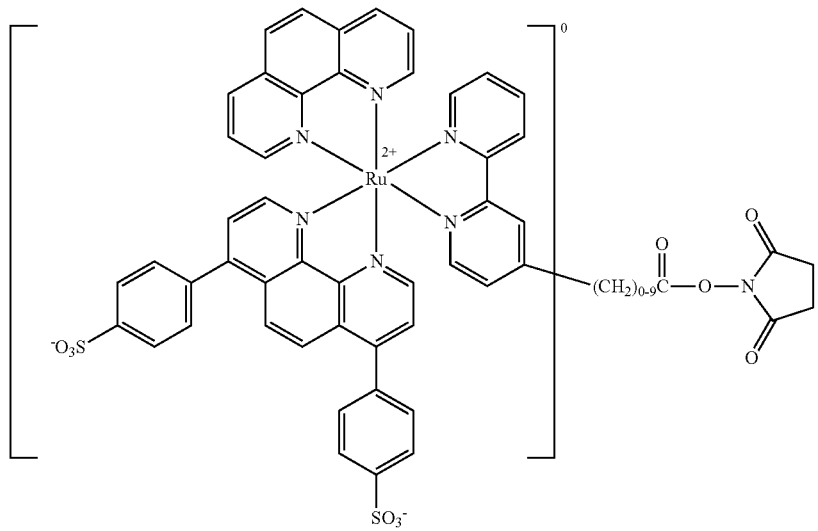
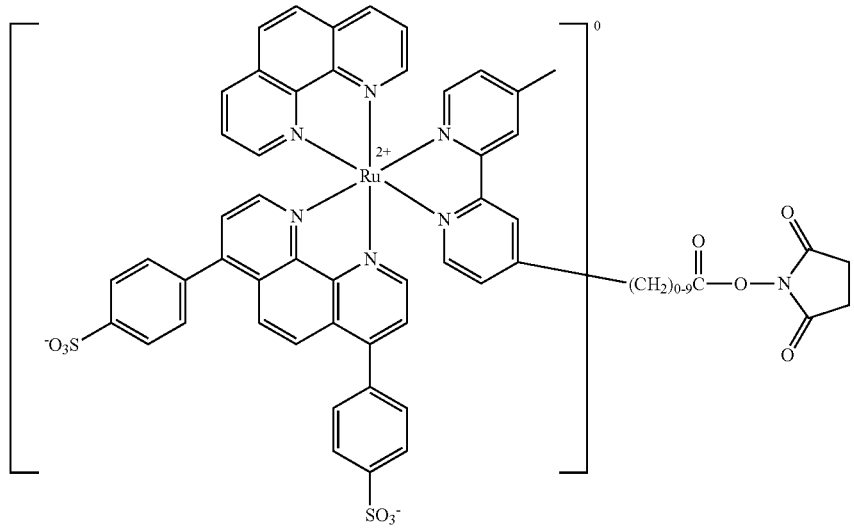

-continued
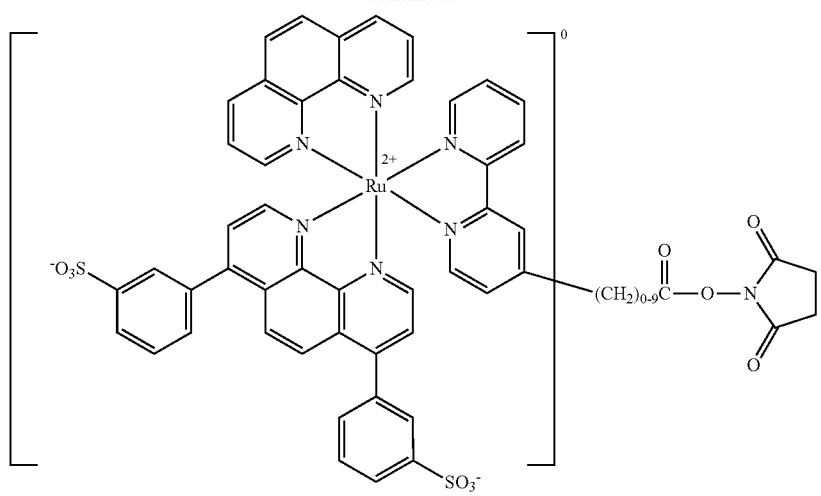
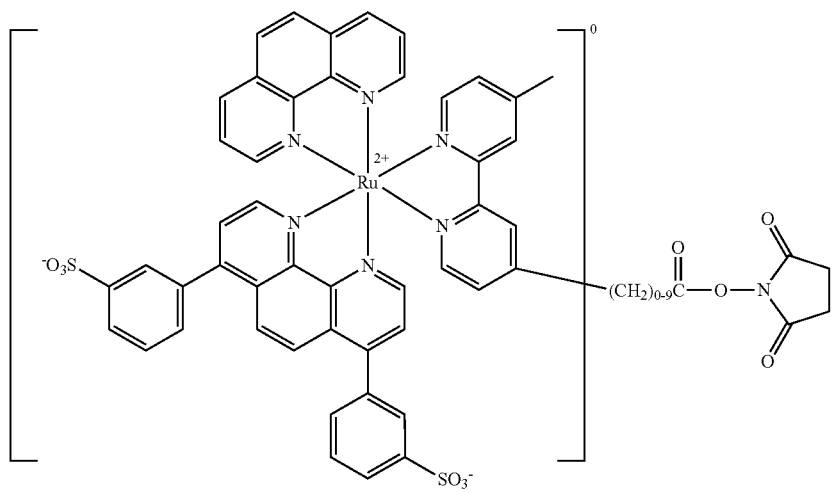
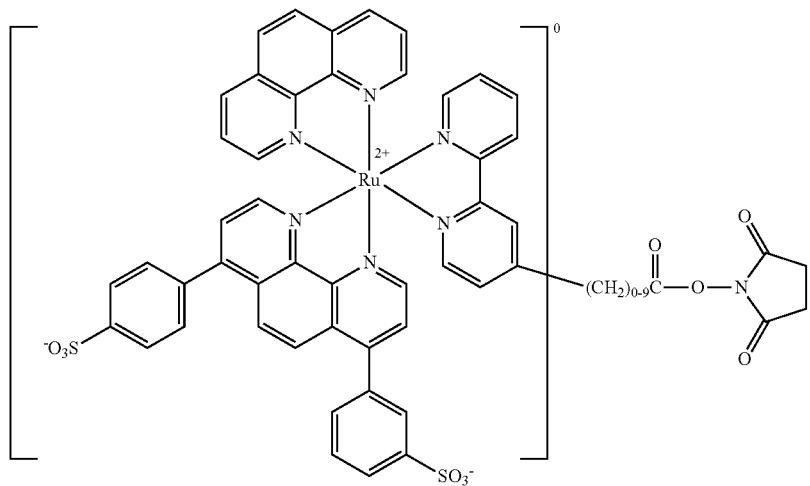

-continued
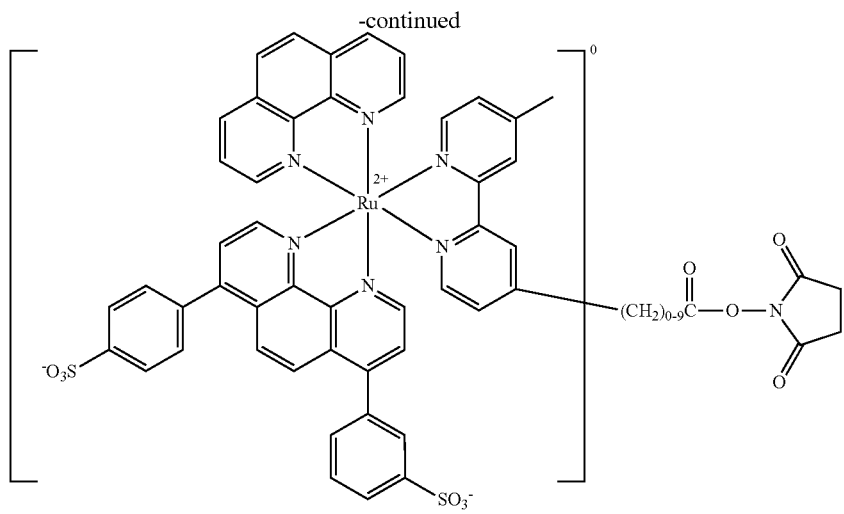
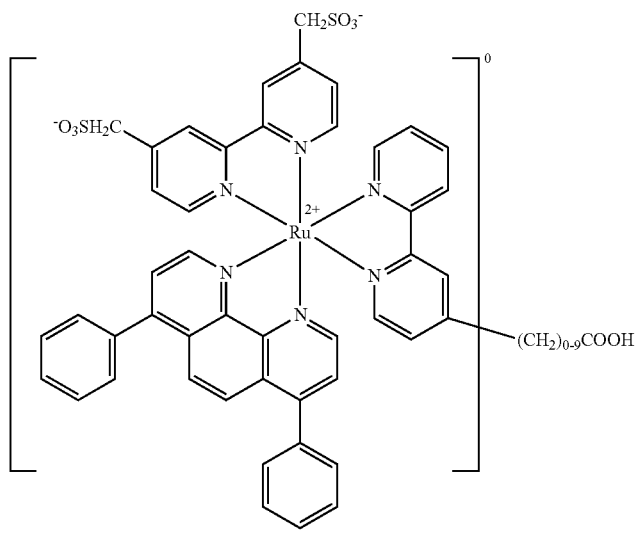
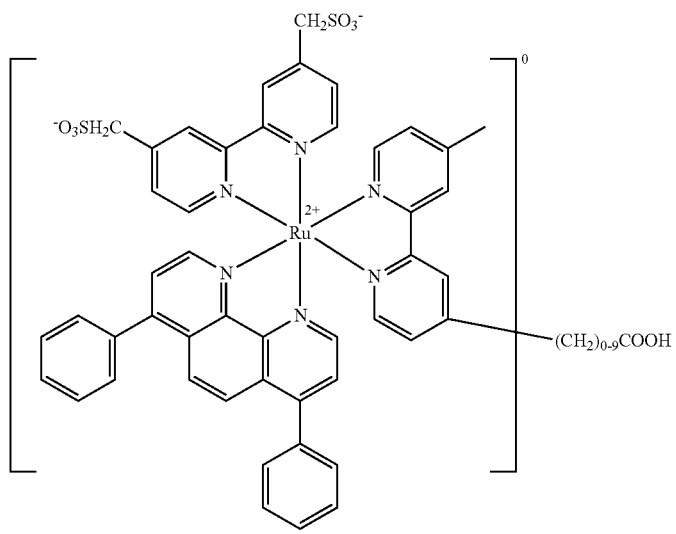

-continued
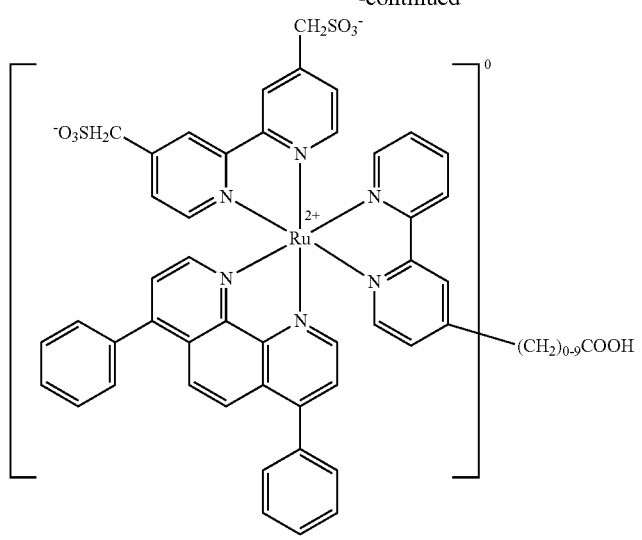
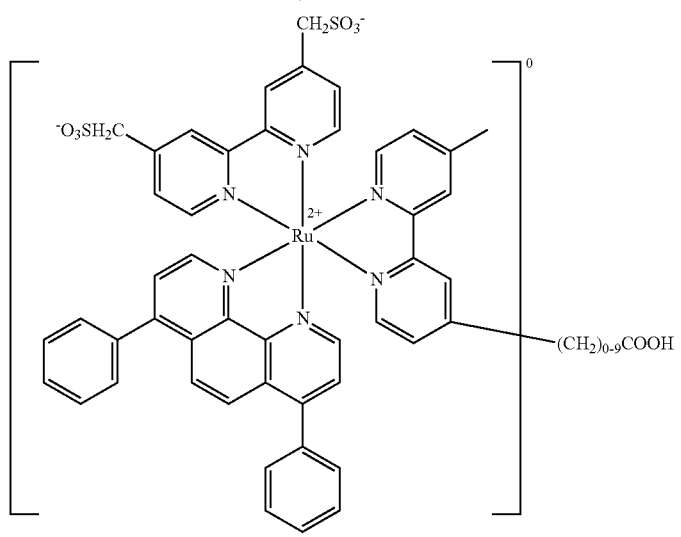
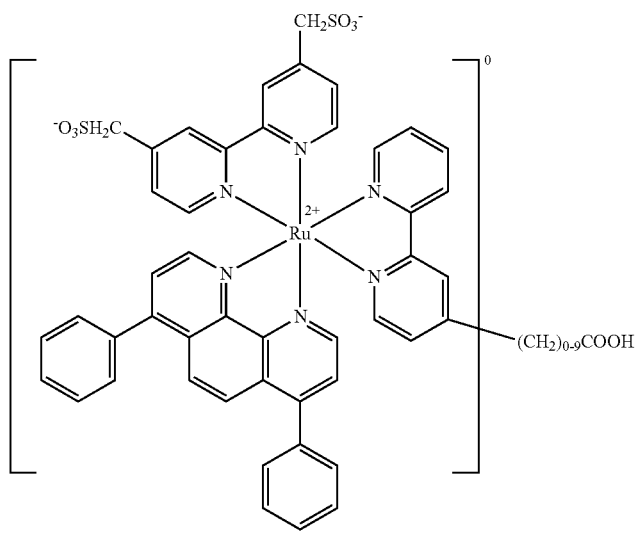

-continued
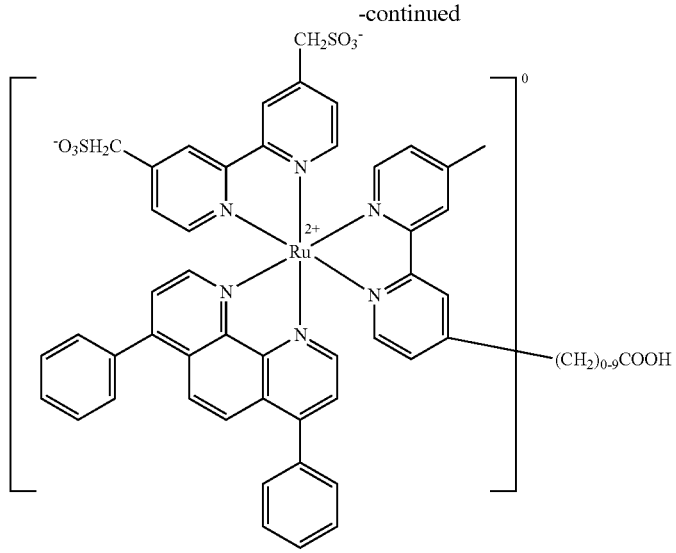
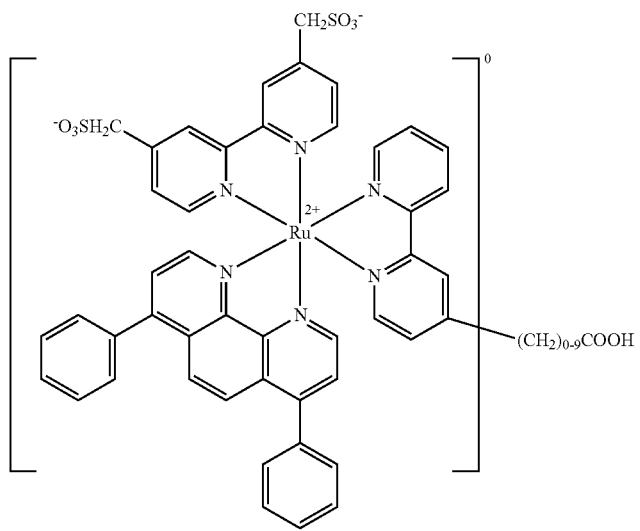
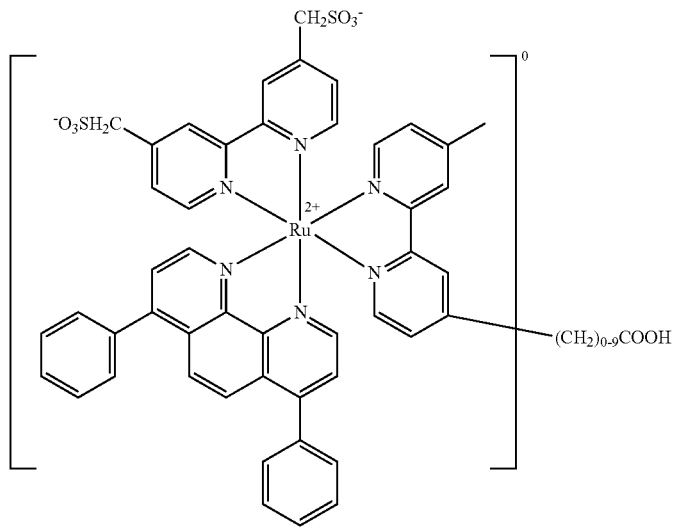

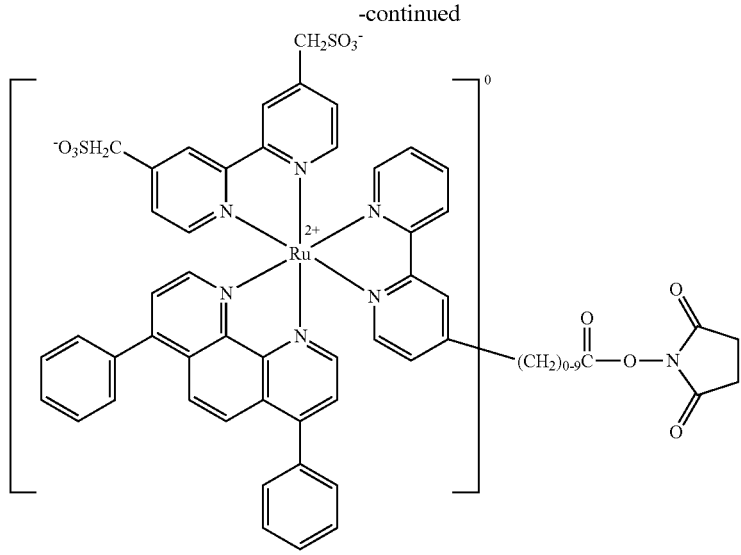
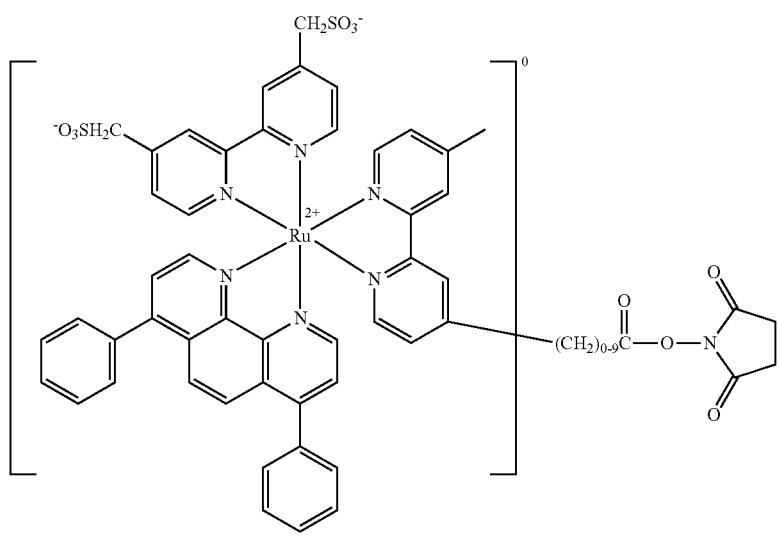
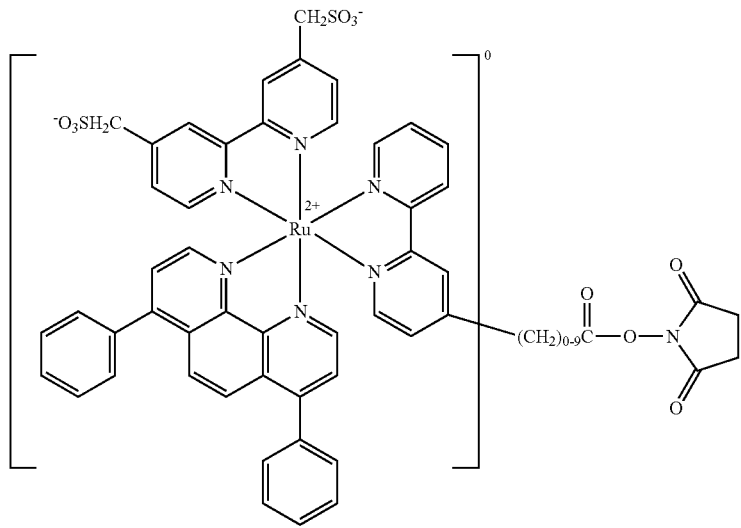

-continued
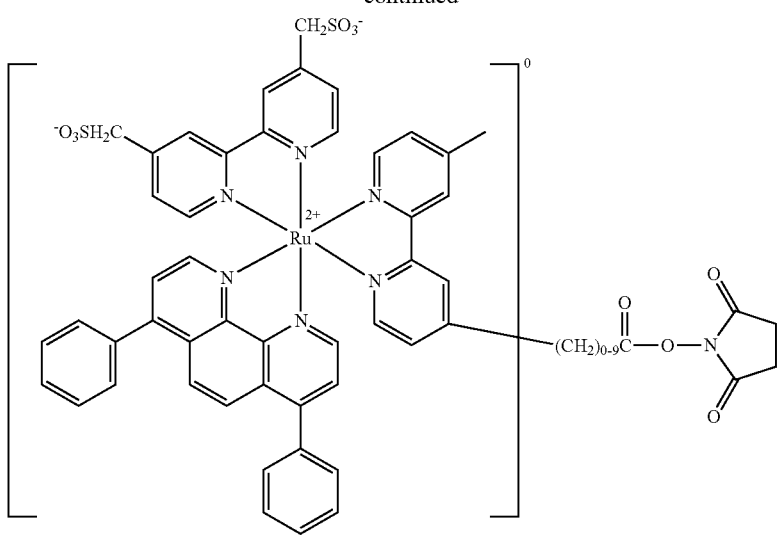
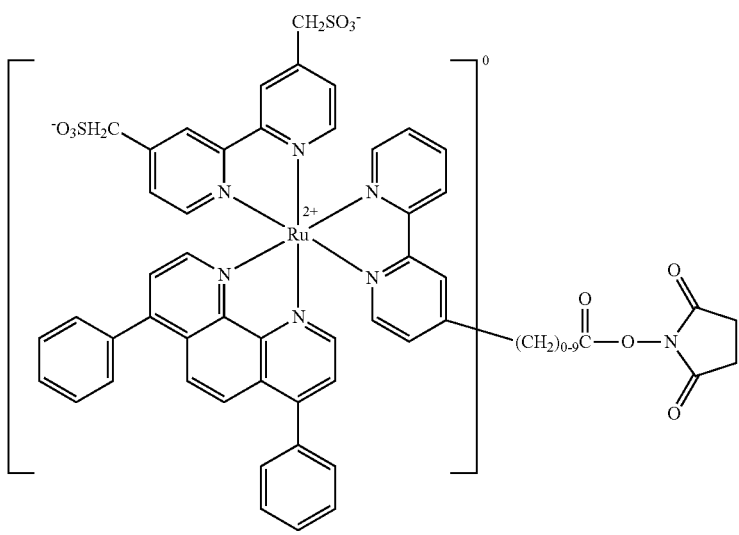
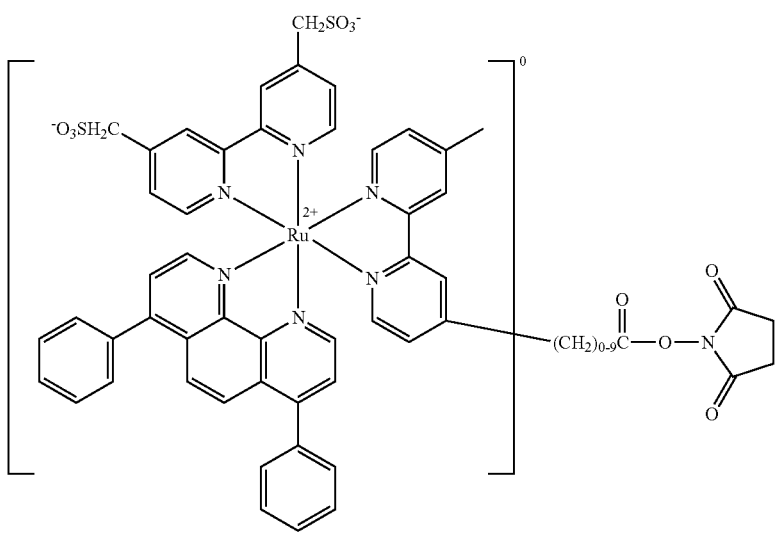

-continued
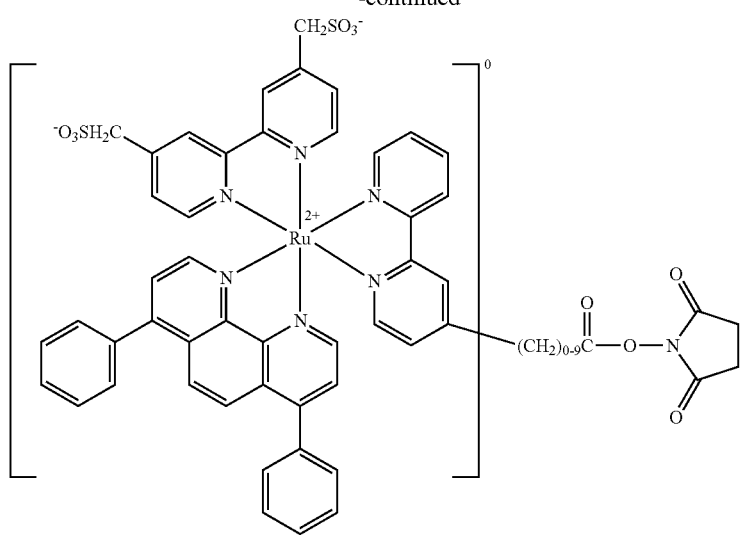
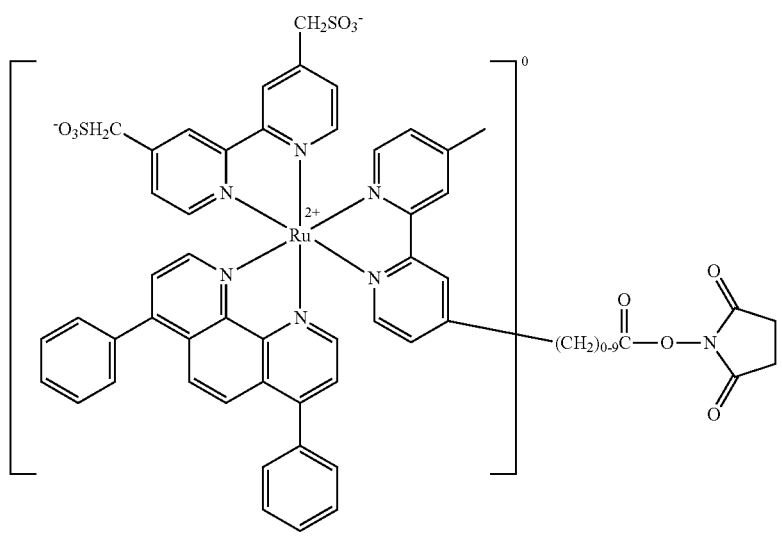
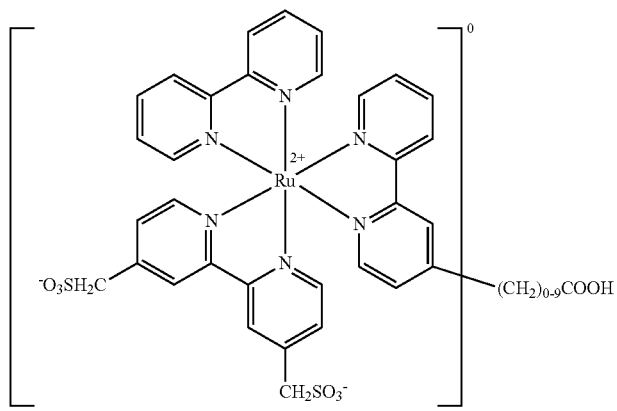

-continued
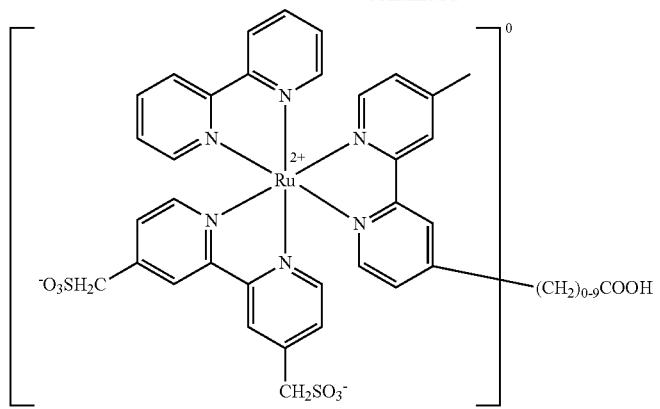
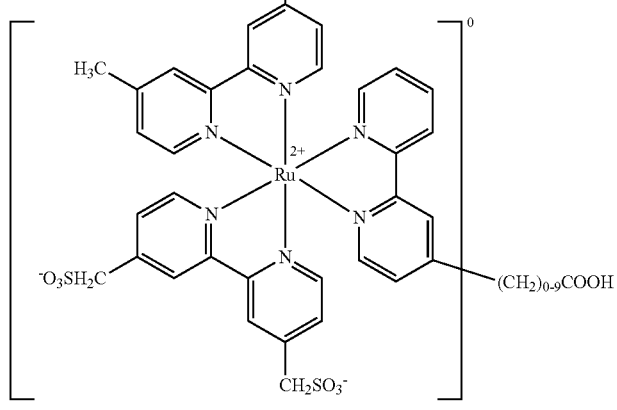
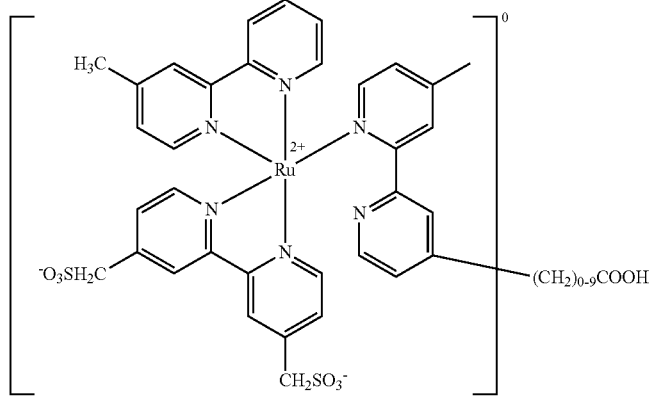
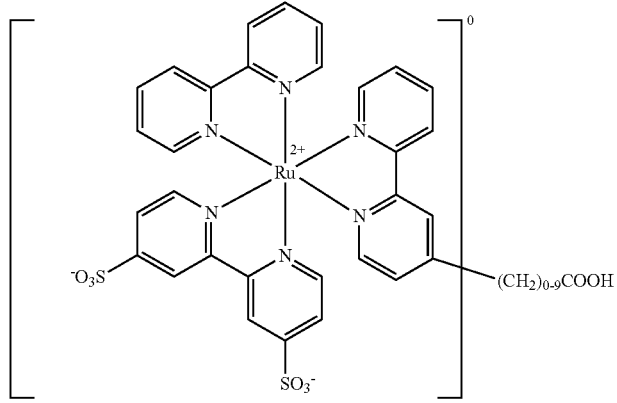

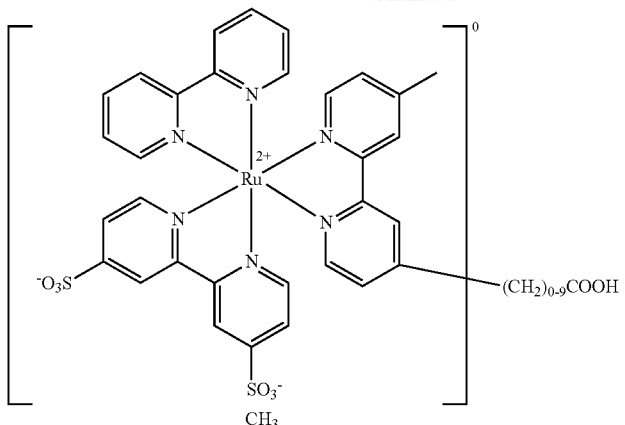
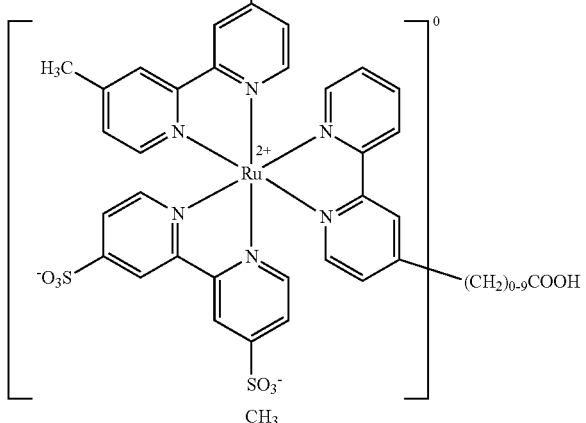
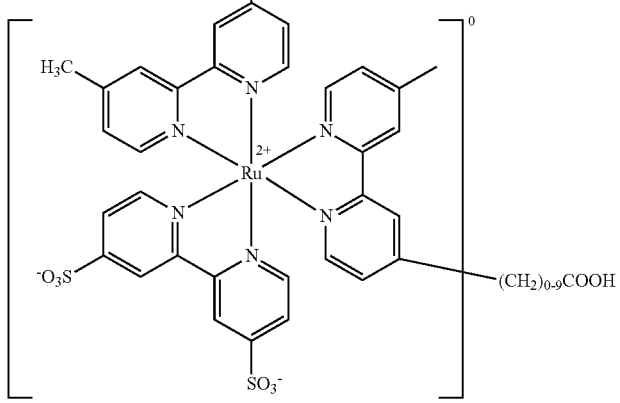
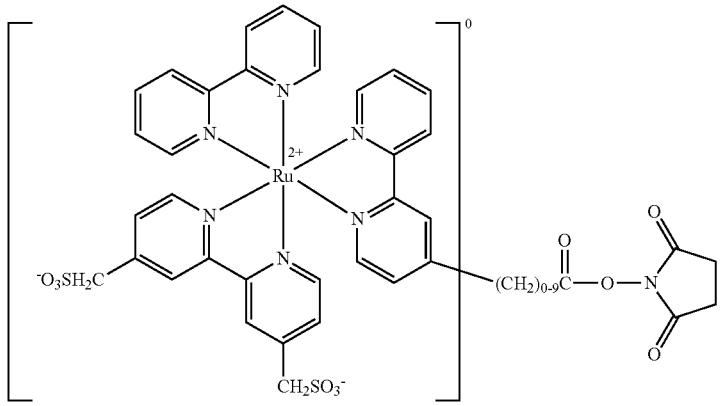

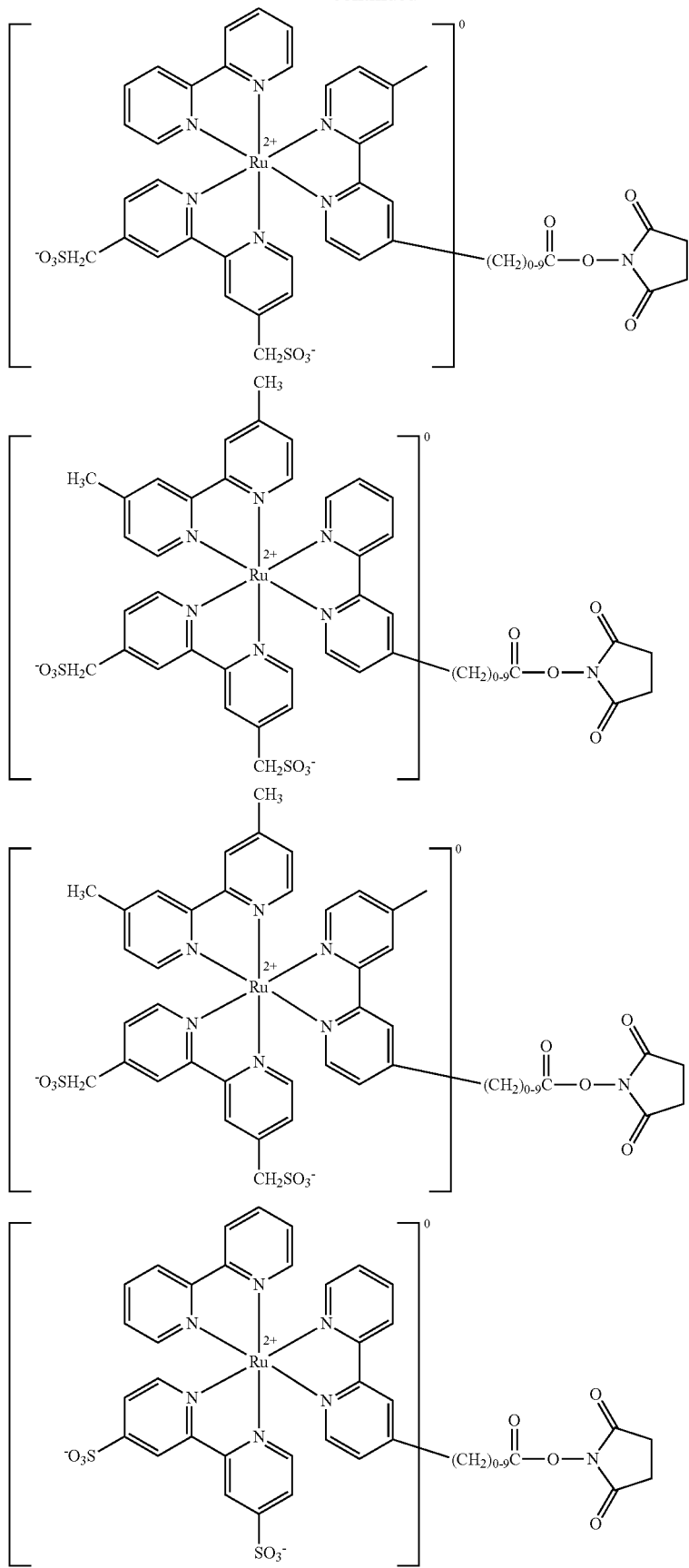

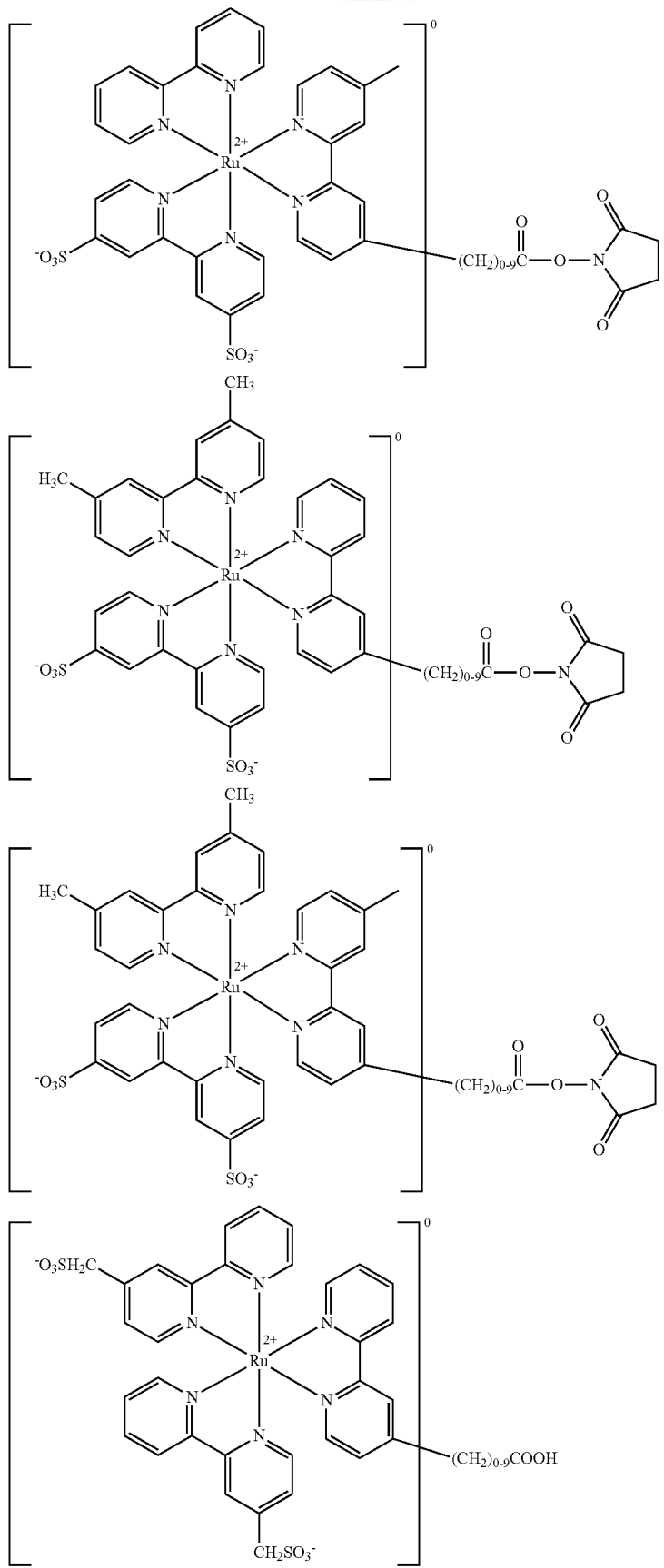

-continued
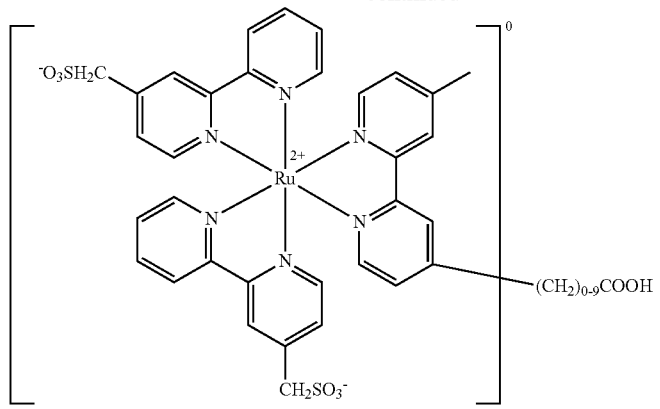
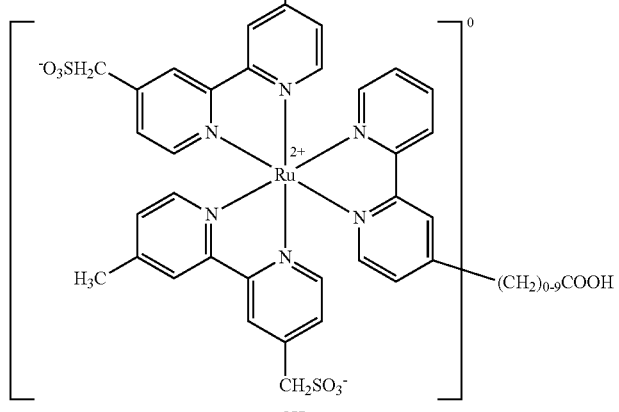
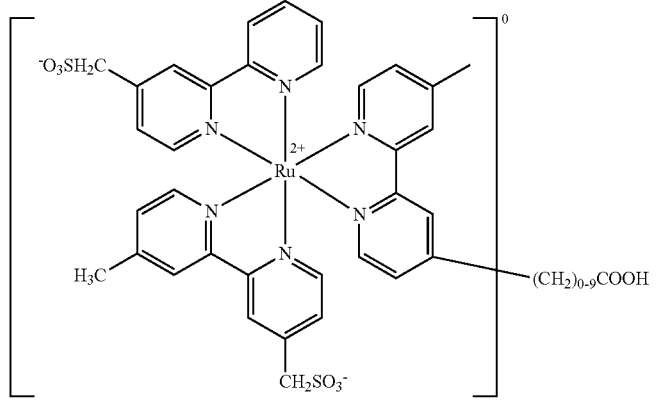
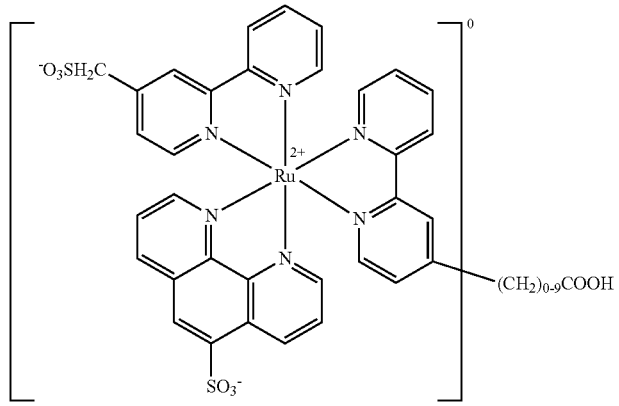

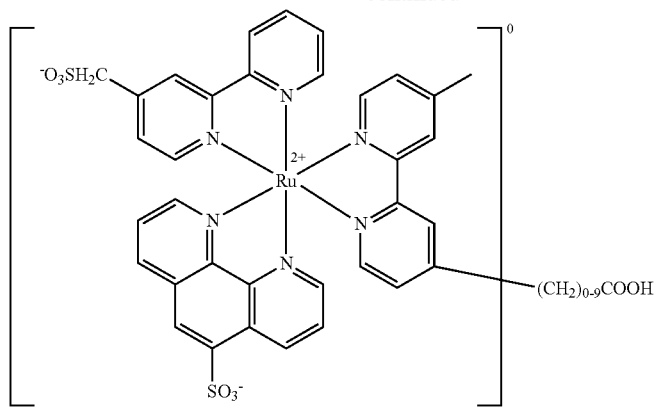
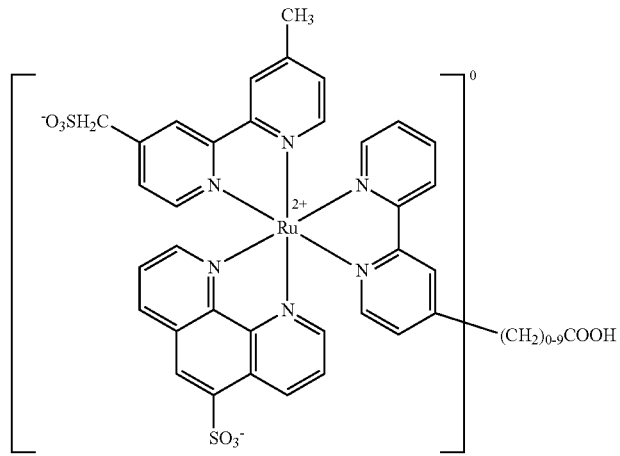
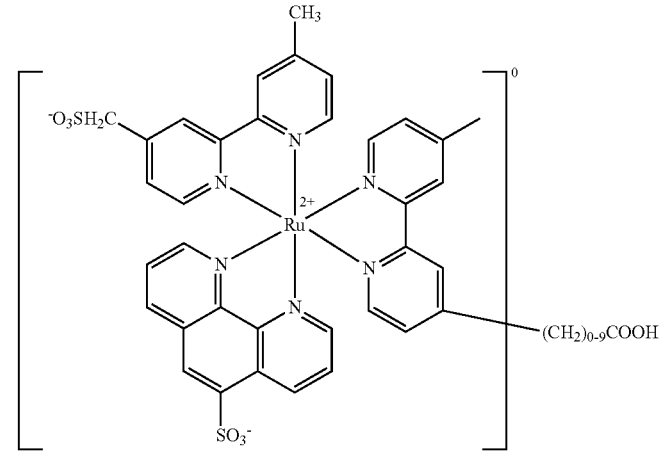
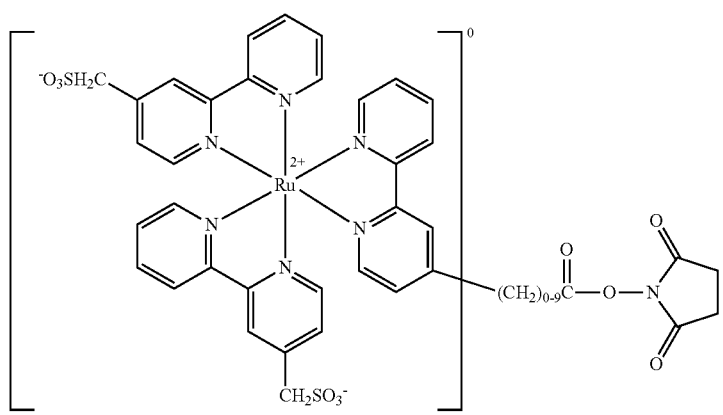

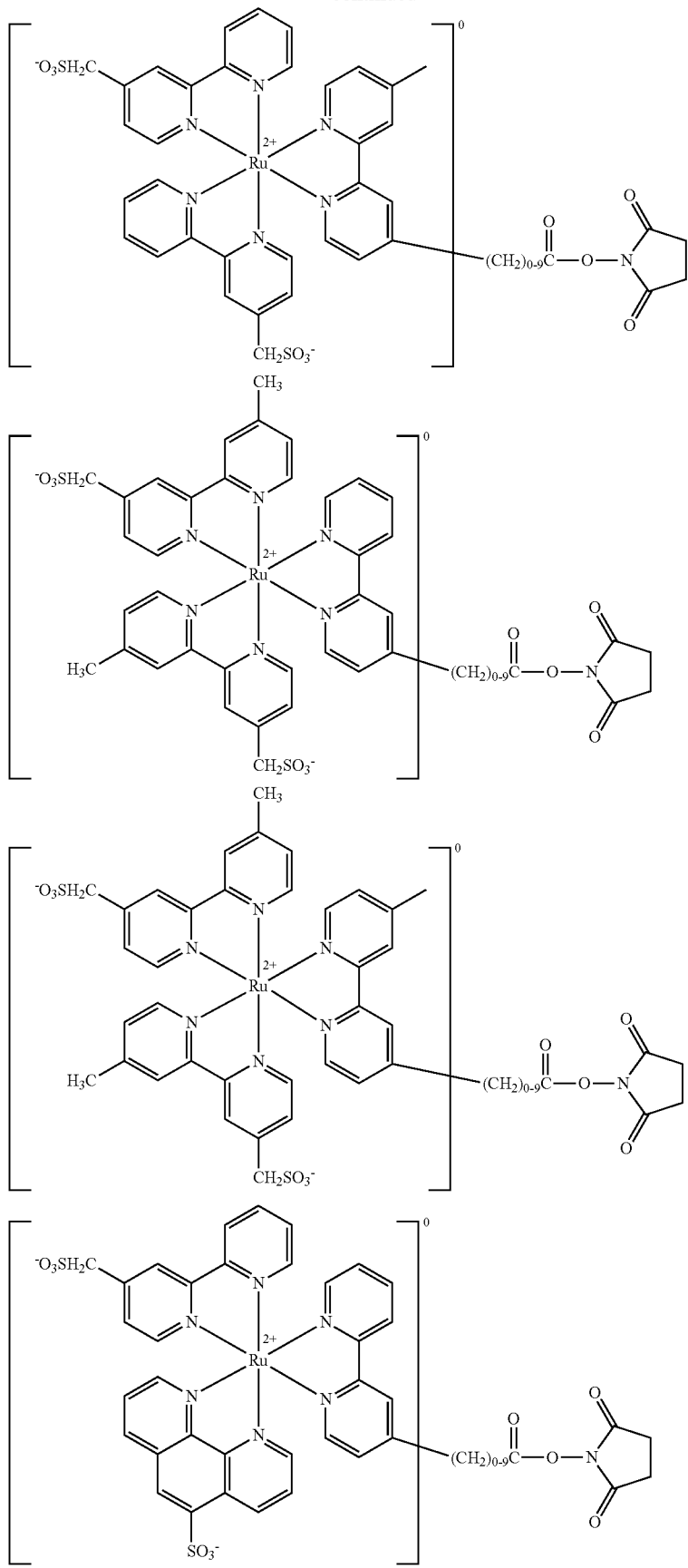

-continued

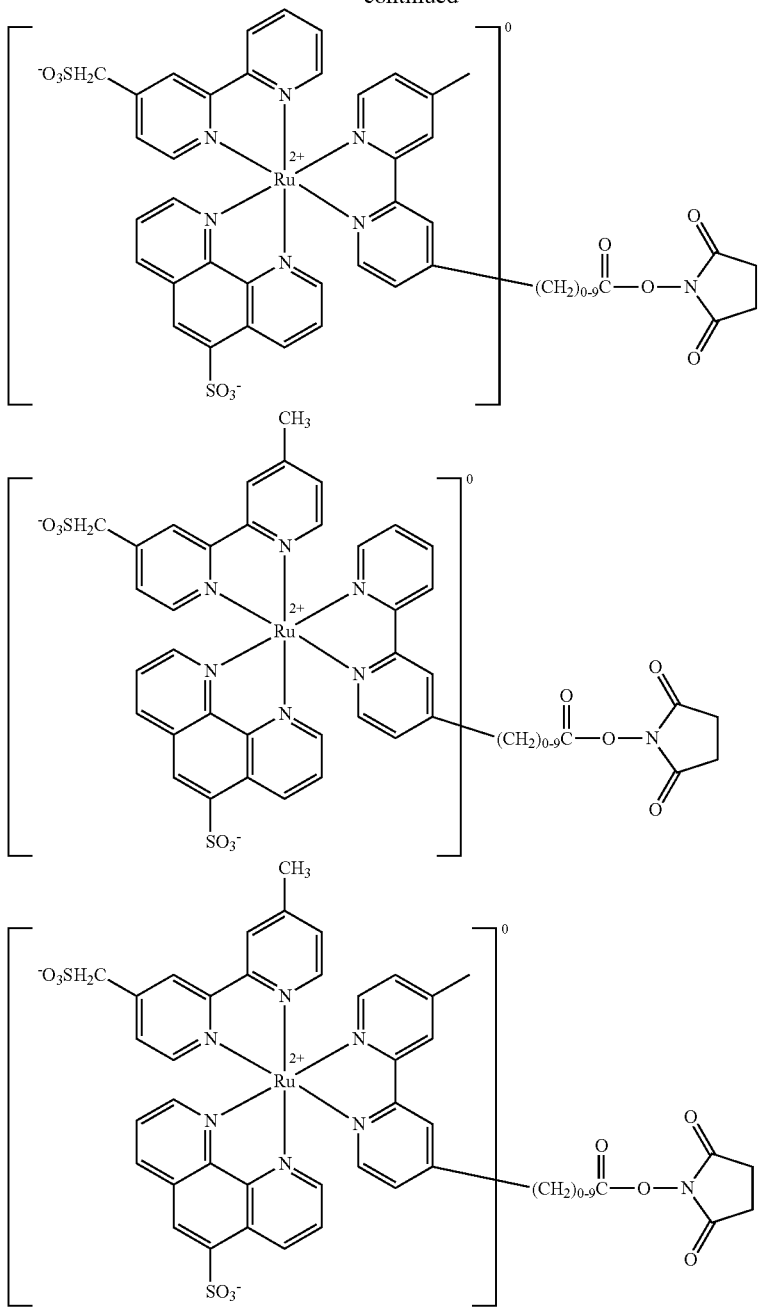

This invention further provides a labeled biological molecule by reacting an electronically neutral metal complex with the biological molecule to form a labeled biological complex having a structure:

$$\{M^{n+}[L'\ L''\ L''']^{n-}\}_m\text{-B} \quad (V),$$

$$\{M^{n+}[L^1\ L^2\ L^3]^{n-}\}_m\text{-B} \quad (VI),$$

$$\{M^{n+}[L^1\ L^4\ L^5]^{n-}\}_m\text{-B} \quad (VII), \text{ or}$$

$$\{M^{n+}[L^1\ L^4{}_2]^{n-}\}_m\text{-B} \quad (VIII)$$

B is a chemically, biochemically, or biologically active substances, selected preferably from haptens, amino acids, nucleic acids, nucleosides, nucleotides, proteins, aptamers, antibodies, and antigens etc. m is an integer equal to or larger than 1.

The labeled biological molecule is subjected to an analytical assay, wherein the analytical assay involves a measurement of luminescence emitted from the metal complexes upon photon excitation or upon electrochemical excitation. A further step includes performing an electrochemiluminescence assay, wherein the electrochemiluminescence assay is an electrochemiluminescence immune assay or an electrochemiluminescence DNA assay.

In an electrochemiluminescence assay, the electronically neutral metal complex is induced to emit light. The intensity of the emitted light or the number of photons emitted during) a set period of time is correlated to the concentration of the analyte.

EXAMPLES

Synthesis of Ligands

1. Synthesis of a 2,2-bipyridine Ligand with a Bioconjugatable Group: 4-(2,2'-bipyridin-4-yl)butanoic acid (3)

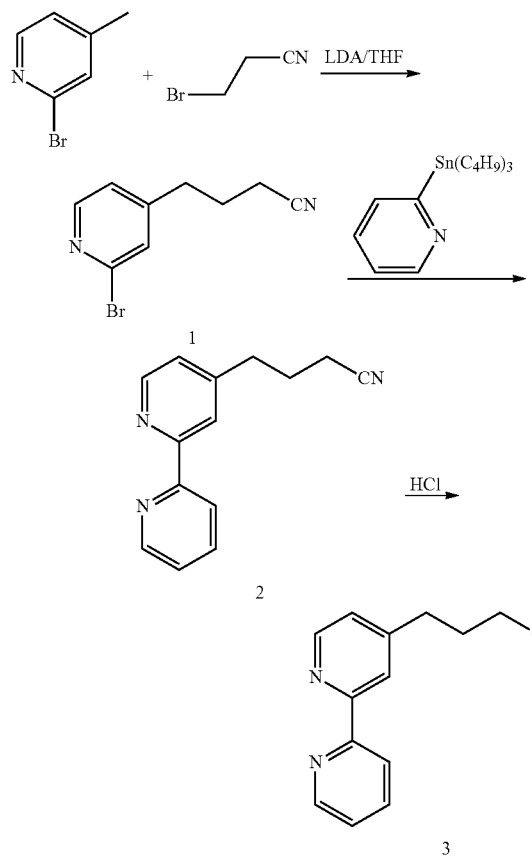

To diisopropylamine (82.8 mL, 0.59 mol) in 1.5 L anhydrous tetrahydrofuran (THF) at −78° C. was added 350 mL (0.56 mol) of 1.6 M solution of n-BuLi in hexanes and the mixture stirred 1 hour at −78° C. under the nitrogen protection. 86.6 g (0.50 mol) of 2-bromo-4-methylpyridine in 200 mL of THF was added to the LDA solution. After four hours of reaction, 75 g (0.56 mol) of 3-bromopropanenitrile dissolved in 100 mL of anhydrous THF was then dropped into the mixture and temperature was brought up to 0° C., at which temperature was the reaction allowed to continue for 24 hours. The reaction mixture was poured into 500 mL of water and neutralized with 1 molL$^{-1}$ hydrochloric acid. The product was extracted with ethyl acetate. The combined ethyl acetate was washed with saline, dried with magnesium sulfate and roto-evaporated. The crude product was column chromatographed to yield 51.5 g of 1 (yield 46%). $^1$H NMR (CDCl$_3$, 400 MHz) δ 8.30 (1H), 7.35 (1H), 7.11 (1H), 2.78 (2H), 2.40 (2H), 2.01 (2H).

18.3 g (81.3 mmol) of 1 and 30 g (81.5 mmol) of 2-(tributylstannyl)pyridine in 400 mL of toluene was bubbled with nitrogen for 10 min., followed by the addition of 5.0 g of tetrakis(triphenylphosphine). The mixture was refluxed under nitrogen for 60 hours and cooled to room temperature. The black solid was removed by filtration and the filtrate was roto-evaporated and re-dissolved in dicholoromethane. The solution was loaded on a triethylamine treated silica column and eluted with ether/ethyl acetate (1:1). After roto-evaporation, 15 g (yield 81.5%) of 2 was obtained. $^1$H NMR (CDCl$_3$, 400 MHz) δ 8.67 (1H), 8.59 (1H), 8.40 (1H), 8.26 (1H), 7.81 (1H), 7.31 (1H), 7.14 (1H), 2.85 (2H), 2.37 (2H), 2.05 (2H).

Figure 2:
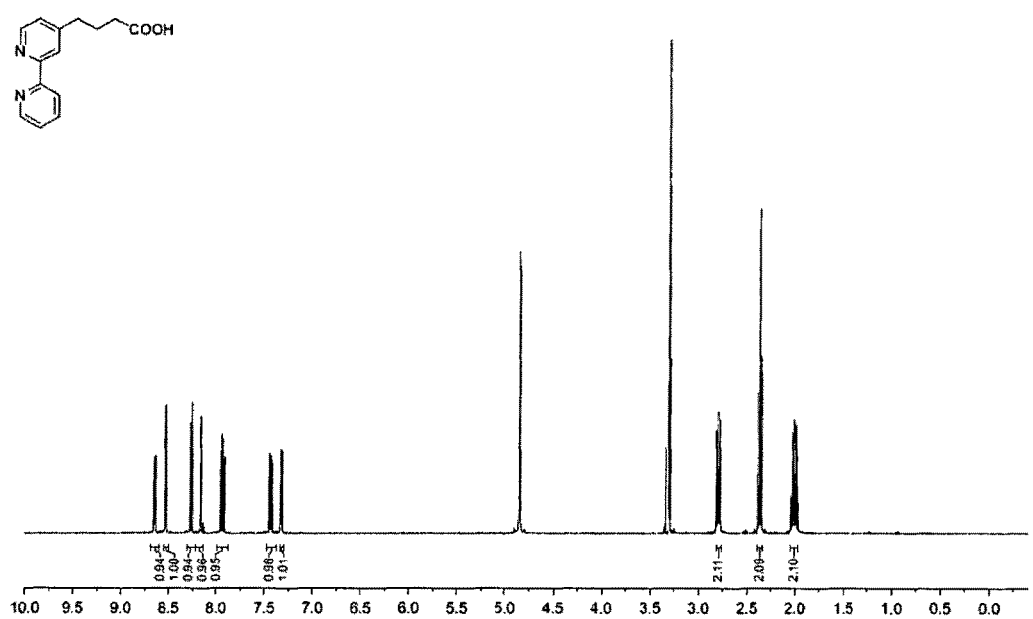
FIG. 2 is a $^1$H NMR spectrum of compound 3.

To 15 g (67.2 mmol) of 2 was added 100 mL of concentrated hydrochloric acid (12 molL-1) and refluxed for 19 hours. To the acid mixture at room temperature was added ammonia water solution to adjust the pH to 5. The product was extracted with ethyl acetate. Roto-evaporation yielded grey powder, which was redissolved in methanol and dropped into water. The white precipitate 3 was collected by filtration and dried in vacuo. Yield 10.5 g (64.5%). $^1$H NMR (CD$_3$OD, 400 MHz, See FIG. 2) δ 8.65 (1H), 8.53 (1H), 8.27 (1H), 8.17 (1H), 7.93 (1H), 7.43 (1H), 7.32 (1H), 2.79 (2H), 2.37 (2H), 2.01 (2H).

2. Synthesis of a 1,10-phenanthroline Ligand with a Bioconjugatable Group: 5-((-5-yl)amino)-5-oxopentanoic acid (4)

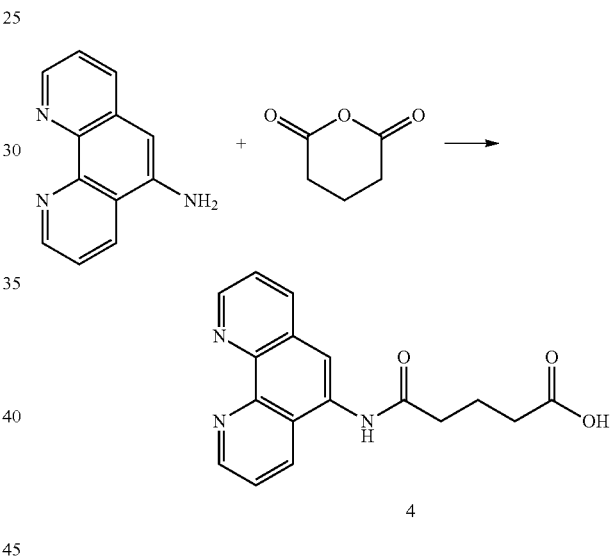

15 g (76.8 mmol) of 1,10-phenanthrolin-5-amine and 9.2 g (80 mmol) of glutaric anhydride were mixed in 150 mL of DMF. The reaction mixture was heated to 50° C. for 7 hours under nitrogen. After the reaction was complete, the solvent DMF was roto-evaporated and the residue was washed with ethyl alcohol and filtrated. The solid was grounded and washed with ethyl alcohol and subsequently dried in vacuo to afford 11 g white powder 4 (yield 46%). $^1$H NMR (400 MHz, CD$_3$OD) δ 12.13 (s, 1H),10.12 (S, 1H), 9.10-9.00 (d, J=36 Hz, 2H), 8.58 (d, 1H), 8.44-8.42 (d, J=8 Hz 1H), 8.16 (s, 1H), 7.82-7.79 (m, 1H), 7.73-7.70 (m,1H), 2.56 (m, 2H), 2.33 (m, 2H),1.94-1.86 (m, 2H).

3. Synthesis of a Mono-anionic Ligand (Salt Form): Sodium (4'-methyl-2,2'-bipyridin-4-yl)methanesulfonate (6)

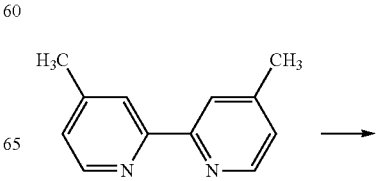

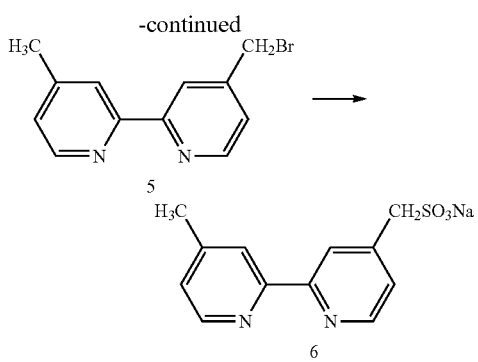

Figure 3:
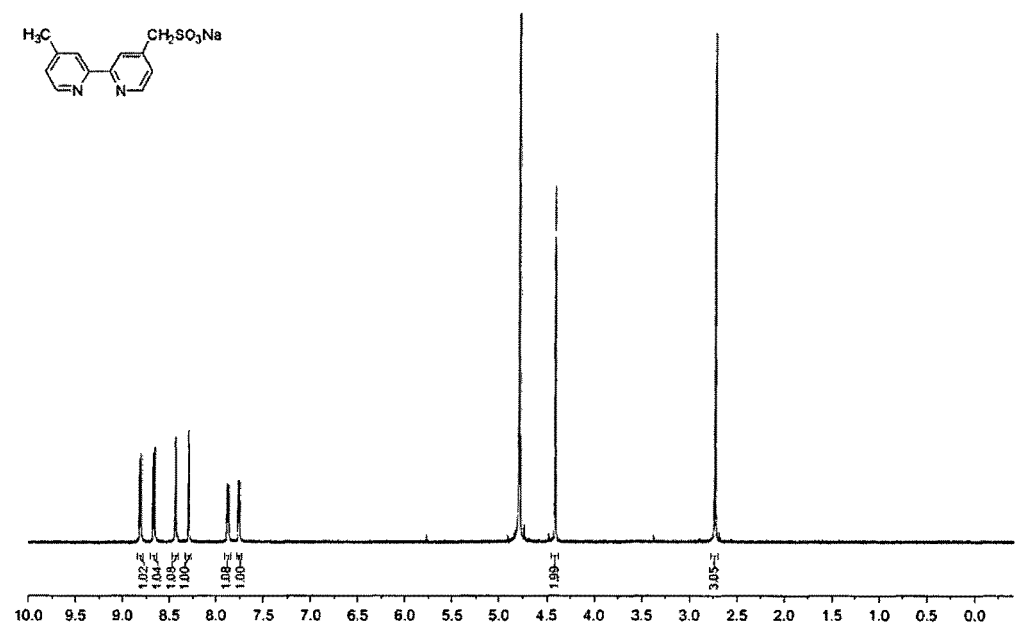
FIG. 3 is a $^1$H NMR spectrum of compound 6.

To 4,4'-dimethyl-2,2'-bipyridine (20 g, 108.5 mmol) in 400 mL of anhydrous tetrachloromethane was added 19 g (106.8 mmol) of N-Bromosuccinimide and 2.6 g of benzoyl peroxide. The mixture was refluxed overnight and cooled to room temperature. The solid was removed by filtration and the filtrate concentrated by rotary-evaporation. The column chromatography with triethylamine treated silica column afforded 6 g of 4-(bromomethyl)-4'-methyl-2,2'-bipyridine (5), which was mixed with 4.9 g (38.9 mmol) of $Na_2SO_3$ in 100 mL of water. The cloudy mixture was refluxed for six hours. When it was still hot, the supernatant was concentrated to about 30 mL and cooled to room temperature. The yellow precipitate was collected by filtration and washed with dichloromethane to afford 3.6 g of 4'-methyl-2,2'-bipyridin-4-yl)methanesulfonate (6). $^1$H NMR ($D_2O$, 400 MHz, See FIG. 3) δ 8.81 (1H), 8.67 (1H), 8.44 (1H), 8.30 (1H), 7.88 (1H), 7.76 (1H), 4.42 (2H), 2.73 (3H).

4. Synthesis of Another Mono-anionic Ligand (Salt Form)—Sodium (4'-(hydroxymethyl)-[2,2'-bipyridin]-4-yl)methanesulfonate (8)

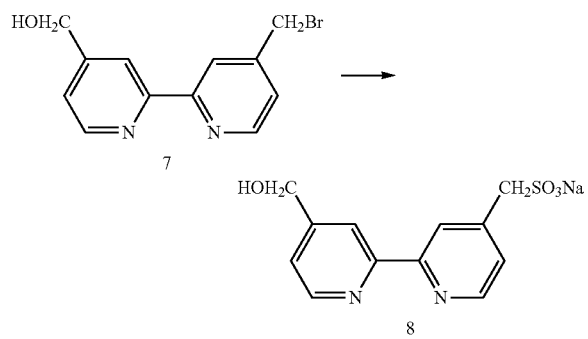

3.0 g (23.8 mmol) of $Na_2SO_3$ and 3.9 g (13.97 mmol) of compound 7, which is a by-product from the preparation of 4,4'-bis(bromomethyl)-2,2'-bipyridine from [2,2'-bipyridine]-4,4'-diyldimethanol, was mixed in 35 mL of water. The mixture was refluxed for 5 hours under nitrogen. The solution was roto-evaporated and the solid was dissolved in 10% methanol water solution. Chromatography over silica gel afforded 4.1 g of light pink product. Yield 97%. $^1$H NMR ($D_2O$, 400 MHz) δ 8.53 (1H), 8.48 (1H), 7.92 (1H), 7.84 (1H), 7.49 (1H), 7.38 (1H), 4.69 (2H), 4.24 (2H).

Synthesis of (p-Cymene)(L')RuCl$_2$

We demonstrate that a ligand L' selected from any group, i.e., $L^1$, $L^2$, $L^3$, $L^4$, $L^5$ in Table 1 can be used as a starting substance to react readily with dichloro(p-cymene)ruthenium(II) dimer, i.e., [(p-cymene)RuCl$_2$]$_2$, to form an intermediate (p-cymene)(L')RuCl$_2$.

5. Synthesis of (p-Cymene)(2,2'-bipyridine)RuCl$_2$ (9)

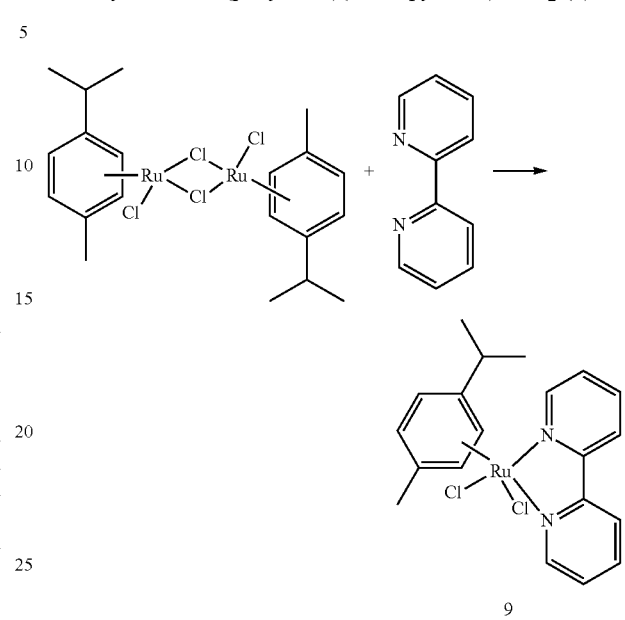

[(p-cymene)RuCl$_2$]$_2$ (2.0 g, 3.27 mmol) and 2,2'-bipyridine (1.03 g, 6.59 mmol) were dissolved in 400 mL of methanol and the solution was refluxed for 8 hours. During the process, the color of the solution turned from red to yellow. The final solution was roto-evaporated and the solid was purified by chromatography using silica column and methanol/water eluent to afford 1.64 g of yellow powder (9). $^1$H NMR (CDCl$_3$, 400 MHz) δ 9.76 (2H), 8.40 (2H), 8.07 (2H), 7.75 (2H), 6.22 (2H), 6.09 (2H), 2.74 (1H), 2.29 (3H), 1.05 (6H).

6. Synthesis of (p-Cymene)(4,7-diphenyl-1,10-phenanthroline)RuCl$_2$ (10)

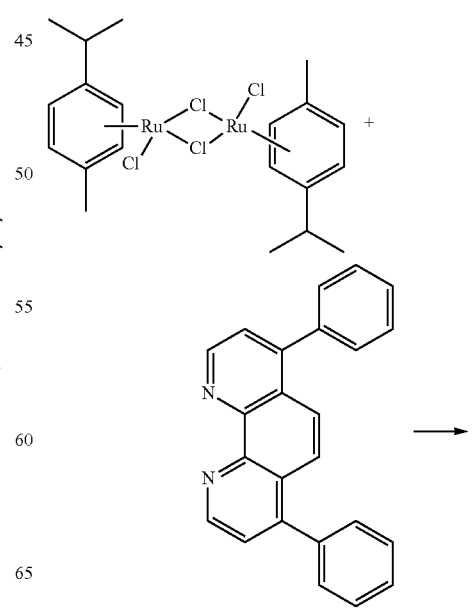

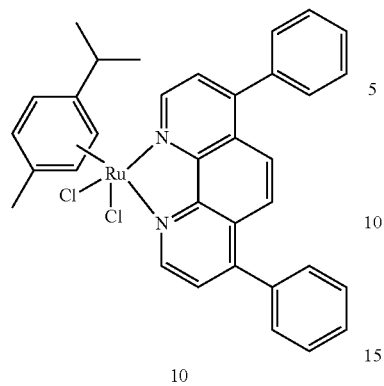

10

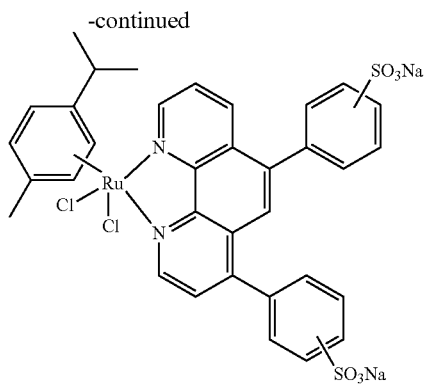

11

Figure 4:
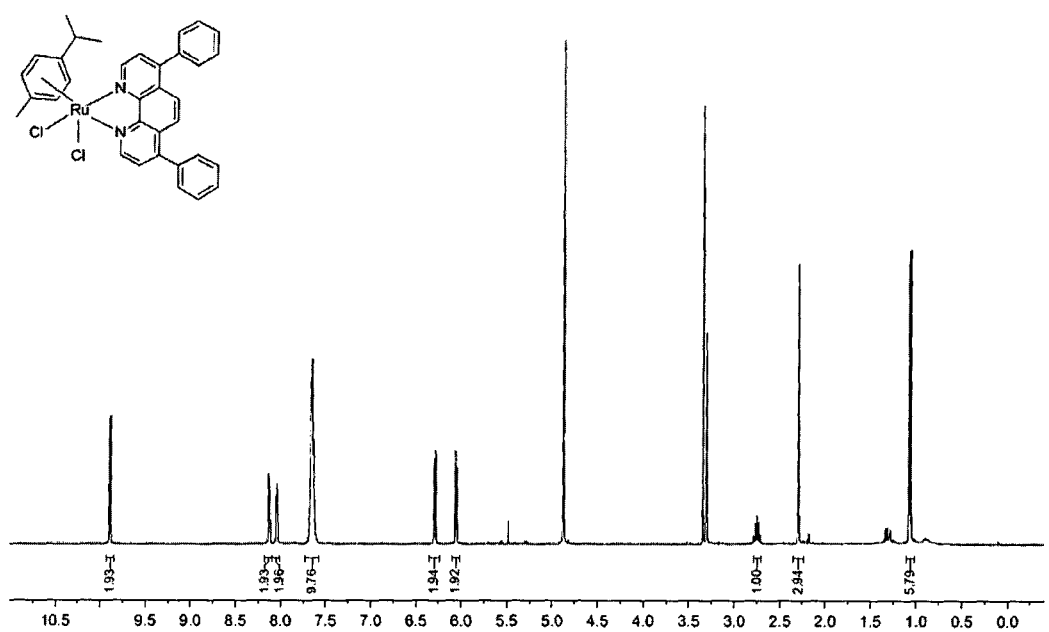
FIG. 4 is a $^1$H NMR spectrum of compound 10.

[(p-cymene)RuCl$_2$]$_2$ (0.613 g, 1.0 mmol) and 4,7-diphenyl-1,10-phenanthroline (0.665 g (2 mmol) were dissolved in 50 mL of absolute ethanol and the solution was refluxed under argon for four hours. The ethanol was roto-evaporated and the yellow solid was dissolved in dichloromethane and dropped into dry ether. The yellow precipitate was filtered and dried in vacuo. Yield 1.21 g (95%). $^1$H NMR (CD$_3$OD, 400 MHz, See FIG. 4) δ 9.89 (d, J=5.5 Hz, 2H), 8.13 (d, J=2.5 Hz, 2H), 8.05 (d, J=5.4 Hz, 2H), 7.73-7.57 (m, 10H), 6.29 (d, J=6.4 Hz, 2H), 6.06 (d, J=6.3 Hz, 2H), 2.74 (m, J=13.6, 6.8 Hz, 1H), 2.30 (s, 3H), 1.07 (t, J=10.6 Hz, 6H).

7. Synthesis of (p-Cymene)(bathophenanthroline disulfonate sodium)RuCl$_2$ (11)

[(p-cymene)RuCl$_2$]$_2$ (0.806 g, 1.316 mmol) in 150 mL of methanol and bathophenanthroline disulfonate sodium (1.412 g (2.632 mmol) in 75 mL of water were mixed and refluxed under argon for four hours. The solvents were roto-evaporated and the yellow solid (2.2 g) was used without further purification for further use.

Synthesis of (L')(L")RuCl$_2$

Figure 5:
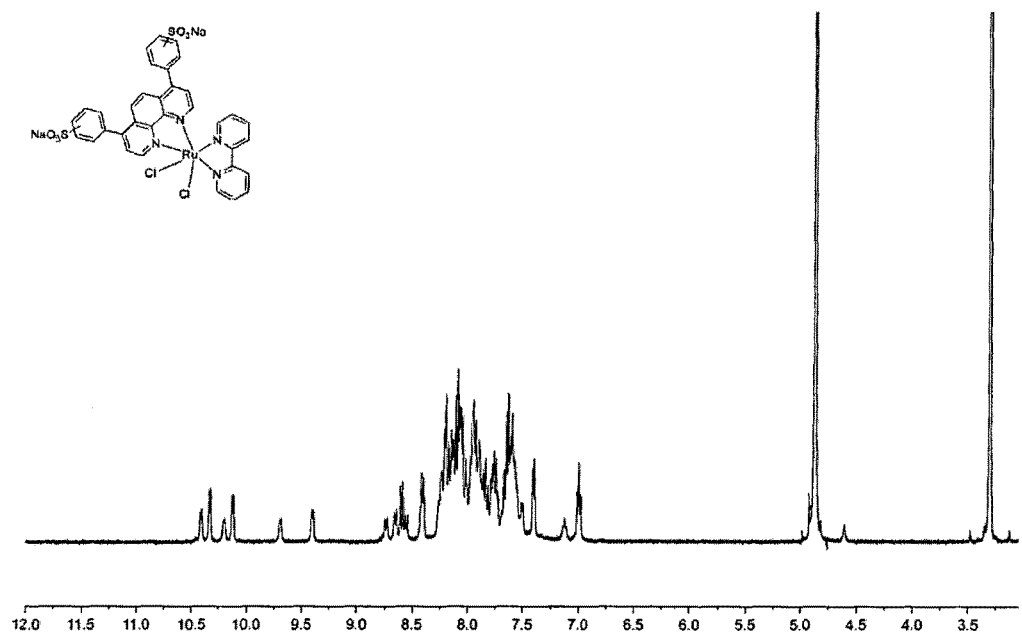
FIG. 5 is a $^1$H NMR spectrum of compound 15.

We demonstrate that a ligand L" selected from any group, i.e., L$^1$, L$^2$, L$^3$, L$^4$, L$^5$ in Table 1 can replace the residual p-cymene in the intermediates (p-cymene)(L')RuCl$_2$ to form (L')(L")RuCl$_2$. Due to the difficulties in separating the stereoisomeric mixtures, these dichloro-heteroleptic diimine complexes were used without further purification for making tris-heteroleptic ECL labels. An exemplary $^1$H NMR of compound 15 in CD$_3$OD was shown in FIG. 5.

8. Synthesis of cis-(2,2'-bipyridine)[4-(2,2'-bipyridin-4-yl)butanoic acid]ruthenium(II) dichloride complex (12)

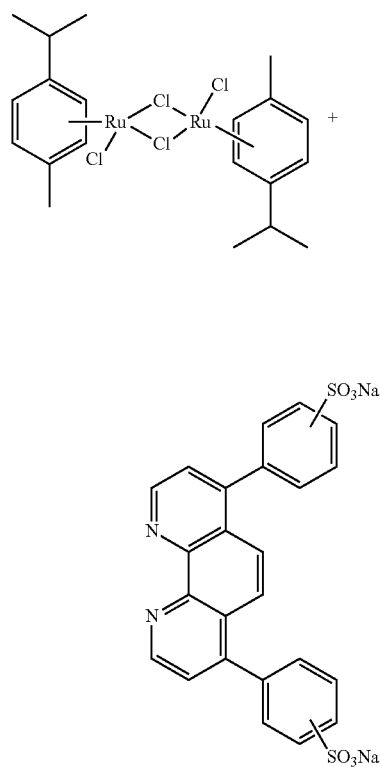

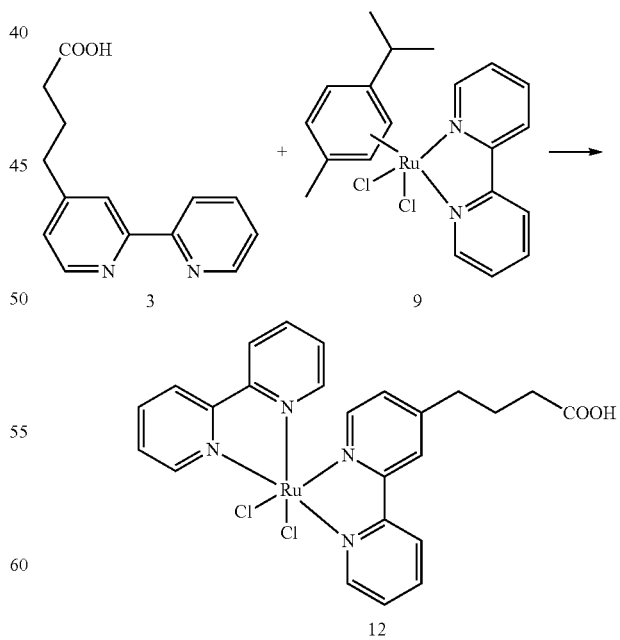

12

4-(2,2'-bipyridin-4-yl)butanoic acid (0.44 g, 1.8 mmol) and (p-cymene)(2,2'-bipyridine)RuCl$_2$ (0.83 g, 1.74 mmol) and 0.61 g (14.39 mmol) of lithium chloride were mixed in 15 mL of DMF. The mixture was refluxed under nitrogen for three hours. During this process, the colour of the solution turned from yellow into dark purple. After the mixture was cooled to room temperature, it was poured in 200 mL of ether while stirred. The dark purple precipitate was collected by filtration and further chromatographed over silica column using methanol/water as eluent to remove small fluorescent compound(s). Yield 0.40 g (40%).

9. Synthesis of cis-(2,2'-bipyridine)[4-methyl-4'-(3-carboxypropyl)-2,2'-bipyridine]ruthenium(II) dichloride complex (13)

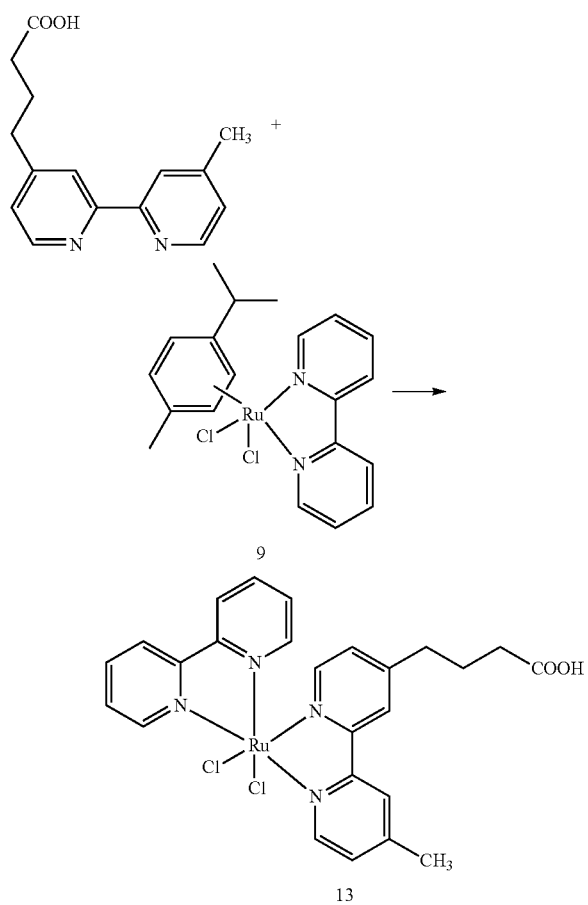

Compound 13 was synthesized in the same way as described for compound 12.

10. Synthesis of cis-(4,7-diphenyl-1,10-phenanthroline)[4-(2,2'-bipyridin-4-yl)butanotate sodium]ruthenium(II) dichloride complex (14)

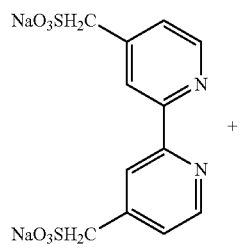

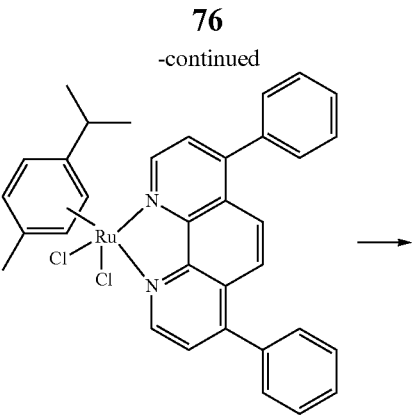

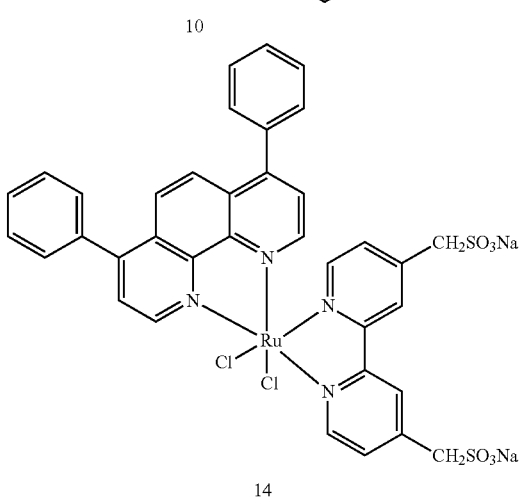

Sodium [2,2'-bipyridine]-4,4'-diyldimethanesulfonate (1.56 g, 4.02 mmol) and (p-cymene)(4,7-diphenyl-1,10-phenanthroline)RuCl$_2$ (2.56 g, 3.92 mmol) were mixed with 1.35 g (31.84 mmol) of lithium chloride in 50 mL of DMF. The solution was refluxed under nitrogen for three hours. After cooling to room temperature, the dark purple mixture was poured in 400 mL of acetone. The dark purple solid was collected. The filtrate was found to contain the product and was roto-evaporated. The combined purple solid was chromatographed over silica gel using methanol as eluent. The concentrated purple solution was dropped into dry ether. The dark purple solid was filtered and dried. Yield 3.4 g (97%).

11. Synthesis of (2,2'-bipyridine)(bathophenanthroline disulfonate sodium) ruthenium(II) dichloride complex (15)

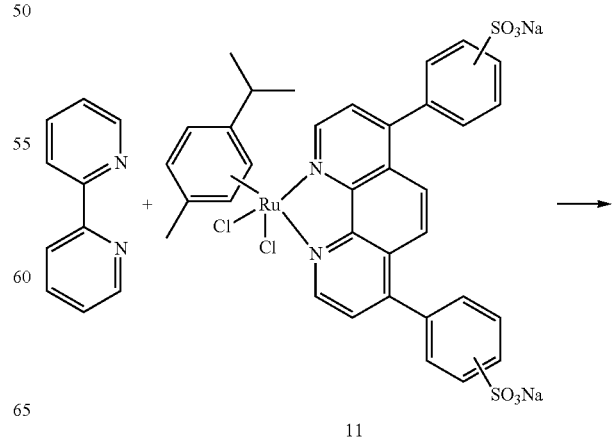

-continued

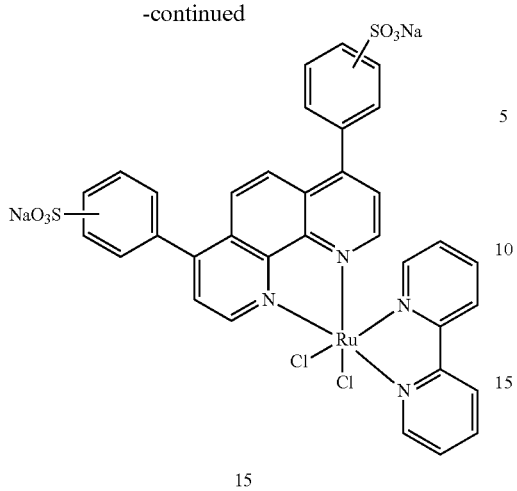

15

2,2'-bipyridine (0.355 g, 2.27 mmol) and (p-cymene)(bathophenanthroline disulfonate sodium)RuCl$_2$ (1.785 g, 2.12 mmol) were mixed with 0.772 g (18.2 mmol) of lithium chloride in 30 mL of DMF. The solution was refluxed under nitrogen for 3.5 hours. After cooling to room temperature, the dark purple solution was roto-evaporated and the solid was re-dissolved in methanol. The column chromatography over silica gel yield 1.75 g dark purple solid. (isomeric mixture). See FIG. 5 for $^1$H NMR of 15 in CD$_3$OD.

Synthesis of (L')(L")(L''')Ru Labels

12. Synthesis of a Tris-heteroleptic Metal Complex Label—Ru(2,2'-bipyridine)(bathophenanthroline disulfonate)[4-(2,2'-bipyridin-4-yl)butanoic acid] (16)

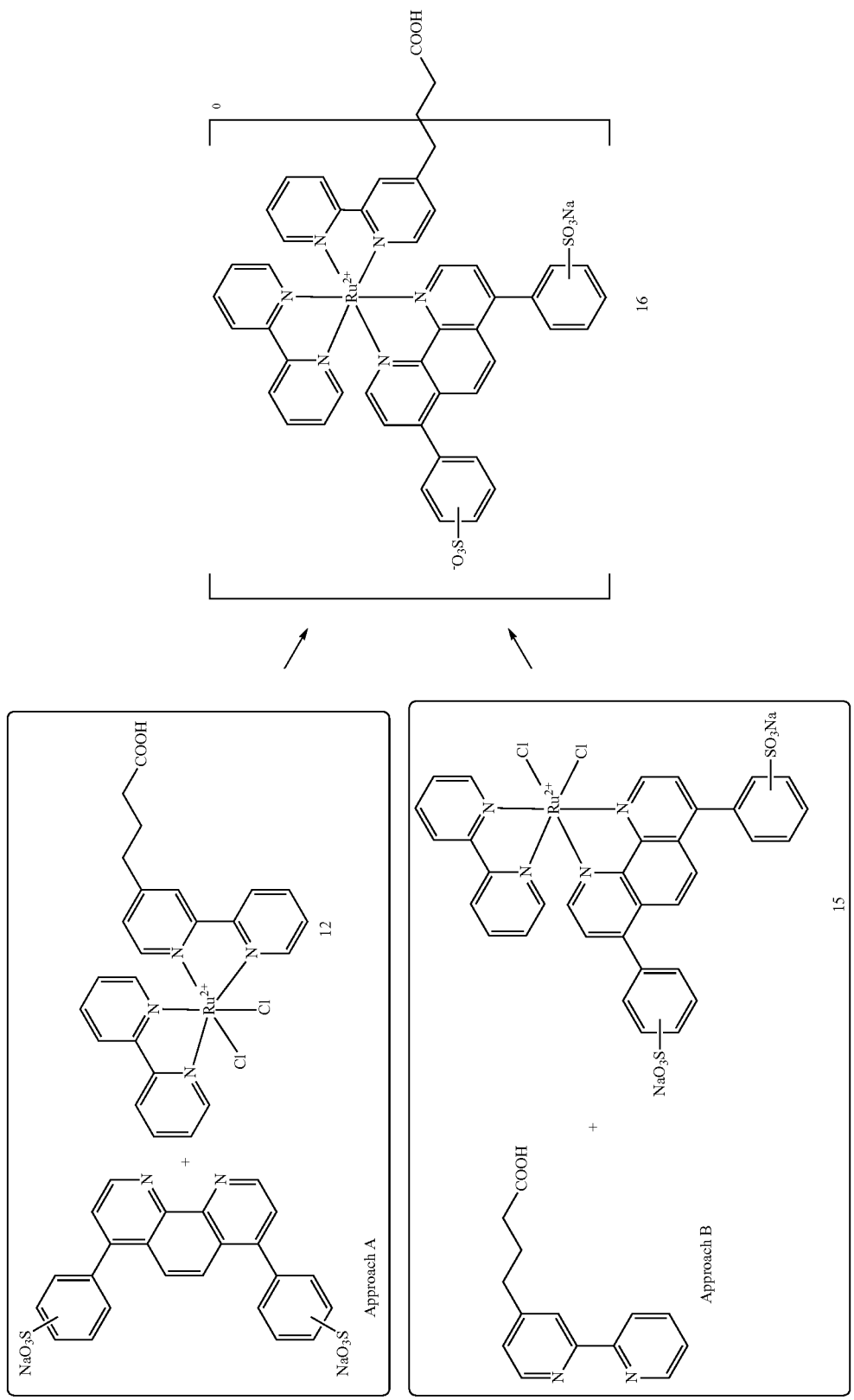

Label 16 was synthesized through two different approaches. In approach A, a di-anionic ligand, bathophenanthroline disulfonate sodium salt ($L^2$ as defined in this invention), replaces the two coordinating chlorine atoms of a $(L^1)(L^3)RuCl_2$ complex 12 to form the target label 16. In approach B, a bioconjugatable ligand, 4-(2,2'-bipyridin-4-yl)butanoic acid 3 ($L^1$ as defined in this invention) replaces the two coordinating chlorine atoms of a $(L^2)(L^3)RuCl_2$ complex 15 to form the same target label 16. The details of the two synthetic approaches are described below.

Approach A: 200 mg of 12 (0.35 mmol) and 191.8 mg (0.36 mmol) were dissolved in 25 mL of methanol/water (4:1) and the solution was refluxes for 3.5 hours under nitrogen. The color changed from dark purple into bright orange during this process. The reaction solution was filtered and concentrated to 5 mL followed by column chromatography over silica gel using methanol/water (2:1). The target compound was obtained from roto-evaporation and dried in vacuo. Yield 200 mg.

Figure 6:
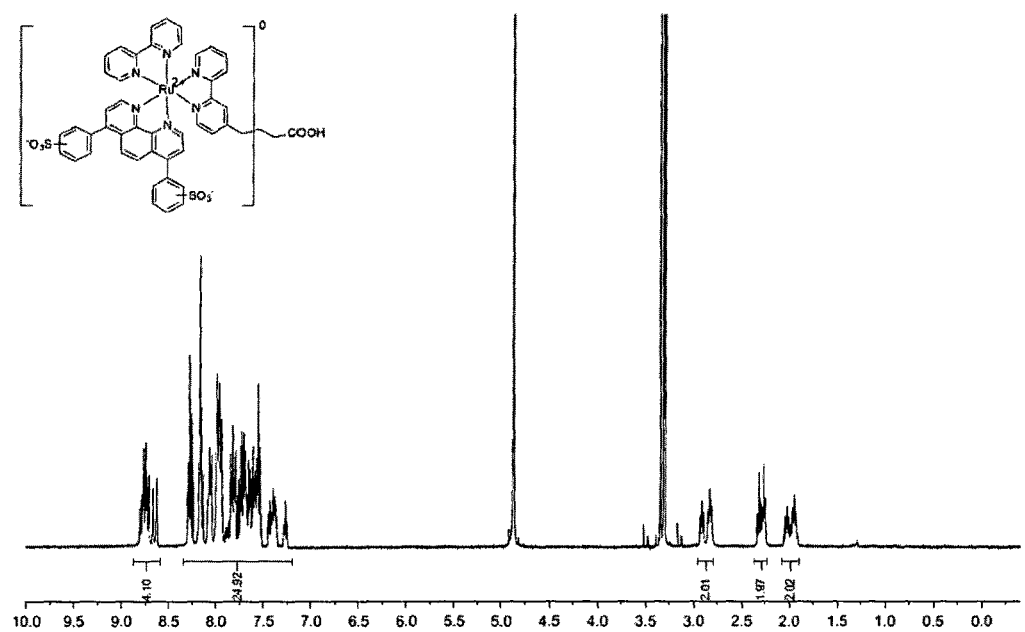
FIG. 6 is a $^1$H NMR spectrum of compound 16.

Approach B: 800 mg (0.925 mmol) of 15 and 224 mg (0.925 mmol) of 4-(2,2'-bipyridin-4-yl)butanoic acid (3) were dissolved in 40 mL of methanol/water (3:1) and the solution was refluxes for 3 hours under nitrogen. The color changed from dark purple into bright orange during this process. The reaction solution was filtered and concentrated to 10 mL followed by column chromatography over silica gel using methanol/water (2:1). The target compound was obtained from roto-evaporation and dried in vacuo. Yield 650 mg (65%). See FIG. 6 for $^1$H NMR. $^1$H NMR (CD$_3$OD, 400 MHz) δ 8.60-8.85 (4H), 7.22-8.35 (25H), 2.78-2.96 (2H), 2.22-2.36 (2H), 1.90-2.08 (2H).

11. Synthesis of Two Tris-heteroleptic Metal Complex Labels with Different Bioconjugatable Ligand ($L^1$ as Defined in this Invention) from a Common Intermediate $(L^2)(L^3)RuCl_2$ complex (15)—Ru(2,2'-bipyridine)(bathophenanthroline disulfonate)[4-methyl-4'-(3-carboxypropyl)-2,2'-bipyridine] (17) and Ru(2,2'-bipyridine)(bathophenanthroline disulfonate)[5-((1,10-phenanthrolin-5-yl)amino)-5-oxopentanoic acid] (18)

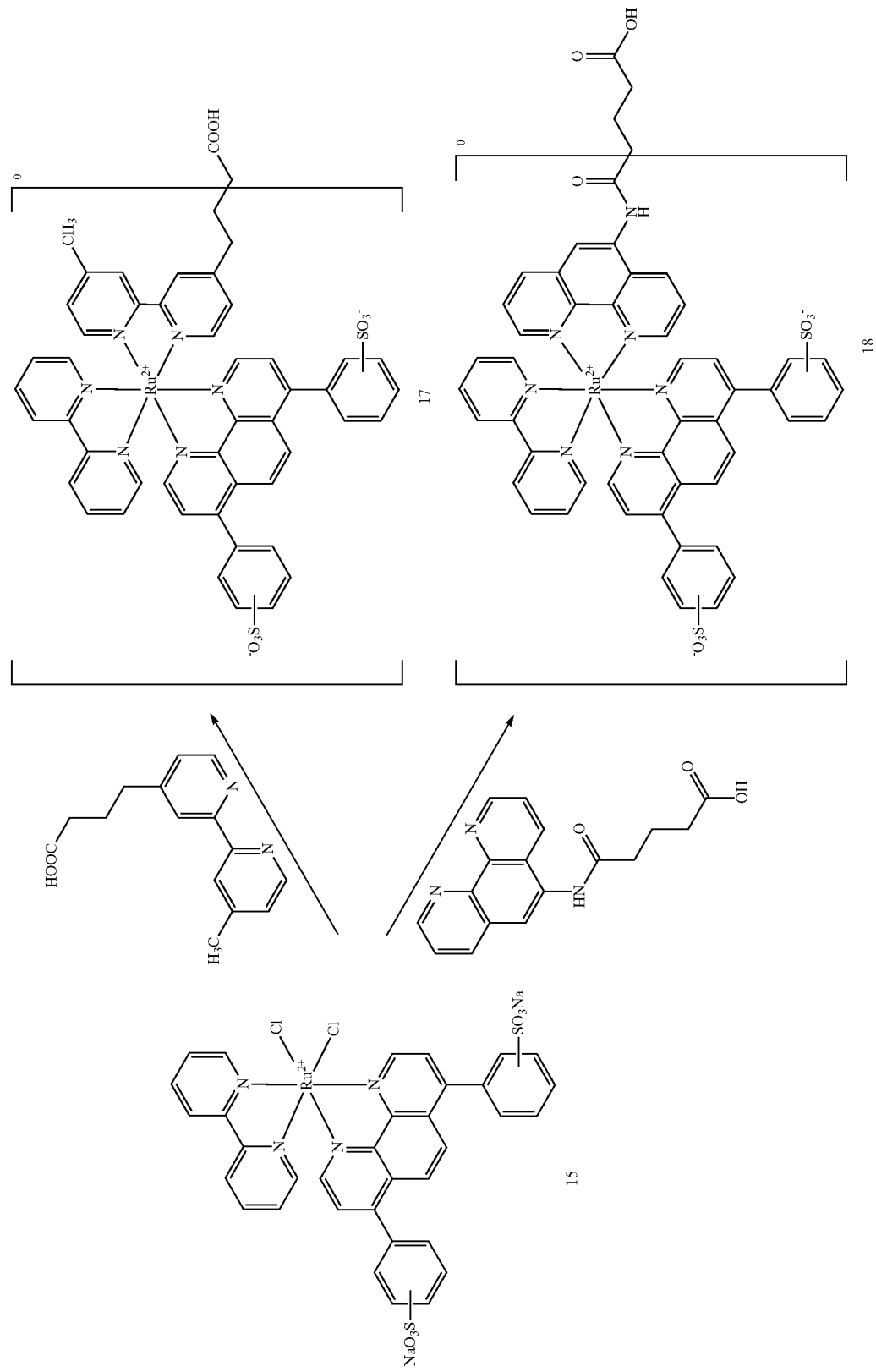

Compounds 17 and 18 were synthesized using the above approach B as well.

Figure 7:
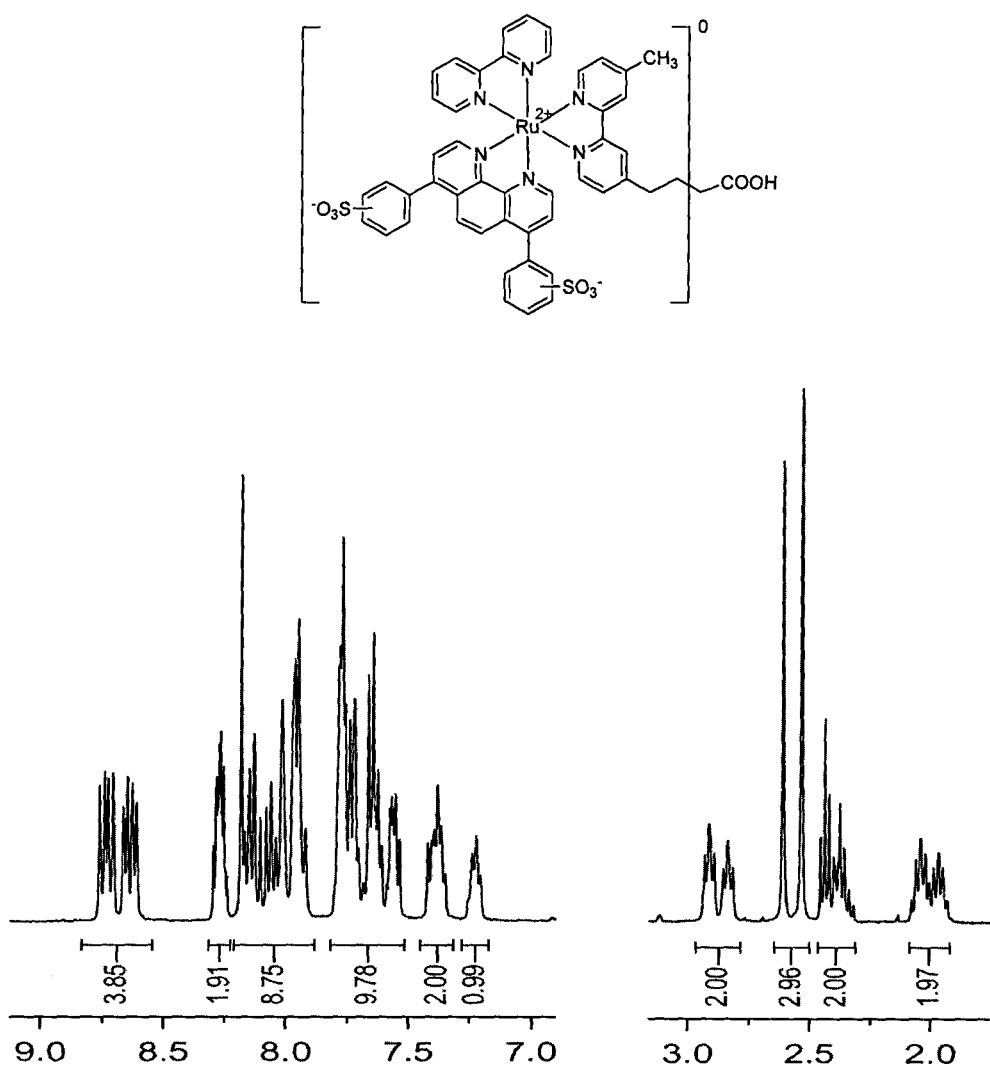
FIG. 7 is a $^1$H NMR spectrum of label 17 (left: aromatic region; right: aliphatic region).

Label 17: 505 mg (0.58 mmol) of 15 and 179 mg (0.70 mmol) of 4-(4'-methyl-[2,2'-bipyridin]-4-yl)butanoic acid were dissolved in 30 methanol/water (3:1) and the solution was refluxes for 3.5 hours under nitrogen. The color changed from dark purple into bright orange during this process. The reaction solution was filtered and roto-evaporated to dryness. The solid was re-dissolved in methanol/water mixture and was purified by chromatography over silica gel. The target compound was obtained from roto-evaporation and dried in vacuo. Yield 410 mg. See FIG. 7 for $^1$H NMR. $^1$H NMR (CD$_3$OD, 400 MHz) δ 8.57-8.80 (4H), 7.90-8.34 (11H), 7.52-7.84 (10H), 7.34-7.45 (2H), 7.18-7.29 (1H), 2.77-2.95 (2H), 2.52-2.66 (3H), 2.10-2.34 (2H), 1.87-2.08 (2H).

Figure 8:
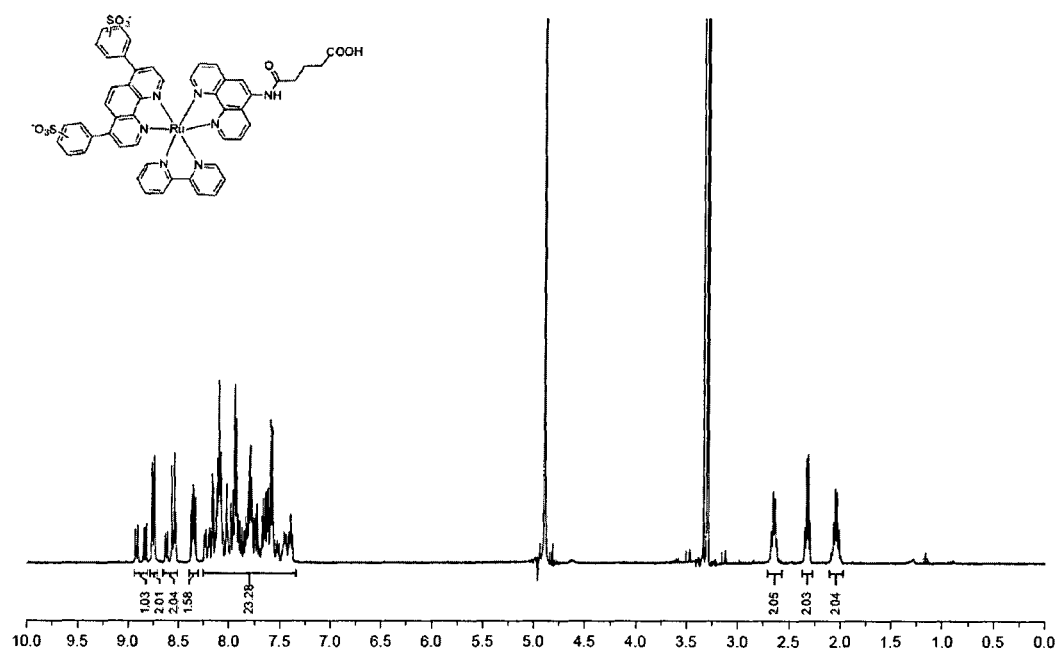
FIG. 8 is a $^1$H NMR spectrum of label 18.

Label 18: 340 mg (0.39 mmol) of 15 and 121.6 mg (0.39 mmol) of 5-((1,10-phenanthrolin-5-yl)amino)-5-oxopentanoic acid were dissolved in 35 methanol/water (6:1) and the solution was refluxes for 3.5 hours under nitrogen. The color changed from dark purple into bright orange during this process. The reaction solution was filtered and roto-evaporated to dryness. The solid was re-dissolved in methanol/water mixture and was purified by chromatography over silica gel using methanol/water (2:1) as eluent. The target compound was obtained from roto-evaporation and dried in vacuo. Yield 300 mg (75%). See FIG. 8 for $^1$H NMR.

12. Synthesis of Two Tri-heteroleptic Labels with Charging Groups on 2,2'-bipyridine from a Common Intermediate (L$^2$)(L$^3$)RuCl$_2$ complex(14): Ru(2,2'-bipyridine-4,4'-diyldimethanesulfonate)(4,7-diphenyl-1,10-phenanthroline)[4-(2,2'-bipyridin-4-yl)butanoic acid] (19) and Ru(2,2'-bipyridine-4,4'-diyldimethanesulfonate)(4,7-diphenyl-1,10-phenanthroline)[5((1,10-phenanthrolin-5-yl)amino)-5-oxopentanoic acid] (20)

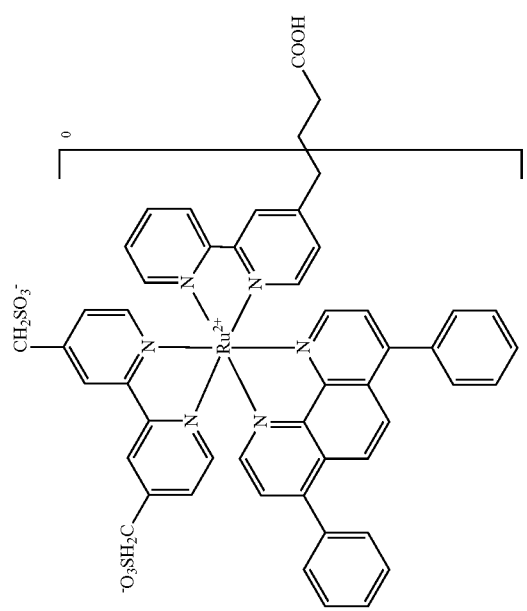
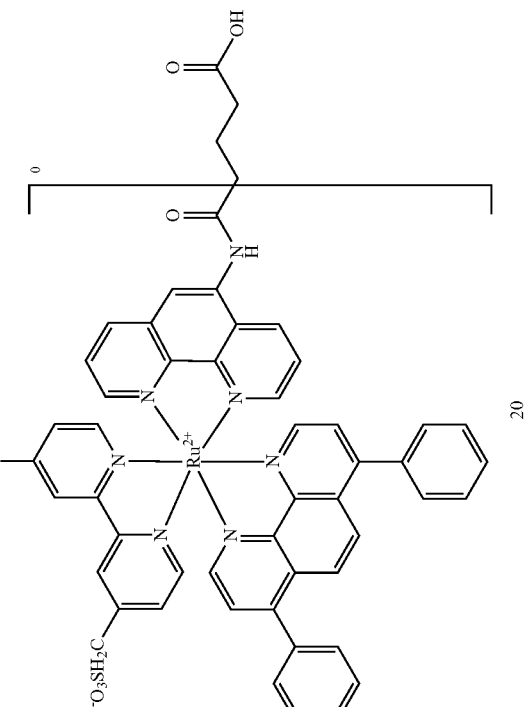
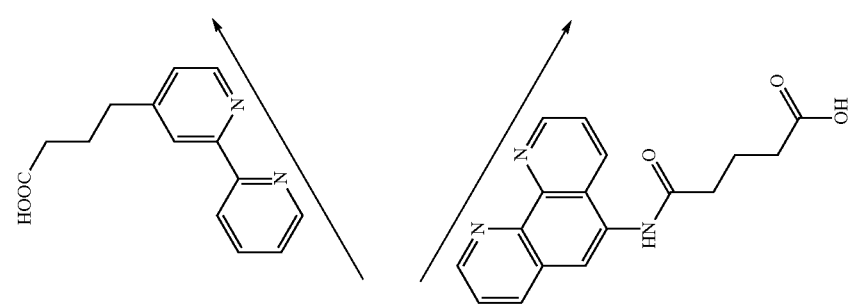
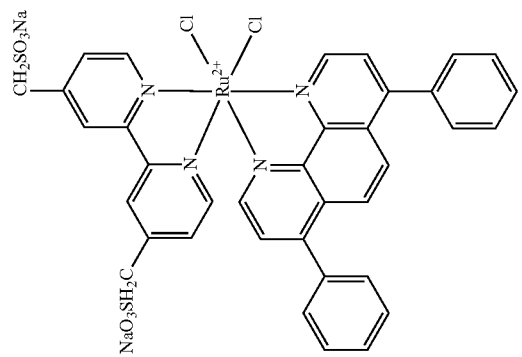

Figure 9:
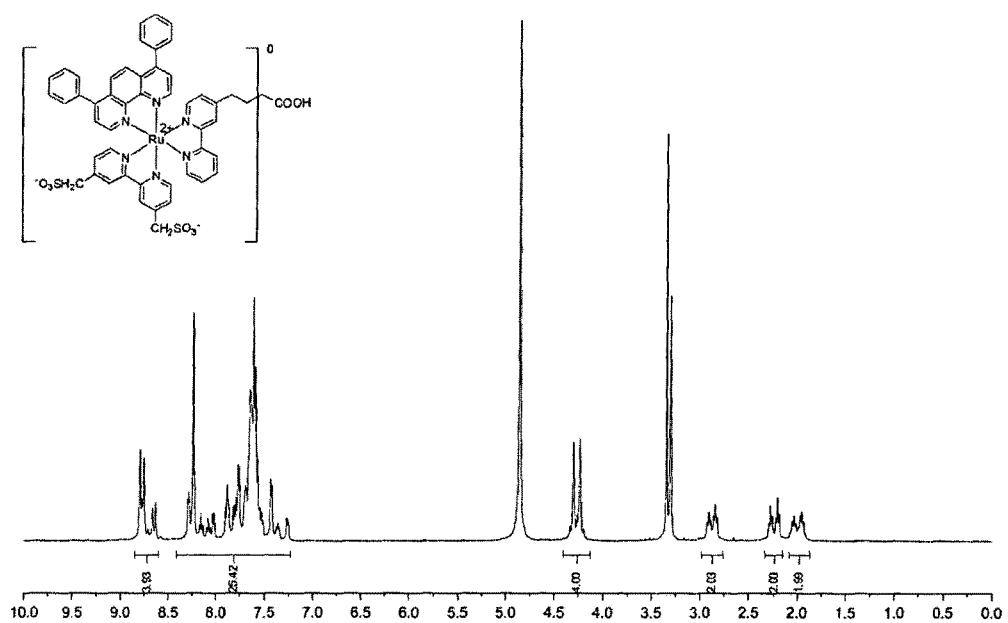
FIG. 9 is a $^1$H NMR spectrum of label 19.

Label 19: 2.00 g (2.24 mmol) of 14 and 0.54 g (2.23 mmol) of 4-(2,2'-bipyridin-4-yl)butanoic acid (3) were dissolved in 35 methanol/water (6:1) and the solution was refluxes for 3 hours under nitrogen. The color changed from dark purple into bright orange during this process. The reaction solution was filtered and roto-evaporated to dryness. The solid was re-dissolved in methanol/water mixture and was purified by chromatography over silica gel using methanol/water (4:1) as eluent. After roto-evaporation, the concentrated solution was dropped into dry ether and filtered to afford 630 mg of brown powder. Yield 27.6%. $^1$H NMR (CD$_3$OD, 400 MHz, FIG. 9) δ 8.60-8.85 (4H), 7.20-8.40 (25H), 4.10-4.45 (4H), 2.73-3.00 (2H), 2.12-2.34 (2H), 1.83-2.10 (2H).

Figure 10:
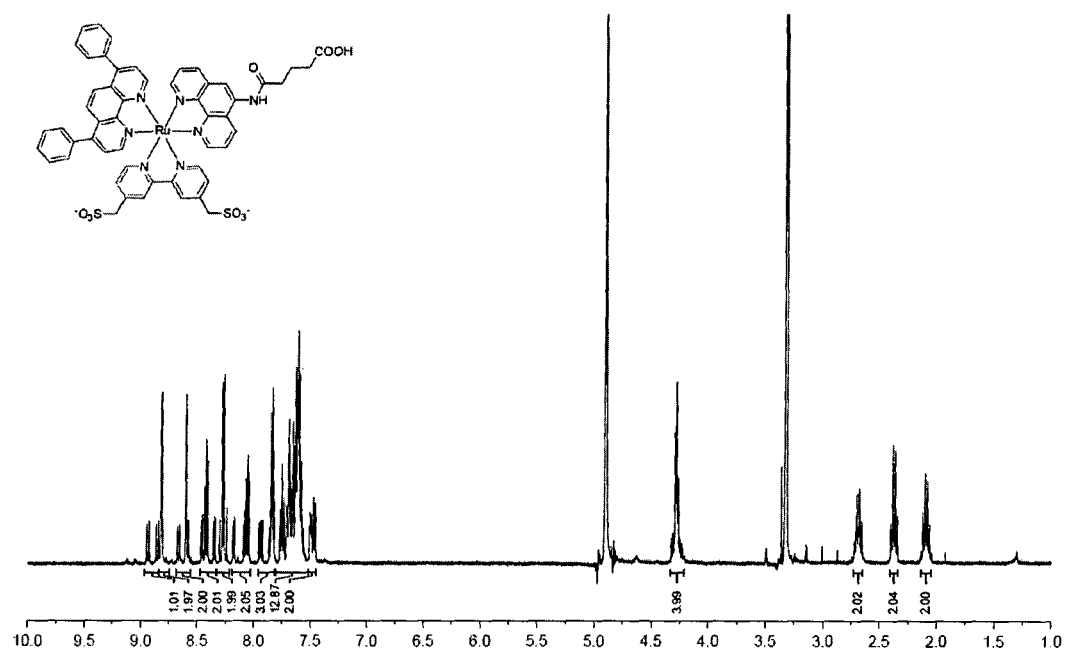
FIG. 10 is a $^1$H NMR spectrum of label 20.

Label 20: 500 mg (0.56 mmol) of 14 and 173 mg (0.56 mmol) of 5-((1,10-phenanthrolin-5-yl)amino)-5-oxopentanoic acid were dissolved in 35 methanol/water (6:1) and the solution was refluxes for 3 hours under nitrogen. The color changed from dark purple into bright orange during this process. The reaction solution was filtered and roto-evaporated to dryness. The solid was re-dissolved in methanol/water mixture and was purified by chromatography over silica gel using methanol/water (4:1) as eluent. The target compound was obtained from roto-evaporation and dried in vacuo. Yield 180 mg (29.6%). See FIG. 10 for $^1$H NMR.

13. Synthesis of Tris-heteroleptic Metal Complex—Ru(2,2'-bipyridine)(2,2'-bipyridine-4,4'-diyldimethanesulfonate)[4-(2,2'-bipyridin-4-yl)butanoic acid] (21)

145.5 mg (0.375 mmol) of sodium 2,2'-bipyridine-4,4'-diyldimethanesulfonate and 203.4 mg (0.357 mmol) of 12 was mixed in 15 ml of water/methanol (40:60) solution. The dark violet solution was refluxed under nitrogen for three hours. The resultant bright orange solution was concentrated by roto-evaporation and purified by column chromatography over silica gel using water/methanol (30:70) as eluent to afford 150 mg of orange compound (21). $^1$H NMR (CD$_3$OD, 400 MHz) δ 8.64-8.79 (5H), 8.59 (1H), 8.10 (3H), 7.67-7.90 (6H), 7.41-7.57 (5H), 7.32-7.38 (1H), 4.26 (s, 4H), 2.81-2.90 (2H), 2.17-2.28 (2H), 1.93-2.05 (2H).

14. Synthesis of Tri-heteroleptic Label Ru[(4'-methyl-2,2'-bipyridin-4-yl)methanesulfonate][(4'-hydroxymethyl-2,2'-bipyridin-4-yl)methanesulfonate][4-(2,2'-bipyridin-4-yl)butanoic acid] (24)

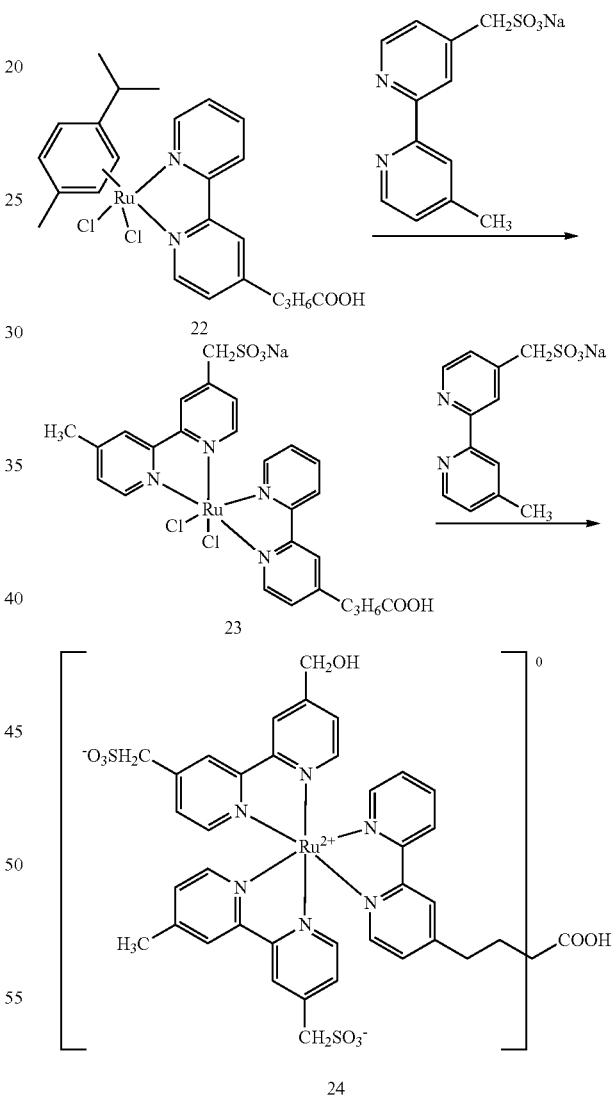

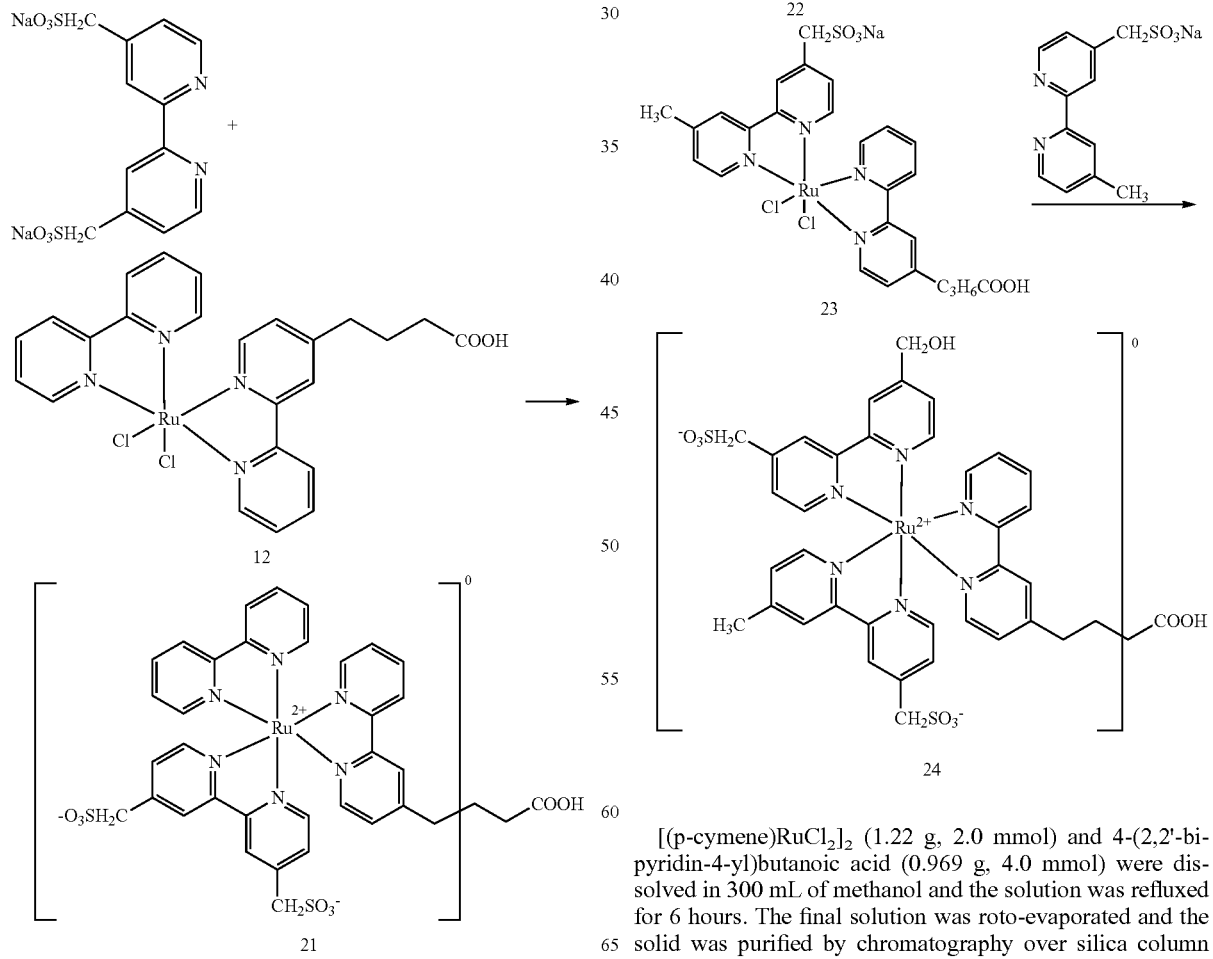

[(p-cymene)RuCl$_2$]$_2$ (1.22 g, 2.0 mmol) and 4-(2,2'-bipyridin-4-yl)butanoic acid (0.969 g, 4.0 mmol) were dissolved in 300 mL of methanol and the solution was refluxed for 6 hours. The final solution was roto-evaporated and the solid was purified by chromatography over silica column and using methanol to afford 1.6 g (73%) of yellow powder (22). $^1$H NMR (CD$_3$OD, 400 MHz) δ 9.50 (d, J=4.9 Hz, 1H), 9.35 (t, J=4.9 Hz, 1H), 8.52 (d, J=8.0 Hz, 1H), 8.41 (d, J=1.2 Hz, 1H), 8.21 (t, J=7.4 Hz, 1H), 7.75 (dd, J=9.7, 3.6 Hz, 1H), 7.64 (dd, J=5.8, 1.5 Hz, 1H), 6.11 (t, J=7.5 Hz, 2H), 5.87 (t, J=6.3 Hz, 2H), 2.97-2.87 (m, 2H), 2.63 (dq, J=13.8, 6.9 Hz, 1H), 2.40 (q, J=7.5 Hz, 2H), 2.27 (s, 3H), 2.08-1.97 (m, 2H), 1.04 (d, J=6.9 Hz, 6H).

607 mg (1.10 mmol) of 22 and 286 mg (1.0 mmol) of sodium (4'-methyl-[2,2'-bipyridin]-4-yl)methanesulfonate were mixed with 200 mg (4.72 mmol) of lithium chloride in 30 mL of DMF and refluxed under nitrogen for 3 hours. After cooling to room temperature, the reaction mixture was dropped into 400 mL of acetone. The dark precipitate was collected by filtration and washed three times with acetone to afford 300 mg (42.8%) of 23.

300 mg (0.43 mmol) of 23 and 130 mg (0.43 mmol) sodium (3'-(hydroxymethyl)-[1,1'-biphenyl]-3-yl)methanesulfonate were mixed in 30 mL of methanol and the mixture was refluxed under nitrogen for three hours. After cooling to room temperature, the solution was concentrated by rotoevaporation and purified by chromatography over silica gel using methanol/water as eluent. Yield 300 mg (34%) of 24. $^1$H NMR (400 MHz, inCD$_3$OD): δ 8.73-8.65 (m, 3H), 8.63 (s, 1H), 8.56 (s, 2H), 8.07 (t, J=7.8 Hz, 1H), 7.86-7.56 (m, 6H), 7.51-7.40 (m, 4H), 7.32 (m, 2H), 4.81 (s, 2H), 4.24 (s, 4H), 2.85 (d, J=0.7 Hz, 2H), 2.56 (s, 3H), 2.24 (dd, J=6.8, 2.5 Hz, 2H), 1.97 (m, 2H).

14. Synthesis of Two bis-heteroleptic Labels through a Common Intermediate cis-[(4'-methyl-2,2'-bipyridin-4-yl)methanesulfonate]ruthenium(II) dichloride complex (25): Ru[(4'-methyl-2,2'-bipyridin-4-yl)methanesulfonate]$_2$[4-methyl-4'-(3-carboxypropyl)-2,2'-bipyridine] (26) and Ru[(4'-methyl-2,2'-bipyridin-4-yl)methanesulfonate]$_2$[4-(2,2'-bipyridin-4-yl)butanoic acid] (27))

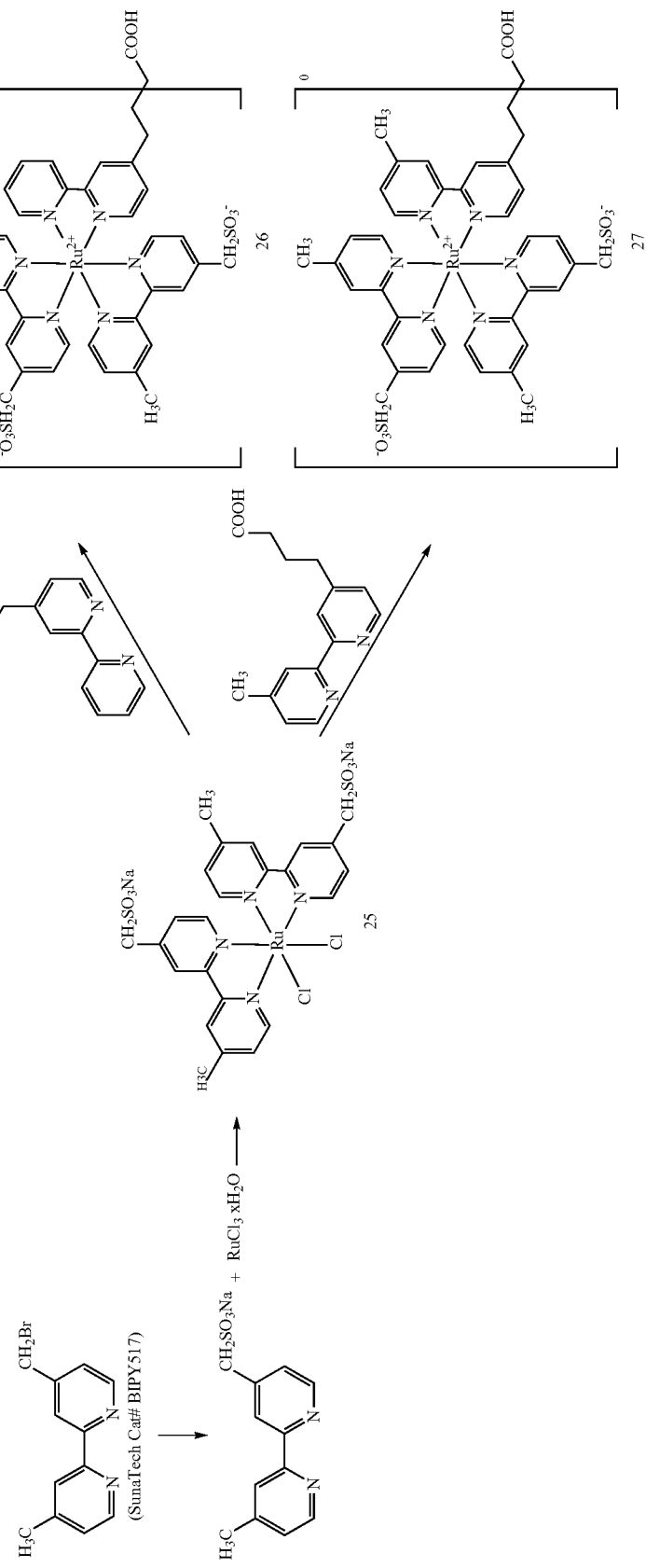

Label 26: 850 mg (1.14 mmol) of 25 and 274 mg (1.14 mmol) of 4-([2,2'-bipyridin]-4-yl)butanoic acid were mixed in in 35 mL of methanol/water (6:1). The mixture was refluxed under nitrogen for 3 hours. After cooling to room temperature, the reaction mixture was roto-evaporated to dryness, re-dissolved in water and filtered. The filtrate was purified by silica column using methanol/water as eluent to afford 240 mg of 27. $^1$H NMR (CD3OD, 400 MHz) δ 8.71 (3H), 8.60 (3H), 8.11 (1H), 7.59-7.92 (6H), 7.44-7.57 (3H), 7.27-7.42 (m, 3H), 4.28 (4H), 2.90 (2H), 2.60 (6H), 2.35 (2H), 2.04 (2H).

Label 27: 595.6 mg (0.80 mmol) of 25 and 264 mg (1.03 mmol) of 4-(4'-methyl-[2,2'-bipyridin]-4-yl)butanoic acid were mixed in in 30 mL of methanol/water (4:1). The mixture was refluxed under nitrogen for 3 hours. After cooling to room temperature, the reaction mixture was roto-evaporated to dryness, re-dissolved in water and filtered. The filtrate was purified by silica column using methanol/water as eluent to afford 150 mg of 26. $^1$H NMR (CD$_3$OD, 400 MHz) δ 8.67 (2H), 8.55 (4H), 7.55-7.78 (6H), 7.42-7.54 (2H), 7.25-7.37 (4H), 4.24 (4H), 2.84 (2H), 2.56 (9H), 2.23 (2H), 1.98 (2H).

15. Conversion of the Carboxylic Acids into their NHS Esters

The ECL labels as described above can be used directly for labeling chemicals, biochemicals and biological substances bearing one or more amino groups. The common protocol involves dicyclohexylcarbodiimide (DCC, in aprotic solutions) or the water soluble ethyl(dimethylaminopropyl) carbodiimide (EDC) in aqueous solutions with the assistance of N-hydroxysuccinimide or sulfo-NHS (N-hydroxysulfosuccinimide). An example of labeling protein with a carboxyl-bearing label is given in Example 18. A more convenient and straightforward protocol for labeling NH$_2$-bearing chemicals, biochemicals and biological substances, such as proteins, antibodies, antigen and amino-modified nucleic acids, is to use the so-called active ester, i.e., the HNS ester in one simple reaction.

A common way to synthesize an NHS-activated acid is to mix an excess amount of N-hydroxyl succinimide with the carboxyl-bearing labels in an anhydrous aprotic solvent such as methylene chloride, DMF, DMSO, acetontrile etc. An excess amount of coupling reagent such as dicyclohexylcarbodiimide (DCC) is generally added to form a highly unstable activated acid intermediate. This conversion of acid into NHS ester has been proven to be complete in acetonitrile in 20 hours at room temperature (M. Zhou et al, *Anal. Chem.* 2003, 75, 6708-6717). As an example, in order to convert label 16 to its NHS ester 28, 24.8 mg (25 mmol) of 16 was mixed with 8.7 mg (75.6 mmol) of N-hydroxyl succinimide and 16.5 mg (79.9 mmol) in 1 mL of DMF. The mixture was kept stirring under nitrogen for 20 hours. The reaction can be monitored by TLC. Dropping the reaction mixture into dry ether followed by centrifuging afforded the crude product.

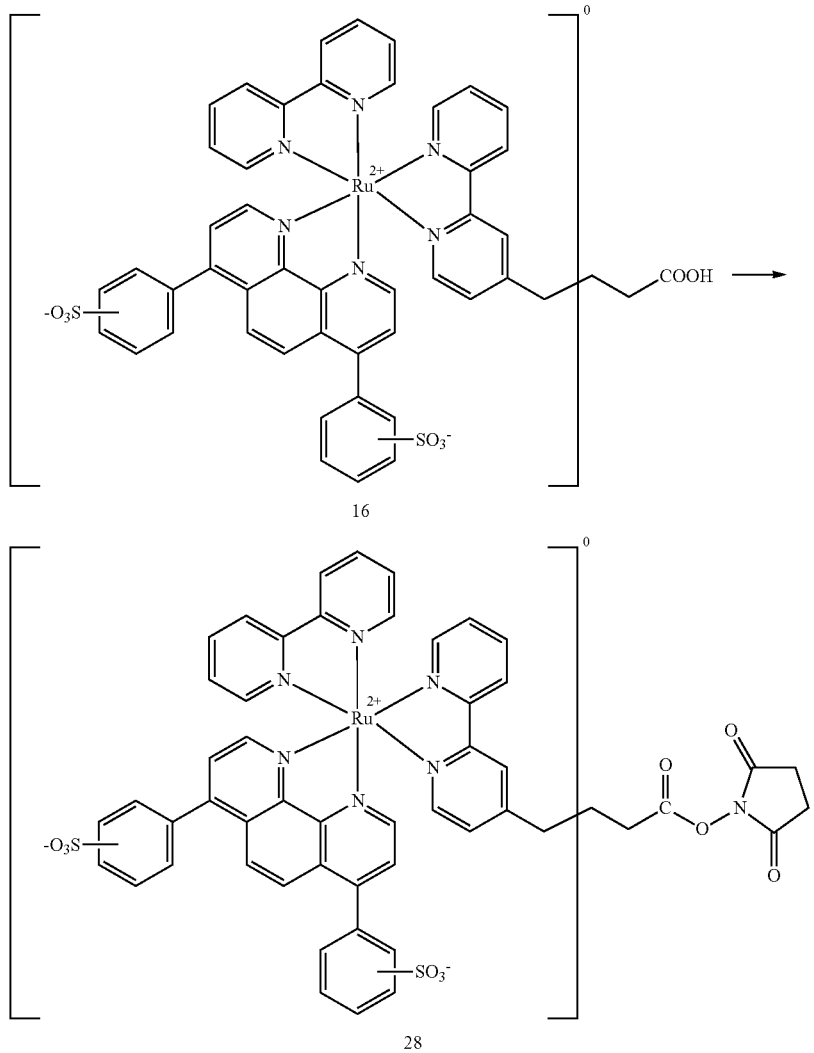

In case the carboxyl-bearing label is more soluble in water than in any aprotic solvent, the conversion to NHS ester can be carried out in aqueous solutions, such as morpholino-ethanesulfonic acid (MES) buffer, using water-soluble 1-ethyl-3-[3-dimethylaminopropyl] carbodiimide hydrochloride (EDC) as coupling agent. The NHS ester is stable enough to be purified and stored at low temperatures in the absence of water. It can also be used without being isolated from the reaction mixture immediately for labeling protein.

Photoluminescence and Electrochemiluminescence

16. Measurement of Absorption and Photoluminescence Spectra

Figure 11:
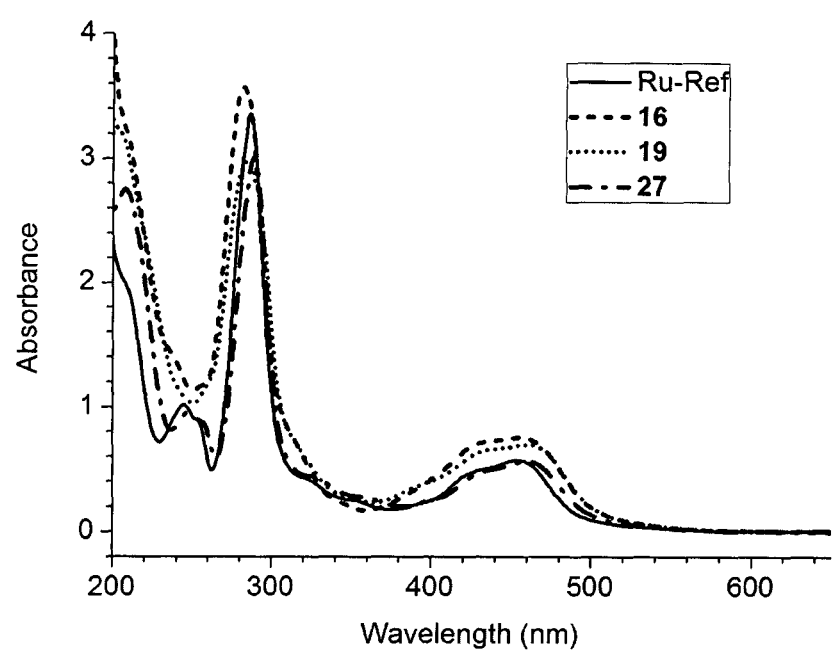
FIG. 11 is absorption spectra of labels 16, 19, 27 and Ru(2,2'-bipyridine)$_2$[4-(2,2'-bipyridin-4-yl)butanoic acid]Cl$_2$ (denoted as Ru-Ref).
Figure 12:
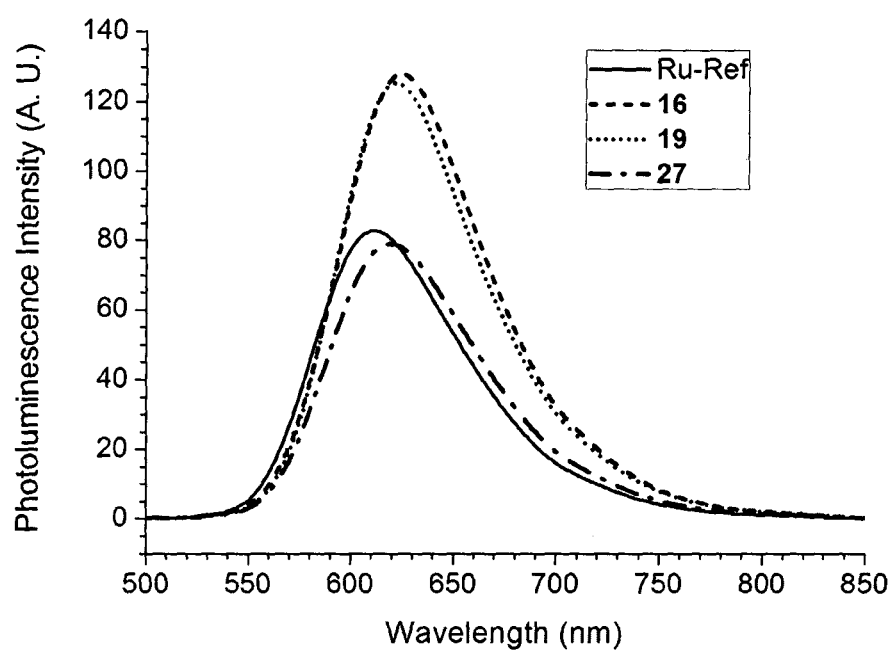
FIG. 12 is photoluminescence spectra of labels 16, 19, 27 and Ru(2,2'-bipyridine)$_2$[4-(2,2'-bipyridin-4-yl)butanoic acid]Cl$_2$ (denoted as Ru-Ref).

The ruthenium (II) diimine complexes, $M^{n+}[L^1 L^2 L^3]^{n-}$, $M^{n+}[L^1 L^4 L^5]^{n-}$ and $M^{n+}[L^1 L^4_2]^{n-}$, as synthesized in the aforementioned examples are all luminescent under light excitation at a wavelengths in their absorption bands, which are determined by measuring their absorption in the wavelength range from UV to near infrared. The exemplary absorption and photoluminescence spectra are shown in FIGS. 11 and 12, respectively. All these ruthenium(II) complexes have metal-to-ligand charge transfer (MLCT) bands in the range of 350~550 nm. The maxima of MLCT, their molar extinction coefficients and the luminescence maxima are given in Table 2.

TABLE 2

Photophysical data regarding MLCT absorption and emission in water solutions at 298 K. Ru-Ref represents a reference ruthenium(II) diimine label, Ru(2,2'-bipyridine)$_2$[4-(2,2'-bipyridin-4-yl)butanoic acid]Cl$_2$.

| Metal Complex | MLCT absorption maximum ($\lambda_{max}$) and extinction coefficients ($\varepsilon$) | | Photoluminescence (excited @ 453 nm) |
|---|---|---|---|
| | $\lambda_{max}$ (nm) | $\varepsilon$ @ $\lambda_{max}$ ($10^4$ M$^{-1}$cm$^{-1}$) | $\lambda_{max}$ (nm) |
| 16 | 455 | 1.882 | 625 |
| 17 | 455 | 1.722 | 630 |
| 18 | 454 | 1.930 | 614 |
| 19 | 460 | 1.744 | 622 |
| 20 | 459 | 1.924 | 612 |
| 21 | 457 | 1.283 | 622 |
| 24 | 459 | 1.185 | 625 |
| 26 | 461 | 1.323 | 626 |
| 27 | 459 | 1.413 | 619 |
| Ru-Ref | 454 | 1.433 | 612 |
| Ru(bpy)$_3$Cl$_2$ | 453 | 1.399 | 608 |

17. Measurement of ECL

The oxidative-reduction ECL of ruthenium(II) complexes were generated using the potential step technique in tripropylamine-containing phosphate buffers (ProCell from Roche Diagnostics, pH 6.8, 0.18 mol L$^{-1}$ tripropylamine solutions). The applied potential was 1.4 V (vs Ag/AgCl) and the ECL was recorded as a function of time. As a reference, Ru(2,2'-bipyridine)$_2$[4-(2,2'-bipyridin-4-yl)butanoic acid]Cl$_2$, denoted as Ru-Ref, was used in all ECL measurements.

Figure 13:
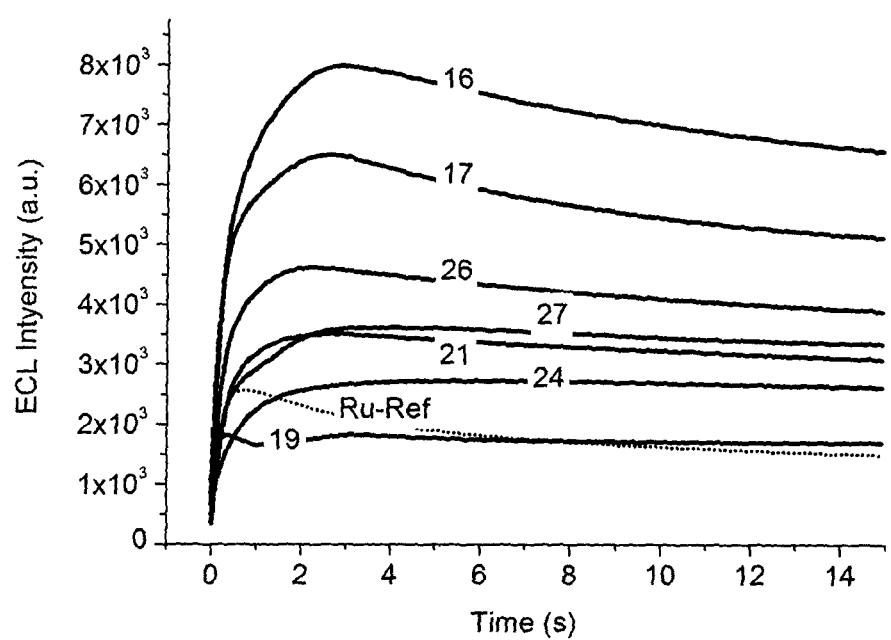
FIG. 13 compares the electrochemiluminescence of different labels in potential step experiments at 1.4 V vs. Ag/AgCl in TPA containing phosphate buffers of pH 6.8. Concentration of ruthenium(II) complexes: 0.1 µmol L$^{-1}$.

FIG. 13 shows the decay of ECL intensities of various labels in the potential step experiments. Compared with Ru-Ref, many of the labels demonstrated higher ECL intensities, while maintaining similar intensity-time profile.

Figure 14:
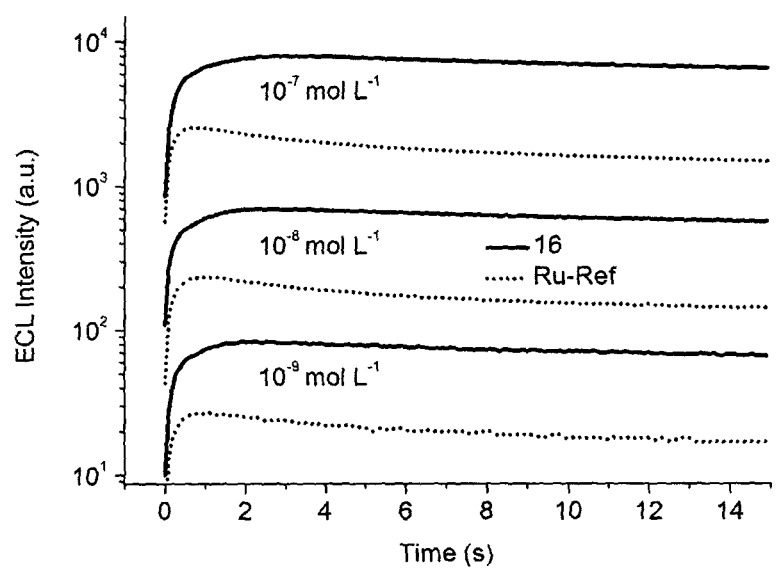
FIG. 14 compares the electrochemiluminescence of label 16 and Ru-Ref at different concentration in potential step experiments at 1.4 V vs. Ag/AgCl in TPA containing phosphate buffers of pH 6.8. Concentration of ruthenium(II) complexes: $10^{-7}$, $10^{-8}$ and $10^{-9}$ mol $L^{-1}$.

FIG. 14 shows the ECL comparison of label 16 with Ru-Ref, each at concentrations of $10^{-7}$, $10^{-8}$ and $10^{-9}$ mol L$^{-1}$.

Antibody Labeling

18. Labeling an Antibody with a Carboxyl-bearing Label 2.5 mg (2.5 μmol) of 16 was dissolved in 500 μL of MES buffer (0.1 mol L$^{-1}$, pH=4.7) at a concentration of 5.0 mmol L$^{-1}$. 1.0 mg (5.2 μmol) of 1-ethyl-3-[3-dimethylaminopropyl] carbodiimide hydrochloride (EDC) and 3.0 mg (13.8 μmol) of sulfo-NHS were added to this solution to obtain a concentration of approximately 10 mmol L$^{-1}$ EDC and 27 mmol L$^{-1}$ sulfo-NHS. The solution was shaken for 10 minutes at room temperature. 0.7 μL (10 μmol) of 2-mercaptoethanol was added to the reaction solution (final concentration of 20 mmol L$^{-1}$). After 5 minutes at room temperature, 8.0 μL (containing 40 nmol of 16) of this incubated solution was added to 500 μL of goat anti-mouse IgG (1.2 mg/mL, approximate 4 nmol of pure goat anti-mouse IgG, the challenge ratio 10) PBS (0.1 mol L$^{-1}$, pH=7.4). It was mixed and incubated for 2 hours at room temperature.

The solution (about 0.5 ml) obtained above was loaded onto the PD-10 column (packed with SEPHADEX® G-25 medium (gel filtration resin), from GE Healthcare Life Sciences) that was pre-equilibrated with PBS. Two yellow bands formed during the separation. The first eluted band, corresponding to the labeled goat anti-mouse IgG, was collected (about 0.75 ml).

To determine the actual label to protein ratio (the conjugation ratio), Bradford or BCA protein assay was used to quantify the goat anti-mouse IgG. The absorbance of label 16 at 455 nm was correlated to the label quantity based on the extinction coefficient of the label molecule. Under the conditions described above, the conjugation ratio of label 16 to goat anti-mouse IgG is about 6.

19. Labeling an Antibody with a NHS-Ester Label

The NHS-ester form of electronically neutral labels bearing —SO$_3^-$ group as disclosed in the present invention are soluble in water, DMSO and DMF. In order to avoid hydrolysis of the NHS, the labels can be either dissolved first in DMSO as a stock solution immediately before use, or used directly in the solid form by adding a pre-determined volume of protein buffer solution to the tube containing a pre-determined quantity of NHS-ester label. Described below is the procedure evolving the use of solid NHS-ester label.

1 mL of goat anti-mouse IgG (1.2 mg/mL, approximate 8 nmol protein) PBS solution was added to a tube loaded with ~8 mg of label 28 powder. The tube was shaken and the mixture was allowed to incubate for 2 hours at room temperature. The solution obtained above was loaded onto the PD-10 column that was pre-equilibrated with PBS. Two yellow bands formed as during the separation. The first eluted band, corresponding to the labeled goat anti-mouse IgG was collected.

The conjugation ratio of label 28 to goat anti-mouse IgG is determined by protein quantification assay and the absorbance measurement of label 28 at 455 nm. The ratio was 4.5. The efficiency of labeling a protein depends on a number of factors. Different labels and different proteins can have different conjugation ratio even under the same conditions (same buffer and same reaction time). The challenge ratio of label to protein should be experimentally determined in order to reach a required conjugation ratio.

Immunoassay

20. Immunoassay Using Goat Anti-mouse IgG Labeled with 16 and Ref-Ru in a Sandwich Immunoassay Format In the exemplary ECL immunoassays, mouse IgG was used as the analyte (antigen), while labeled goat anti-mouse IgG(H+L) and biotinylated rabbit anti-mouse IgG(H+L)

were used as signaling and capturing antibodies, respectively. Dynabeads® M-280 coated with streptavidin was selected as the magnetic media for capturing the biotinylated antibody/antigen/labeled antibody immunocomplex. The solutions of 1000 μl of mouse IgG at different concentration in PBS were mixed with 20 μl of 5.0 μg mL$^{-1}$ of biotinylated rabbit anti-mouse IgG in PBS, 20 μl of 1.0 μg mL$^{-1}$ of labeled goat anti-mouse IgG. Each mixture was incubated for 20 minutes at room temperature to form the sandwich immunocomplex. A suspension of 20 μl streptavidin-coated Dynabeads® M-280 (200 μg beads, pre-washed three time by PBS) was added to the above solution of rabbit anti-mouse IgG/mouse IgG/goat anti-mouse IgG sandwich immunocomplex. This suspension of total volume of 1060 μl was incubated for 20 minutes with constant gentle rotation at room temperature. The immunocomplex loaded Dynabeads were separated with an external magnet for 2 minutes while other unreacted species were removed by washing the beads with 1000 μl PBS containing 0.1% BSA for four times. After the final washing step, the beads were resuspended by 1000 μl of PBS to the concentration of 200 μg mL$^{-1}$ of beads loaded with antibody/antigen/antibody sandwich immunocomplex. 100 μl of the above solution was injected into the three-electrode measuring cell with a photomultiplier tube above the working electrode and a movable magnet underneath the working electrode. A potential step (1.4 V vs. Ag/AgCl) was employed to oxidize TPA and ruthenium(II) label, which was immobilized on the magnetic beads via the antibody/antigen/antibod sandwich, to generate ECL through the oxidative-reduction process in a phosphate buffer (ProCell from Roche Diagnostics, pH 6.8, 0.18 mol L$^{-1}$ tripropylamine solutions). After each measurement, the magnet was removed from working electrode. The measuring cell was cleaned and the electrode was regenerated electrochemically as described in the U.S. Pat. No. 5,538,687.

Figure 15:
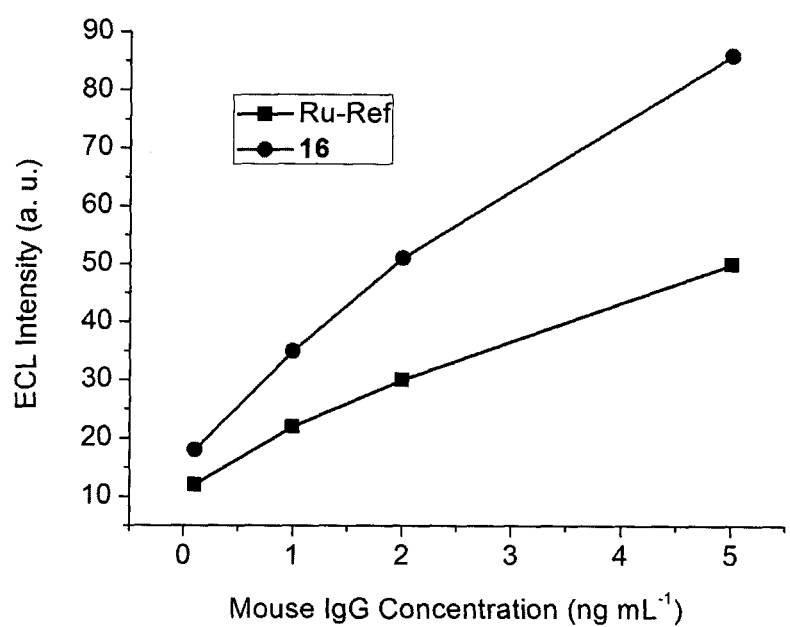
FIG. 15 compares the ECL signal levels in immunoassays using label 16 and Ru-Ref.

Evaluation was done by comparing ECL signals (integration of ECL intensity over the first 3 second) generated in a series of standard sample solutions with different mouse IgG concentrations. As label 16 demonstrated more intense ECL than Ru-Ref in the homogeneous ECL process (FIGS. 13 & 14), it was not surprising that, as an ECL label, 16 outperformed Ru-Ref in terms of the ECL signal intensity in a sandwich immunoassay (see FIG. 15).

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. An electronically neutral and tris-heteroleptic metal complex of formula II:

$$M^{n+}[L^1 L^2 L^3]^{n-} \qquad (II)$$

wherein M is ruthenium or osmium;
n is equal to or larger than 2;
$L^1$ is

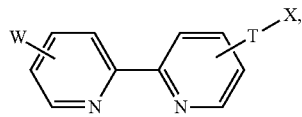

-continued

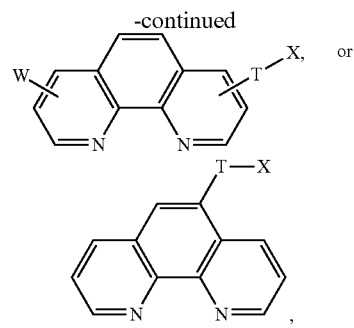

wherein X is a carboxyl,

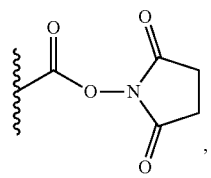 [SMILES: *C(=O)ON1C(=O)CCC1=O]

sulfo-N-succinimidyl carboxylate, phosphoramidite, isothiocyanato, formyl, hydrazino, hydroxyl, or maleimido;

T is a carbon-containing or a heteroatom-containing linker comprising a $C_1$-$C_{10}$ alkylene, $C_1$-$C_{10}$ alkenylene, —O—$C_{1-10}$—, —CONH—$C_{1-10}$—, —$C_{1-10}$—CONH—, —NHCO—$C_{1-10}$— or an aromatic ring; and W is a hydrogen, $C_1$-$C_{10}$ alkyl, $C_1$-$C_{10}$ alkenyl, $C_1$-$C_{10}$ alkyloxy, —CONH—$C_{1-10}$, —NHCO—$C_{1-10}$, —$C_{1-9}$ CONHR$^1$, substituted or unsubstituted 5- or 6-member aromatic ring, hydroxyl, amino, cyano, or halogen;

$L^2$ is

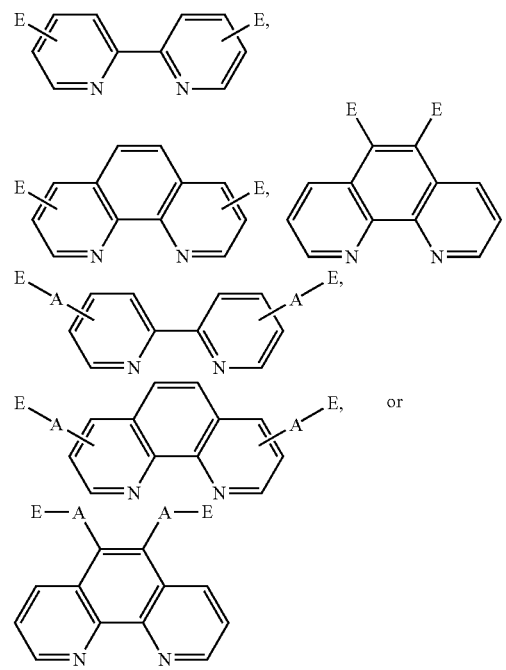

having at least one negatively charged substituent with a total number of negative charge equal to or larger than 2, wherein E is —SO$_3^-$, —OSO$_3^-$, —PO$_3$H$^-$, or —OPO$_3$H$^-$; and A is a carbon-containing or a heteroatom-containing linker comprising a C$_1$-C$_{10}$ alkylene, C$_1$-C$_{10}$ alkenylene, —O—C$_{1-10}$—, —CONH—C$_{1-10}$—, —NHCO—C$_{1-10}$—, —C$_{1-9}$CONHR$^2$—, substituted or unsubstituted 5- or 6-member aromatic ring;

L$^3$ is a 2,2'-bipyridine, or 1,10-phenanthroline, substituted with at least one W', wherein W' is a hydrogen, C$_1$-C$_{10}$ alkyl, C$_1$-C$_{10}$ alkenyl, C$_1$-C$_{10}$ alkyloxy, —CONH—C$_{1-10}$, —NHCO—C$_{1-10}$, —C$_{1-9}$CONHR$^3$, substituted or unsubstituted 5- or 6-member aromatic ring, hydroxyl, cyano, or halogen;

L$^1$, L$^2$ and L$^3$ are different from each other;

R$^1$, R$^3$ are each H, or alkyl; and

R$^2$ is an alkylene.

2. The electronically neutral and tris-heteroleptic luminescent metal complexes according to claim 1 having the structure:

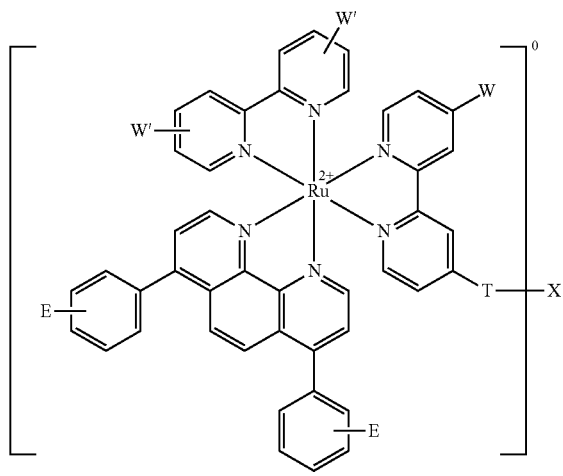

wherein X is carboxyl,

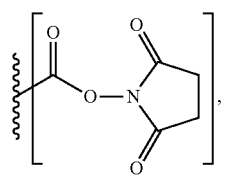

sulfo-N-succinimidyl carboxylate, phosphoramidite, isothiocyanato, formyl, hydrazino, hydroxyl, or maleimido;

T is a carbon-containing or a heteroatom-containing linker comprising a C$_1$-C$_{10}$ alkylene, C$_1$-C$_{10}$ alkenylene, —O—C$_{1-10}$—, —CONH—C$_{1-10}$—, —NHCO—C$_{1-10}$—, —C$_{1-9}$CONH—, substituted or unsubstituted 5- or 6-member aromatic ring;

W and W' are each a hydrogen, a C$_1$-C$_{10}$ alkyl, C$_1$-C$_{10}$ alkenyl, C$_1$-C$_{10}$ alkyloxy, —CONH—C$_{1-10}$, —NHCO—C$_1$-C$_{10}$, —C$_{1-9}$CONHR$^3$, substituted or unsubstituted 5- or 6-member aromatic ring, hydroxyl, cyano, or halogen;

E is —SO$_3^-$, —OSO$_3^-$, —PO$_3$H$^-$, or —OPO$_3$H$^-$; and

R$^3$ is H, or alkyl.

3. The electronically neutral and tris-heteroleptic metal complexes according to claim 2, wherein X is carboxyl; T is —(CH$_2$)$_{1-9}$—; W is H or CH$_3$; W' is H or CH$_3$; and E is —SO$_3^-$.

4. The electronically neutral and tris-heteroleptic metal complexes according to claim 2, wherein X is T is

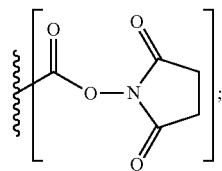

T is —(CH$_2$)$_{1-9}$—; W is H or CH$_3$; W' is H or CH$_3$; and E is —SO$_3^{31}$.

5. The electronically neutral and tris-heteroleptic metal complexes according to claim 2, wherein X is carboxyl or

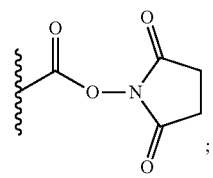 [SMILES: *C(=O)ON1C(=O)CCC1=O]

T is —(CH$_2$)$_3$—; W is H or —CH$_3$; W' is H or —CH$_3$; and E is —SO$_3^-$.

6. The electronically neutral and tris-heteroleptic metal complexes according to claim 1 having the structure:

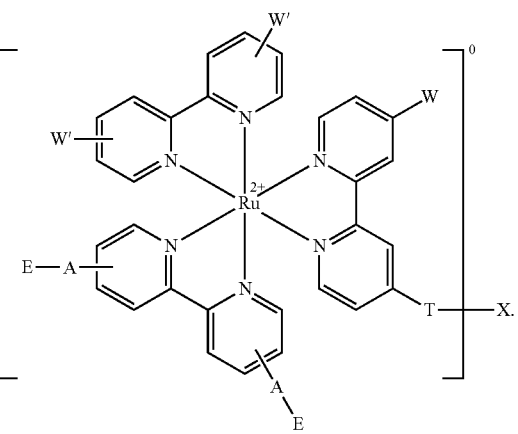

7. The electronically neutral and tris-heterolentic metal complexes according to claim 6, wherein X is carboxyl or

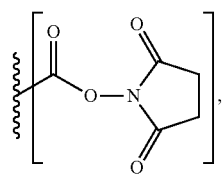

T is —CONH—C$_{1-10}$—, —NHCO—C$_1$-C$_{10}$—, —C$_{1-9}$CONH, or —(CH$_2$)$_{1-9}$—; W is H or —CH$_3$; W' is H or —CH$_3$; A is —CH$_2$—; and E is -SO$_3^-$.

8. The electronically neutral and tris-heteroleptic metal complexes according to claim 1 having the structure:

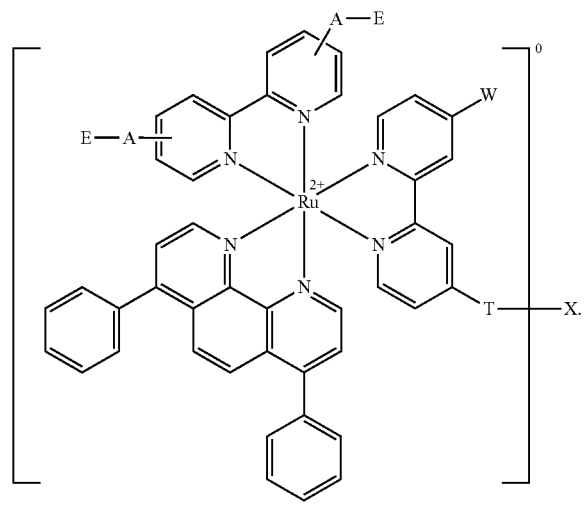

9. The electronically neutral and tris-heteroleptic metal complexes according to claim 8, wherein X is carboxyl or;

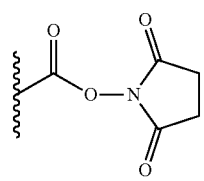 [SMILES: *C(=O)ON1C(=O)CCC1=O]

W is H or —CH$_3$; A is a C$_1$-C$_{10}$ alkylene; and E is —SO$_3^-$.

10. The electronically neutral and tris-heteroleptic metal complexes according to claim 1 having the structure:

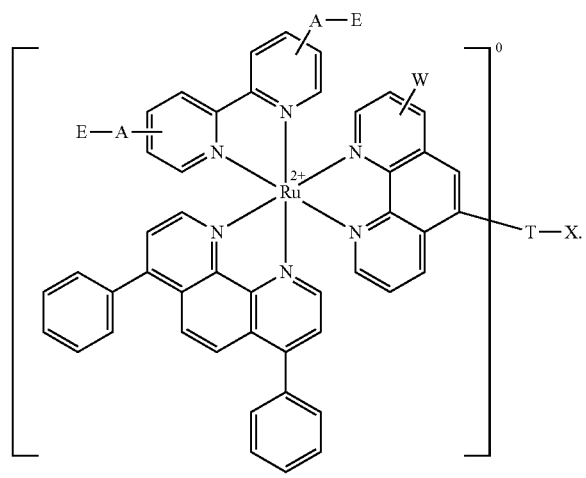

11. The electronically neutral and tris-heteroleptic metal complexes according to claim 10, wherein X is carboxyl or

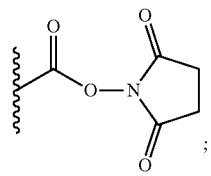 [SMILES: *C(=O)ON1C(=O)CCC1=O]

W is H or —CH$_3$; A is a C$_1$-C$_{10}$ alkylene; and E is —SO$_3^-$.

12. A method of synthesizing an electronically neutral and tris-heteroleptic metal complex label of Ru$^{2+}$[L$^1$ L$^2$ L$^3$]$^{2-}$, wherein L$^1$ is

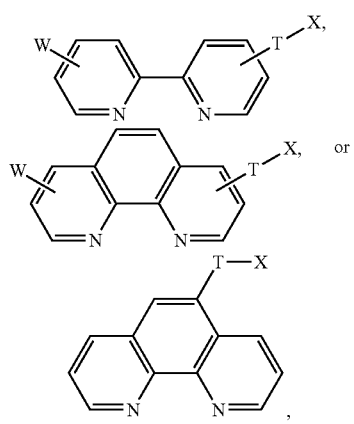

wherein X is a carboxyl

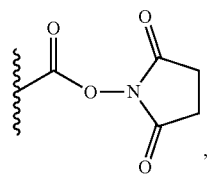 [SMILES: *C(=O)ON1C(=O)CCC1=O]

sulfo-N-succinimidyl carboxylate, phosphoramidite, isothiocyanato, formyl, hydrazino, hydroxyl, or maleimido;

T is a carbon-containing or a heteroatom-containing linker comprising a C$_1$-C$_{10}$ alkylene, C$_1$-C$_{10}$ alkenylene, —O—C$_{1-10}$—, —CONH—C$_{1-10}$—, —C$_{1-10}$—CONH—, —NHCO—C$_{1-10}$— or an aromatic ring; and W is a hydrogen, C$_1$-C$_{10}$ alkyl, C$_1$-C$_{10}$ alkenyl, C$_1$-C$_{10}$ alkyloxy, —CONH—C$_{1-10}$,—NHCO—C$_{1-10}$, —C$_{1-9}$CONHR$^1$, substituted or unsubstituted 5- or 6-member aromatic ring, hydroxyl, amino, cyano, or halogen;

L$^2$ is

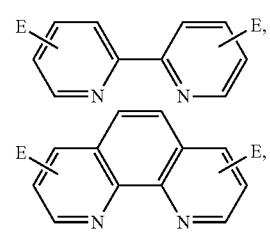

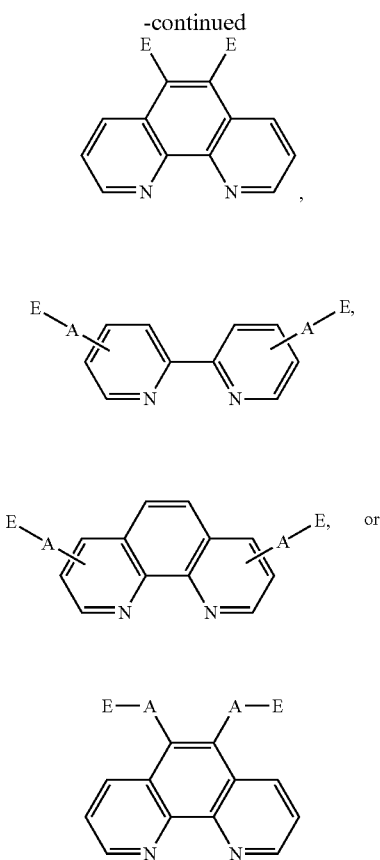

having at least one negatively charged substituent with a total number of negative charge equal to 2, wherein E is $-SO_3^{31}$, $-OSO_3^{31}$, $-PO_3H^{31}$, or $-OPO_3H^{31}$; and A is a carbon-containing or a heteroatom-containing linker comprising a $C_1$-$C_{10}$ alkylene, $C_1$-$C_{10}$ alkenylene, $-O-C_{1-10}-$, $-CONH-C_{1-10}-$, $-NHCO-C_{1-10}-$, $-C_{1-9}CONHR^2-$, substituted or unsubstituted 5-or 6-member aromatic ring;

$L^3$ is a 2,2'-bipyridine, or 1,10-phenanthroline, substituted with at least one W', wherein W' is a hydrogen, $C_1$-$C_{10}$ alkyl, $C_1$-$C_{10}$ alkenyl, $C_1$-$C_{10}$ alkyloxy, $-CONH-C_{1-10}$, $-NHCO-C_{1-10}$, $-C_{1-9}CONHR^3$, substituted or unsubstituted 5- or 6-member aromatic ring, hydroxyl, cyano, or halogen;

$L^1$, $L^2$ and $L^3$ are different from each other;

$R^1$, $R^3$ are each H, or alkyl; and $R^2$ is an alkylene comprising the steps of:

(a) forming a first intermediate (p-cymene)($L^1$)RuCl$_2$, (p-cymene)($L^2$)RuCl$_2$, or (p-cymene)($L^3$)RuCl$_2$ by reacting [(p-cymene)RuCl$_2$]$_2$ with $L^1$, $L^2$, $L^3$ respectively;

(b) converting the first intermediate to a second intermediate ($L^1$)($L^2$)RuCl$_2$, ($L^1$)($L^3$)RuCl$_2$, or ($L^2$)($L^3$)RuCl$_2$ by reacting the (p-cymene)($L^1$)RuCl$_2$ with $L^2$ or $L^3$, reacting the (p-cymene)($L^2$)RuCl$_2$ with $L^1$ or $L^3$, or reacting the (p-cymene)($L^3$)RuCl$_2$ with $L^1$ or $L^2$ respectively; and (c) converting the second intermediate to ($L^1$)($L^2$)($L^3$)Ru by reacting the ($L^1$)($L^2$)RuCl$_2$ with $L^3$, reacting the ($L^1$)($L^3$)RuCl$_2$ with $L^2$, or reacting the ($L^2$)($L^3$)RuCl$_2$ with $L^1$.

13. An electronically neutral and tris-heteroleptic metal complex:

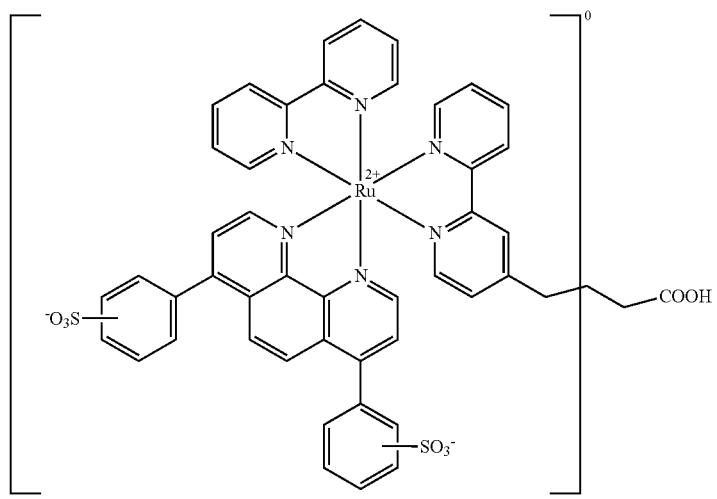

-continued
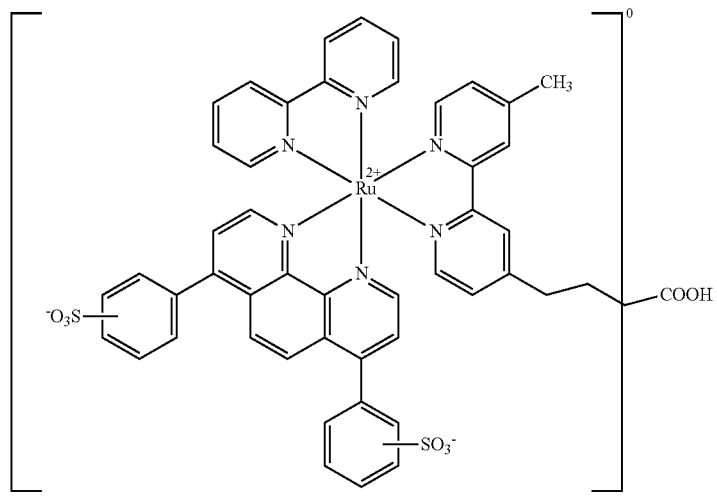
17
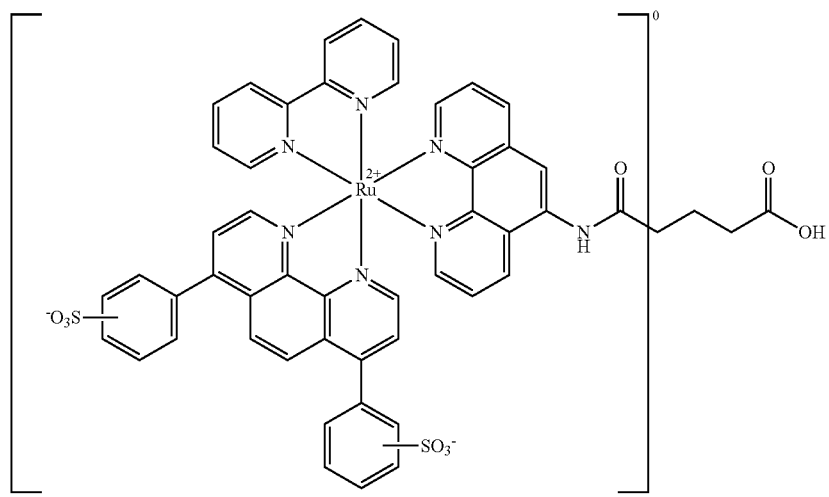
18
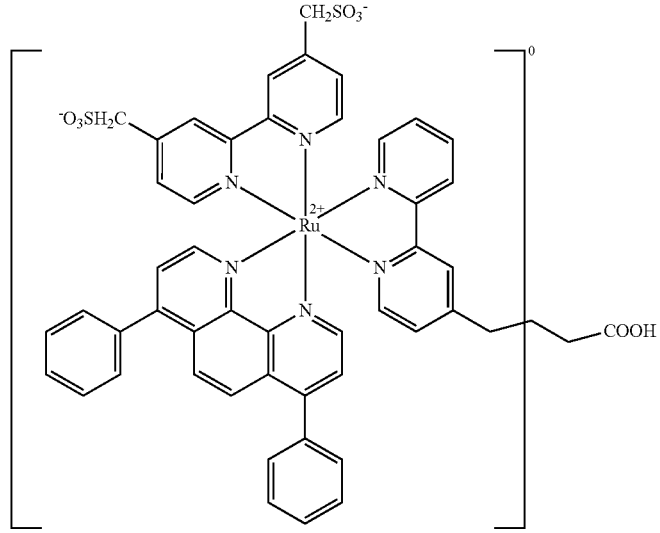
19

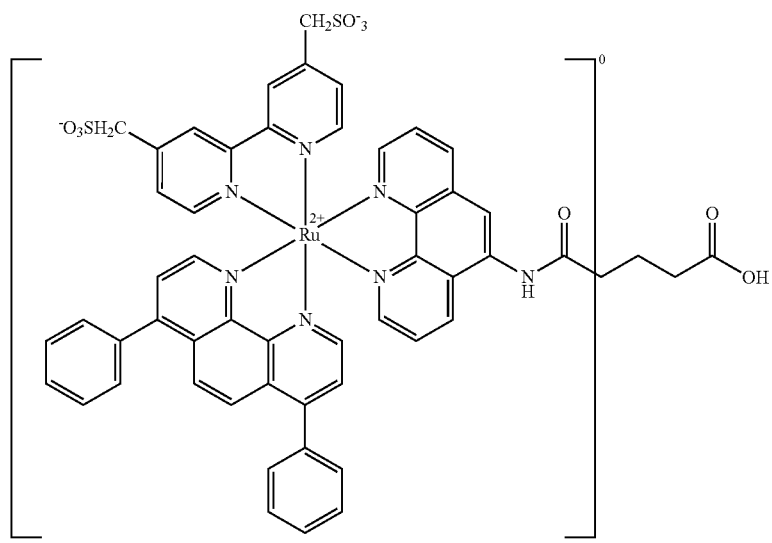
20
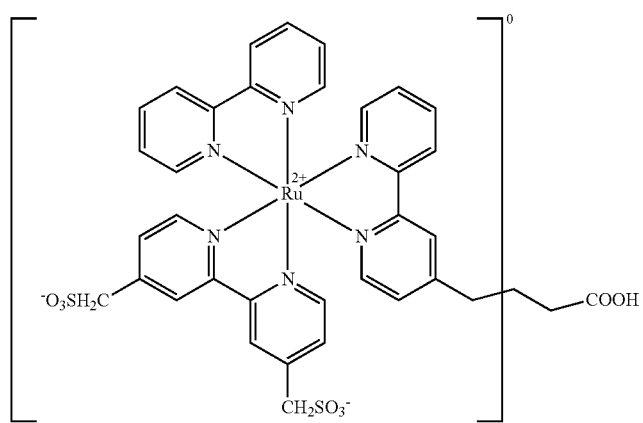
21
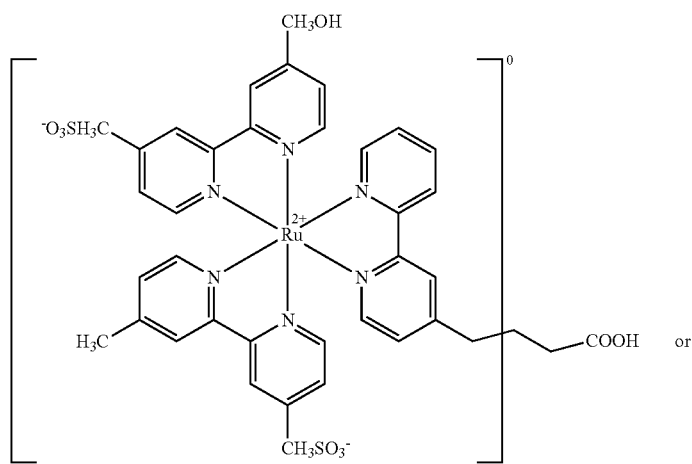
24
or

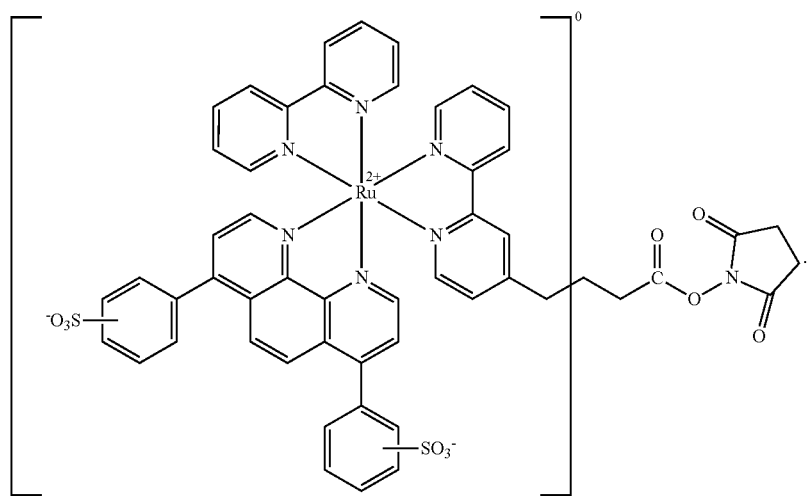
* * * * *